US006240309B1

(12) United States Patent
Yamashita et al.

(10) Patent No.: US 6,240,309 B1
(45) Date of Patent: May 29, 2001

(54) OPTICAL MEASUREMENT INSTRUMENT FOR LIVING BODY

(75) Inventors: Yuichi Yamashita, Kawagoe; Atsushi Maki, Hachioji; Hideaki Koizumi, Tokyo, all of (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 08/875,081

(22) PCT Filed: Nov. 15, 1996

(86) PCT No.: PCT/JP96/03365
§ 371 Date: Sep. 29, 1997
§ 102(e) Date: Sep. 29, 1997

(87) PCT Pub. No.: WO97/18755
PCT Pub. Date: May 29, 1997

Related U.S. Application Data

(63) Continuation-in-part of application No. 08/539,871, filed on Oct. 6, 1995, now Pat. No. 5,803,909.

(30) Foreign Application Priority Data

| Nov. 17, 1995 | (JP) | 7-299542 |
| Nov. 30, 1995 | (JP) | 7-311993 |
| Dec. 1, 1995 | (JP) | 7-314195 |

(51) Int. Cl.[7] .................................... A61B 5/05
(52) U.S. Cl. .................. 600/407; 600/473; 600/476; 250/227.2; 250/528.1; 356/320; 356/435; 356/447
(58) Field of Search ............................ 600/473, 475, 600/476, 477, 403, 310; 356/319, 320, 323, 337, 341, 342, 345, 346, 349, 432, 433, 435, 445–448, 237, 239; 250/227.2, 227.21, 227.23, 227.28, 227.29, 574, 575, 578.1

(56) References Cited

U.S. PATENT DOCUMENTS

| 4,706,072 | * 11/1987 | Ikeyama ............................... 340/576 |
| 4,948,974 | * 8/1990 | Nelson et al. ........................ 600/473 |

(List continued on next page.)

FOREIGN PATENT DOCUMENTS

| 43 40 072 A1 | 6/1995 | (DE) . |
| 2 228 314 | 8/1990 | (GB) . |
| 63-5234 | 1/1988 | (JP) . |
| 63-305845 | 12/1988 | (JP) . |
| 7-117595 | 5/1995 | (JP) . |
| WO 93/25145 A1 | 12/1993 | (WO) . |
| WO 94/10901 A1 | 5/1994 | (WO) . |

Primary Examiner—Brian L. Casler
(74) Attorney, Agent, or Firm—Antonelli, Terry, Stout & Kraus, LLP

(57) ABSTRACT

Described herein is an optical measurement instrument for a living body, comprising light incident means for simultaneously applying incident light of a wavelength in a visible-infrared region to a plurality of incident positions on the surface of a subject, light detection means for simultaneously detecting lights obtained by allowing the incident light to pass through the subject, at a plurality of detection positions on the surface of the subject, and imaging means for imaging information on the inside of the subject using detected signals outputted from the light detection means. The light incident means includes light modulation means for intensity-modulating the incident light applied to the plurality of incident positions with modulation frequencies respectively different every the respective incident positions. The light detection means includes selection and detection means for selecting and detecting transmitted light components of modulation frequencies respectively different every respective detection positions from the transmitted lights relative to the plurality of detection positions.

12 Claims, 25 Drawing Sheets

U.S. PATENT DOCUMENTS

| | | | |
|---|---|---|---|
| 5,088,493 | * | 2/1992 | Giannini et al. .................. 600/310 |
| 5,090,415 | * | 2/1992 | Yamashita et al. ................ 600/476 |
| 5,416,582 | * | 5/1995 | Knutson et al. ................... 356/349 |
| 5,477,051 | * | 12/1995 | Tsuchiya ............................ 356/432 |
| 5,586,554 | * | 12/1996 | Maki et al. ........................ 600/407 |
| 5,596,987 | * | 1/1997 | Chance ............................... 600/310 |
| 5,664,574 | * | 9/1997 | Chance ............................... 600/473 |
| 5,673,701 | * | 10/1997 | Chance ............................... 600/473 |
| 5,694,938 | * | 12/1997 | Feng et al. ........................ 600/473 |
| 5,713,352 | * | 2/1998 | Essenpreis et al. ................ 600/310 |
| 5,787,887 | | 8/1998 | Klingenbeck-Regn . |
| 5,803,909 | * | 9/1998 | Maki et al. ........................ 600/310 |
| 5,807,263 | * | 9/1998 | Chance ............................... 600/476 |
| 5,820,558 | * | 10/1998 | Chance ............................... 600/473 |
| 5,853,370 | * | 12/1998 | Chance et al. ..................... 600/473 |
| 5,876,339 | * | 3/1999 | Lemire ............................... 600/425 |
| 5,907,406 | * | 5/1999 | Papaioannou et al. ............ 356/432 |
| 5,954,053 | * | 9/1999 | Chance et al. ..................... 600/310 |
| 5,987,351 | * | 11/1999 | Chance ............................... 600/473 |

* cited by examiner

○ INCIDENT POSITION (IP)  ● DETECTION POSITION (DP)
□ MEASUREMENT POSITION (MP)

FIG. 36

| MEASUREMENT REGION i \ CHARACTERISTIC PARAMETER j | 1 | 2 | ......... | m-1 | m |
|---|---|---|---|---|---|
| 1 | $S_{1,1,k}$<br>$A_{1,1,k}$ | $S_{1,2,k}$<br>$A_{1,2,k}$ | ......... | $S_{1,m-1,k}$<br>$A_{1,m-1,k}$ | $S_{1,m,k}$<br>$A_{1,m,k}$ |
| 2 | $S_{2,1,k}$<br>$A_{2,1,k}$ | $S_{2,2,k}$<br>$A_{2,2,k}$ | ......... | $S_{2,m-1,k}$<br>$A_{2,m-1,k}$ | $S_{2,m,k}$<br>$A_{2,m,k}$ |
| ⋮ | ⋮ | ⋮ | ⋱ | ⋮ | ⋮ |
| n-1 | $S_{n-1,1,k}$<br>$A_{n-1,1,k}$ | $S_{n-1,2,k}$<br>$A_{n-1,2,k}$ | ......... | $S_{n-1,m-1,k}$<br>$A_{n-1,m-1,k}$ | $S_{n-1,m,k}$<br>$A_{n-1,m,k}$ |
| n | $S_{n,1,k}$<br>$A_{n,1,k}$ | $S_{n,2,k}$<br>$A_{n,2,k}$ | ......... | $S_{n,m-1,k}$<br>$A_{n,m-1,k}$ | $S_{n,m,k}$<br>$A_{n,m,k}$ |

OPTICAL MEASUREMENT INSTRUMENT FOR LIVING BODY

CROSS REFERENCE TO RELATED APPLICATION

This is a continuation-in-part application of U.S. application Ser. No. 08/539,871, filed Oct. 6, 1995, by some of the inventors herein, now U.S. Pat. No. 5,803,909.

BACKGROUND OF THE INVENTION

1. Field of the Invention

The present invention relates to an instrument for measuring information on an inner living body with light.

2. Description of the Related Art

The development of a technique capable of measuring information about an inner living body with ease and without noninvasion on the living body has been long expected in the fields of clinical medicine and brain science or the like. Described specifically, as exemplary measurements for the brain, may be mentioned, measurements on brain diseases such as cerebral infarction, cerebral hemorrhage, and measurements on high-order brain functions such as thought, language, motor, etc. The object to be measured is not necessarily limited to the brain. Measurements for the chest may include heart diseases such as myocardial infarction, etc. and measurements for the abdomen may include prevention and diagnosis against internal diseases such as kidney, liver disorder, etc.

When the intracerebral diseases or high-order brain functions are measured with the brain as the object to be measured, it is necessary to definitely measure a disease part or a functional region. Therefore, it is of very importance that a wide region in the brain is measured as image information. As an example indicative of this importance, may be mentioned a positron emission tomography (PET) system used as an intracerebral imaging measurement system, and a functional magnetic resonance imaging (fMRI) system, which are now widely used. These systems have drawbacks in that although they have an advantage that the wide region in the living body can be measured as the image information, they are large in size and their handling is cumbersome. For example, a dedicated room is required to install these systems and the systems are not easy to move as a matter of course. Thus, restraint on a subject is enhanced. Further, since persons dedicated to maintenance are required, considerable costs are required for practical use of these systems.

The optical measurement technique holds great promise from the above point of view. A first reason of its promise is that the normality and abnormality of organs and the brain activity about the high-order brain function are closely related to oxygen metabolism and blood circulation inside the living body. The oxygen metabolism and blood circulation correspond to the concentration of specific chromophones (such as hemoglobin, cytochrome $aa_3$, myoglobin) in the living body. The concentration of chromophones can be determined from the absorbance of visible-infrared region light. Further, second and third reasons why the optical measurement technique is effective, are that the light can be easily handled owing to optical fibers and does no harm to the living body due to the use of the light within a safety standard range. Thus, the optical measurement technique has advantages of real time measurements and quantification of the concentration of the chromophones in the living body, and the like that the PET and fMRI lack. Further, the optical measurement technique is suitable for size reductions in the systems and simplicity of their handling.

An instrument capable of irradiating a living body with visible-infrared region light and detecting light (reflected light) subject to absorption and scattering inside the living body and discharged to the outside of the living body to thereby measure information on the inner living body, using the advantages of the optical measurement technique, has been described in, for example, Japanese Patent Application Laid-Open Nos. 57-115232, 63-260532, 63-275323 and 5-317295.

However, in the aforementioned conventional living body measurement technique using the light, the information can be measured only at a specific position in the living body or within a restricted narrow region. Therefore, imaging about a wide spatial region inside the living body has not been taken into consideration.

Specific problems about an optical measurement method and a layout configuration of light incident positions and light detection positions, which are employed in the prior art, will now be described.

The optical measurement method will first be described. It is necessary to irradiate many positions with light and detect it at many points upon imaging in the wide spatial region. One example of this type of multiposition measurement will be explained in brief with reference to FIG. 2. The present example shows the case in which lights are applied or irradiated from three points (incident positions IP1, IP2 and IP3) on the surface of a subject and the lights reflected therefrom are detected at three points (detection positions DP1, DP2 and DP3) on the surface of the subject. Measurement positions must be specified upon imaging. Light propagation in scattering media (e.g., living body) has been reported by, for example, [N. C. Bruce; "Experimental study of the effect of absorbing and transmitting inclusions in highly scattering media", Applied Optics, vol. 33, no. 28, pp. 6692–6698, (October 1994)]. Its experimental results are shown in FIG. 3. It is known from FIG. 3 that the neighborhood of a middle point between a light incident position and a light detection position includes information about a position deep from the surface of the living body. Thus, when the deep position in the living body, e.g., a deeper position of skin or skull, for example, is measured from above the skin, the middle position between the incident position and the detection position results in a measurement position. Such measurement needs to provide the incident positions and the detection positions one by one in pairs and obtain information at measurement positions (measurement positions MP1, MP2 and MP3) specified every individual pairs.

Now consider, for example, a case in which in the layout configuration shown in FIG. 2, the lights are simultaneously applied from the three incident points (incident positions IP1, IP2 and IP3) and the lights reflected therefrom are simultaneously detected at the three light detection points (detection positions DP1, DP2 and DP3). In this case, it is necessary to accurately measure only the reflected light of the light applied from the incident position IP2 at the detection position DP2 upon measurement at the measurement position MP2 corresponding to the middle point between the incident position IP2 and the detection position DP2. However, the light detected at the detection position 2 actually includes the reflected lights of the lights incident from the incident positions IP1 and IP3 as well as the reflected light of the light incident from the incident position IP2. As a result, so-called crosstalk is produced.

Accordingly, only the reflected light of the light incident from the incident position IP2 cannot be separated and detected at the detection position DP2, so that the accurate measurement on the measurement position MP2 cannot be carried out.

Thus, if a switch or the like is used so as to successively switch between the incident positions every measurement positions on a time-sequence basis, such crosstalk is prevented from occurring. However, in order to successively switch between many incident positions, much time is required correspondingly upon their switching. Therefore, a long time is required for measurement, so that the measurement is rendered inefficient.

Thus, there has been a strong demand for the development of a simultaneous multichannel measurement technique capable of performing measurements on a large number of measurement positions in a subject simultaneously and without crosstalk in order to make imaging about a wide spatial region in the subject.

It is also necessary to measure information about an inner brain covered with a head scarf skin and a skull fracture with high sensitivity and satisfactory efficiency upon intra-living body measurement, particularly brain functional measurement. In the optical measurement method, the information on the deep position in the living body is detected at the middle position between the light incident position and the light detection position. If a plurality of pairs of light incident positions and light detection positions are disposed on the circumference surrounding measured portions and middle-point positions between the respective pairs are placed in common use, as a method of measuring the deep position information with high sensitivity, i.e., measuring the deep position information so that the deep position information is contained in more plenty, information on the deep position in the living body, which corresponds to each common middle-point position, can be measured with high sensitivity. Even in this case, however, the simultaneous measurement, i.e., the simultaneous multichannel measurement on the aforementioned plurality of pairs of light incident positions and light detection positions must be executed to perform the measurement in a short time and with satisfactory accuracy.

Moreover, the operations of various apparatuses typified by a computer and the input of information are now performed via a keyboard or a switch and the like. However, there may be cases in which a physically handicapped person encounters difficulties in performing such operations and information input work. There may also be cases where even a normal person cannot always take quick and appropriate measures in case of emergency of the driving of a vehicle and the operation of a large-scale plant, for example. If, in such a case, the operator can take quicker and more appropriate measures before the limbs of the operator show reactions, it is then possible to beforehand prevent serious accidents from occurring. Therefore, a method of measuring the state of activity of a function of perception and cognition in the operator's brain in real time and directly inputting a signal about a change of brain activity referred to above to the above-described various apparatuses is considered. However, the measurement of the brain activity with high sensitivity and high accuracy is indispensable to the reliable execution of the operation by such a method. Therefore, a technique for performing the aforementioned multichannel simultaneous measurement without the crosstalk is also required.

SUMMARY OF THE INVENTION

With the foregoing in view, it is therefore an object of the present invention to provide an optical measurement instrument for a living body, capable of performing an optical measurement about a wide spatial region in a subject (living body) with high efficiency and satisfactory accuracy.

It is another object of the present invention to provide a small-sized and easy-to-handle optical measurement instrument for a living body, capable of performing an optical measurement on a wide spatial region in a subject.

It is a further object of the present invention to provide a simultaneous multichannel measurement method capable of performing optical measurements on a plurality of measurement positions in a subject simultaneously and without crosstalk.

It is a still further object of the present invention to provide an optical measurement instrument for a living body, capable of measuring information on a deep position in a subject with high sensitivity.

It is a still further object of the present invention to provide high-utility input and control devices by a living body, which are capable of controlling various pieces of external equipment with high accuracy by using living-body measurement signals high in spatial resolution, which are obtained from the above-described optical measurement instrument, as input signals.

According to one aspect of the present invention, for achieving the above objects, there is provided an optical measurement instrument for a living body, for simultaneously launching lights of wavelengths in a visible-infrared region into a subject from a plurality of incident portions on the surface of the subject (living body), simultaneously detecting lights transmitted through the subject and discharged outside the subject again at a plurality of detection portions on the surface of the subject, and imaging living-body information on the inside of the subject, using the detected signals, wherein the incident lights from the plurality of incident portions are intensity-modulated with modulation frequencies respectively different every respective incident portions, and lights of modulation frequencies respectively different every respective detection portions are separated and/or selected and detected at the plurality of detection portions.

According to the above construction of the present invention, light of a specific modulation frequency, which has been detected at a specific detection portion, corresponds to only an incident light launched from a specific incident portion irradiated with the light of the specific modulation frequency. Thus, information on the living body at a specific measurement portion in the subject, which is determined in association with the specific incident and detection portions referred to above, can be obtained without crosstalk. As a result, living-body information about a plurality of measurement portions in the subject can be obtained simultaneously and without crosstalk and hence a simultaneous multichannel measurement can be carried out. Further, an optical measurement on a wide spatial region including the plurality of measurement portions in the subject can be carried out with high efficiency and satisfactory accuracy.

If the lights selected and detected at the respective detection portions are respectively changed to light of another modulation frequency in the above-described construction of the present invention, living-body information at another measurement portion in the subject, which is determined in association with an incident portion irradiated with the light of another modulation frequency and a detection portion where the light has been detected, can be obtained without crosstalk in the same manner as described above. Thus, the numbers of the incident portions and the detection portions, which are required to carry out measurements on a predetermined number of measurement portions, can be reduced respectively. Accordingly, an instrument configuration can be obtained which is capable of reducing the number of light sources for light irradiation and the number of detectors for optical detection and providing a less size and easy handling.

Further, according to the present invention, since the measurements on the plurality of measurement channels formed between the plurality of light incident positions and the plurality of light detection positions can be carried out simultaneously and without crosstalk as described above, the plurality of pairs of these light incident positions and light detection positions are disposed on the circumference surrounding the specific portions to be measured corresponding to the deep positions in the subject and the middle-point positions (measurement positions) of the respective pairs are caused to coincide with the specific measured portions. As a result, only the information at the specific measured portions can be selectively and concentratedly detected. Thus, the living-body information at each specific portion corresponding to the deep position can be measured with high sensitivity.

Moreover, according to the present invention, since the optical measurement instrument for the living body can be implemented which is capable of measuring the living-body information about the wide spatial region in the subject (living body) with high efficiency and accuracy and at high spatial resolution as described above, the high-utility input and control devices by living body can be implemented which is capable of controlling these various external equipment promptly and with high accuracy by using the measurement signals outputted from the optical measurement instrument as the signals to be directly inputted to the various external equipment.

Typical ones of various inventions of the present application have been shown in brief. However, the various inventions of the present application and specific configurations of these inventions will be understood from the following description.

BRIEF DESCRIPTION OF THE DRAWINGS

While the specification concludes with claims particularly pointing out and distinctly claiming the subject matter which is regarded as the invention, it is believed that the invention, the objects, and features of the invention and further objects, features and advantages thereof will be better understood from the following description taken in connection with the accompanying drawings in which:

FIG. 36 is a diagram showing a data structure of learning data, which is employed in the second operation procedural example shown in FIG. 35.

DETAILED DESCRIPTION OF THE PREFERRED EMBODIMENTS

The present invention will hereinafter be described in detail with reference to the accompanying drawings.

Simultaneous Multichannel Measurement

The present invention provides a simultaneous multichannel measurement technique capable of performing optical measurements about a plurality of measurement positions in a subject (living body) simultaneously and without crosstalk to make it possible to effect high-efficient and satisfactory-precision optical measurements on a wide space region in the subject (living body).

That is, in order to solve the aforementioned crosstalk problem, the present invention provides an optical measurement instrument for a living body, for simultaneously irradiating an inner subject with visible-infrared region light from a plurality of incident positions on the surface of the subject (living body), simultaneously detecting lights transmitted through the inner subject and discharged out of the subject again at a plurality of detection positions on the surface of the subject, and imaging and measuring living-body information about the inner subject using the detected signals, wherein modulation frequencies of the lights launched within the subject from the plurality of incident positions are made different from one another every incident positions and the lights having the modulation frequencies different from each other every detection portions are selectively separated and detected at the plurality of detection positions.

Figure 2:
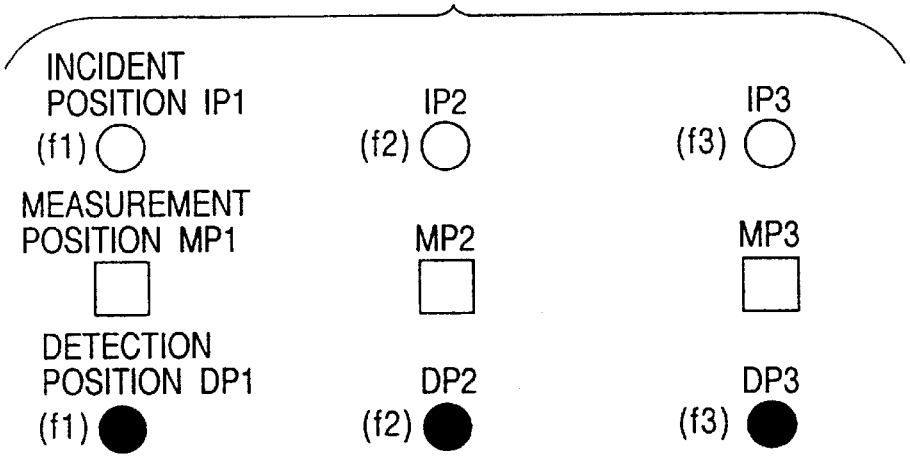
FIG. 2 is a diagram illustrating the relationship of layouts between light incident positions, light detection positions and measurement positions employed for a living body optical measurement.
Figure 3:
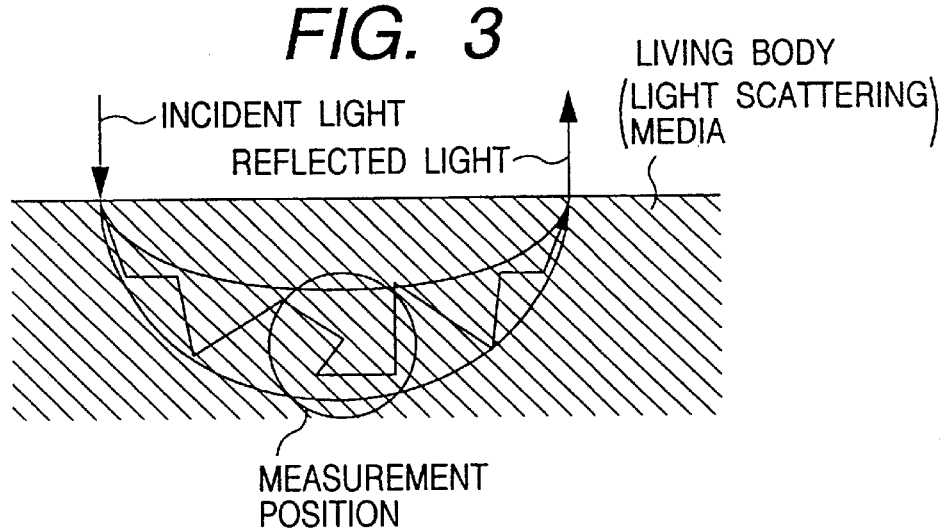
FIG. 3 is a diagram showing the manner of light propagation in a living body (scattering media) at the living body optical measurement.

Referring to FIG. 2, for example, lights intensity-modulated with modulation frequencies f1, f2 and f3 different from each other are simultaneously applied from incident positions IP1, IP2 and IP3. At detection positions DP1, DP2 and DP3, only the lights having the modulation frequencies f1, f2 and f3 are selectively separated and detected so as to correspond to the incident positions IP1, IP2 and IP3. Thus, only the light having the modulation frequency f2, which has been applied from the incident position IP2 and has passed into or through a subject (living body), can be separated from the lights having the modulation frequencies f1 and f3 incident from the incident positions IP1 and IP3 and selectively detected at the detection position DP2, for example. Namely, only the components of the light incident from the incident position IP2 are contained in the light detected at the detection position DP2, and no components of the lights incident from other incident positions IP1 and IP3 are contained therein. Thus, the light (corresponding to the light passing through the living body) having the modulation frequency f2, which has been selected and detected at the detection position DP2, includes inner living-body information at a measurement position MP2 located between the incident position IP2 and the detection position DP2 in plenty. However, the light little contains inner living-body information on measurement positions MP1 and MP3. Namely, information about other measurement positions MP1 and MP3 are not mixed into the information about the measurement position MP2 to be measured at the detection position DP2. This is entirely the same even to other detection positions DP1 and DP3. Thus, crosstalk-free measurements can be made to the respective measurement positions.

When a plurality of lights different in wavelength from each other are used as lights to be incident onto a living body and the lights transmitted through the living body are spectroscopically measured in order to quantitatively measure concentrations of chromophones such as hemoglobin, cytochrome $aa_3$, myoglobin, etc. in the living body, modulation frequencies different every wavelengths can be assigned and applied to the plurality of incident lights. In doing so, a plurality of lights different in wavelength can be electrically spectroscopically-measured by separating and detecting (lock-in detecting) the plurality of lights different in wavelength transmitted through the same measurement positions and reaching the same detection positions every their modulation frequencies, without depending on a spectroscopic method accompanied with optical losses such as reflection, scattering, etc. of an optical filter, grating, a prism or the like, etc.

If a method of modulating the incident lights with the different modulation frequencies is used, then lights incident from other incident positions can be also detected at respective detection positions by changing modulation frequencies of lights selected and detected at the respective detection positions. If the modulation frequency of the light detected at the detection position DP2 is set to f2 when the modulation frequencies of the lights incident from the incident positions IP1, IP2 and IP3 are respectively f1, f2 and f3 in FIG. 2, for example, then only the light incident from the incident position IP2 is selected and detected at the detection position DP2. However, if the modulation frequency of the light detected at the detection position DP2 is changed to f1 and f3, it is then possible to select and detect only the lights incident from the incident positions IP1 and IP3. This is similar to the above even in the case of the detection positions DP2 and DP3. Since this advantage further relates to the layout of more efficient light incidence/detection points, the details thereof will next be described.

Figure 4:
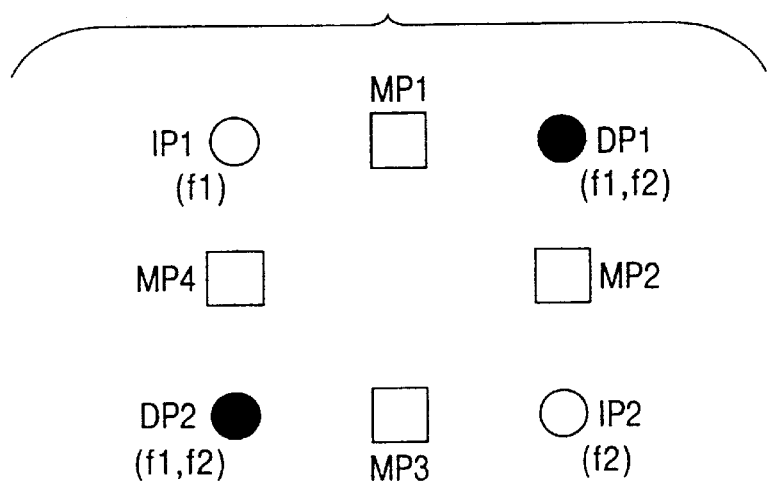
FIG. 4 is a diagram showing the relationship of placement between light incident positions, light detection positions and measurement positions for implementing a more efficient living body optical measurement by the present invention.

When specific incident positions and detection positions are exclusively assigned to a plurality of measurement positions every measurement positions, i.e., when the number of the measurement positions is three as shown in FIG. 2, for example, the number of the incident positions and the number of the detection positions need three respectively. Thus, if incident positions IP1 and IP2 and detection positions DP1 and DP2 are alternately placed in lattice form to enable the sharing of the incident position IP1 between measurement positions MP1 and MP4 and the sharing of the incident position IP2 between measurement positions MP2 and MP3 and to enable the sharing of the detection position DP1 between the measurement positions MP1 and MP2 and the sharing of the detection position DP2 between the measurement positions MP3 and MP4 as shown in FIG. 4, then the number of the incident positions and the number of the detection positions necessary for the total four measurement positions can be set to two respectively. Namely, when modulation frequencies of lights incident from the incident positions IP1 and IP2 shown in FIG. 4 are respectively set to f1 and f2 and modulation frequencies of lights detected at the detection positions DP1 and DP2 are respectively set to f1 in accordance with the aforementioned modulation measurement method, information about the measurement positions MP1 and MP4 can be selected and measured at the detection positions DP1 and DP2. On the other hand, when the modulation frequencies of the lights detected at the detection positions DP1 and DP2 are set to f2, information about the measurement positions MP2 and MP3 can be selected and measured at the detection positions DP1 and DP2. Thus, the number of the incident positions (hence the number of light sources accompanied therewith) and the number of the detection positions (hence the number of detection devices accompanied therewith) can be greatly reduced and systematic efficiency can be improved. Further, the instrument configuration can be set to a small-sized and easy-to-handle one.

The present invention will hereinafter be described in detail by embodiments.

<<First Embodiment>>

Figure 1:
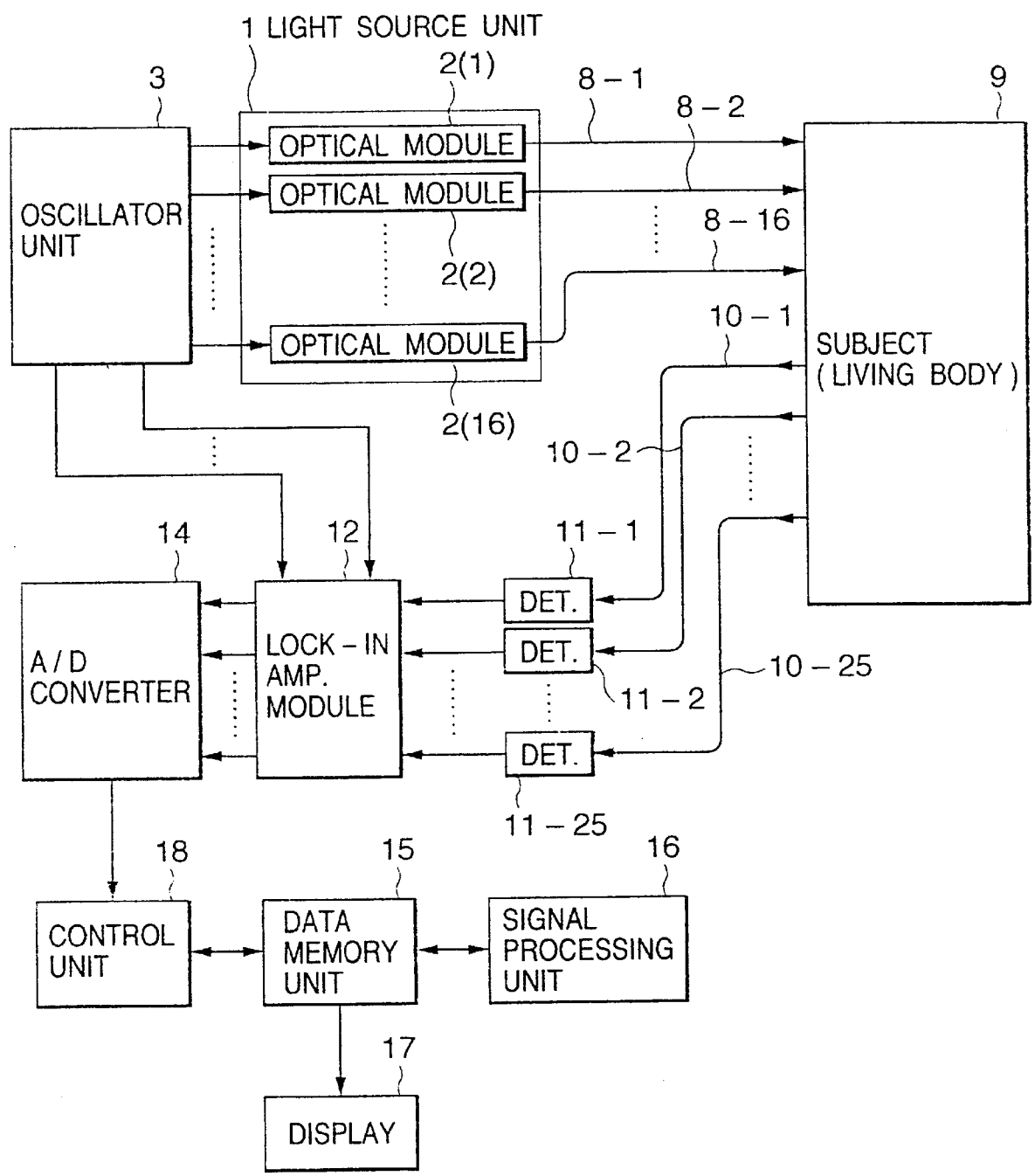
FIG. 1 is a diagram schematically showing a configuration of an optical measurement instrument for a living body, according to a first embodiment of the present invention.

FIG. 1 schematically illustrates a configuration of an optical measurement instrument for a living body, according to a first embodiment of the present invention.

The present embodiment shows an instrument configuration wherein the number of measurement channels (i.e., the number of measurement positions) is set to 64 assuming that an inside cerebrum is imaged and measured by applying light to it from above the scarf skin of a human head, for example and detecting the light.

A light source unit 1 comprises sixteen optical modules 2(1), 2(2), . . . and 2(16). Each of the optical modules 2(1), 2(2), . . . and 2(16) comprises three laser diodes which respectively individually apply lights having a plurality of wavelengths (three wavelengths of 770 nm, 805 nm and 830 nm, for example) placed within a visible-infrared wavelength region. All the laser diodes (48 diodes in total) included in the light source unit 1 respectively produce or emit laser beams modulated by different modulation frequencies in response to modulation signals outputted from an oscillator unit 3 composed of forty-eight oscillators whose oscillation frequencies differ from each other.

Figure 5:
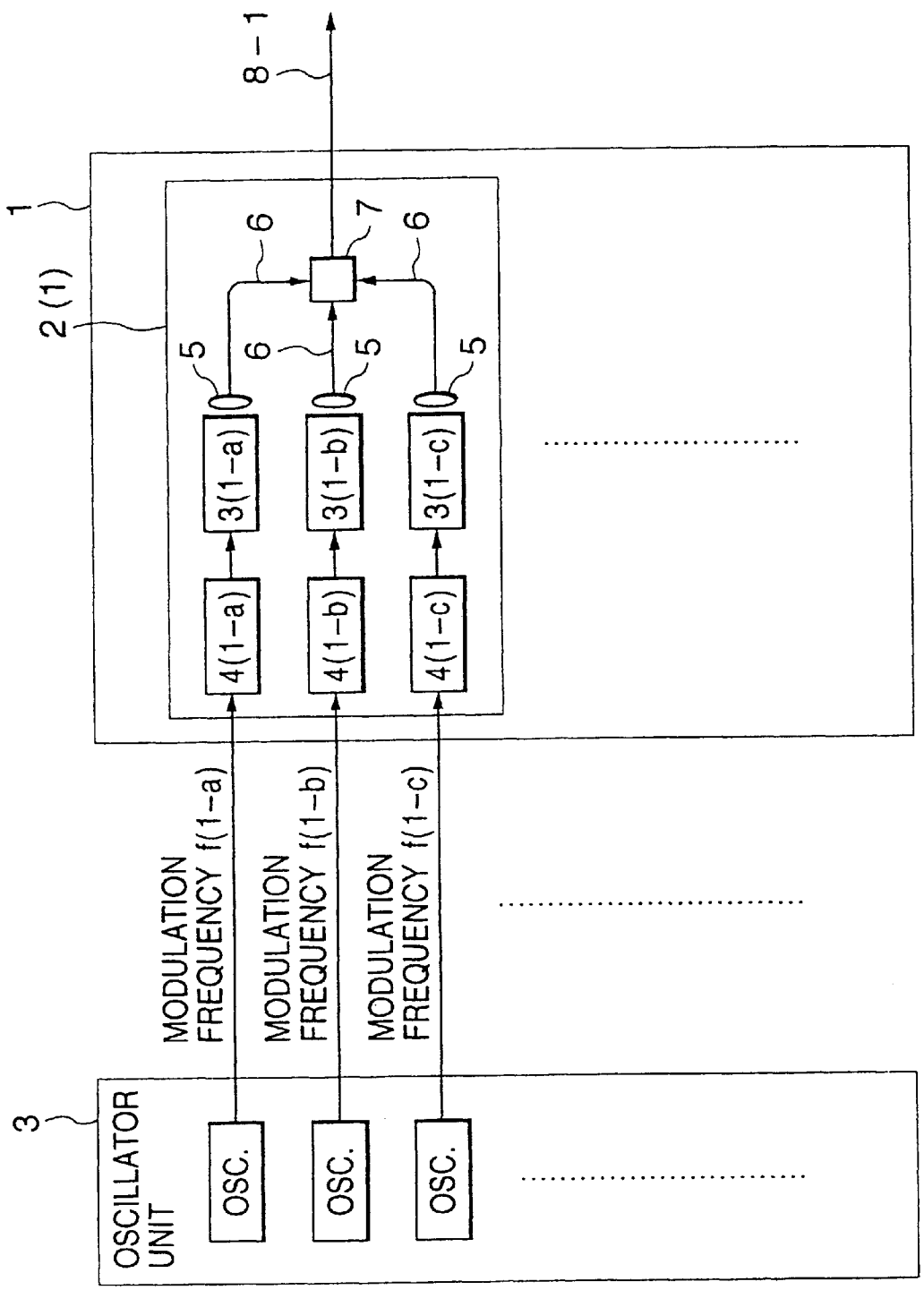
FIG. 5 is a diagram illustrating specific configurations of respective optical modules employed in the embodiment shown in FIG. 1.

FIG. 5 shows specific configurations inside the respective optical modules. The optical module 2(1) includes therein laser diodes 3(1-a), 3(1-b) and 3(1-c) and driver circuits 4(1-a), 4(1-b) and 4(1-c) for these laser diodes. Now, the figures (1) inside the parentheses, which exist within reference numerals assigned to the elements of structure, indicate elements that belong to the inside of the optical module of a module number 1. The alphabetical characters (a, b, c) respectively indicate elements included in a circuit unit for outputting laser beams respectively having wavelengths a (770 nm), b(805 nm) and c(830 nm). Output laser beams produced from the laser diodes 3(1-a), 3(1-b) and 3(1-c) are modulated with their corresponding modulation frequencies by supplying modulation signals having different modulation frequencies f(1-a), f(1-b) and f(1-c) to the driver circuits 4(1-a), 4(1-b) and 4(1-c) from their corresponding oscillators in the oscillator unit 3. The output laser beams produced from the respective laser diodes are individually introduced into optical fibers 6 through lenses 5. The lights introduced into the individual optical fibers 6 are introduced into a single incident optical fiber 8-1 through an optical fiber coupler 7.

Thus, the three lights different in wavelength from each other are introduced into the incident optical fibers 8-1, 8-2, . . . and 8-16 every optical modules. The lights, which have passed through the sixteen incident optical fibers, are respectively simultaneously applied to a subject 9 from different sixteen incident positions on the surface of the subject 9. Since the three types of lights different in wavelength and modulation frequency from one another are simultaneously applied from the respective incident positions, the forty-eight types of lights in total are simultaneously launched into the subject 9.

Next, lights (corresponding to lights subjected to absorption and scattering by having passed through the subject and emitted from the surface of the subject to the outside) reflected from the subject 9 are taken in detection optical fibers 10-1, 10-2, . . . and 10-25 disposed at twenty-five detection positions in total on the surface of the subject.

Figure 6:
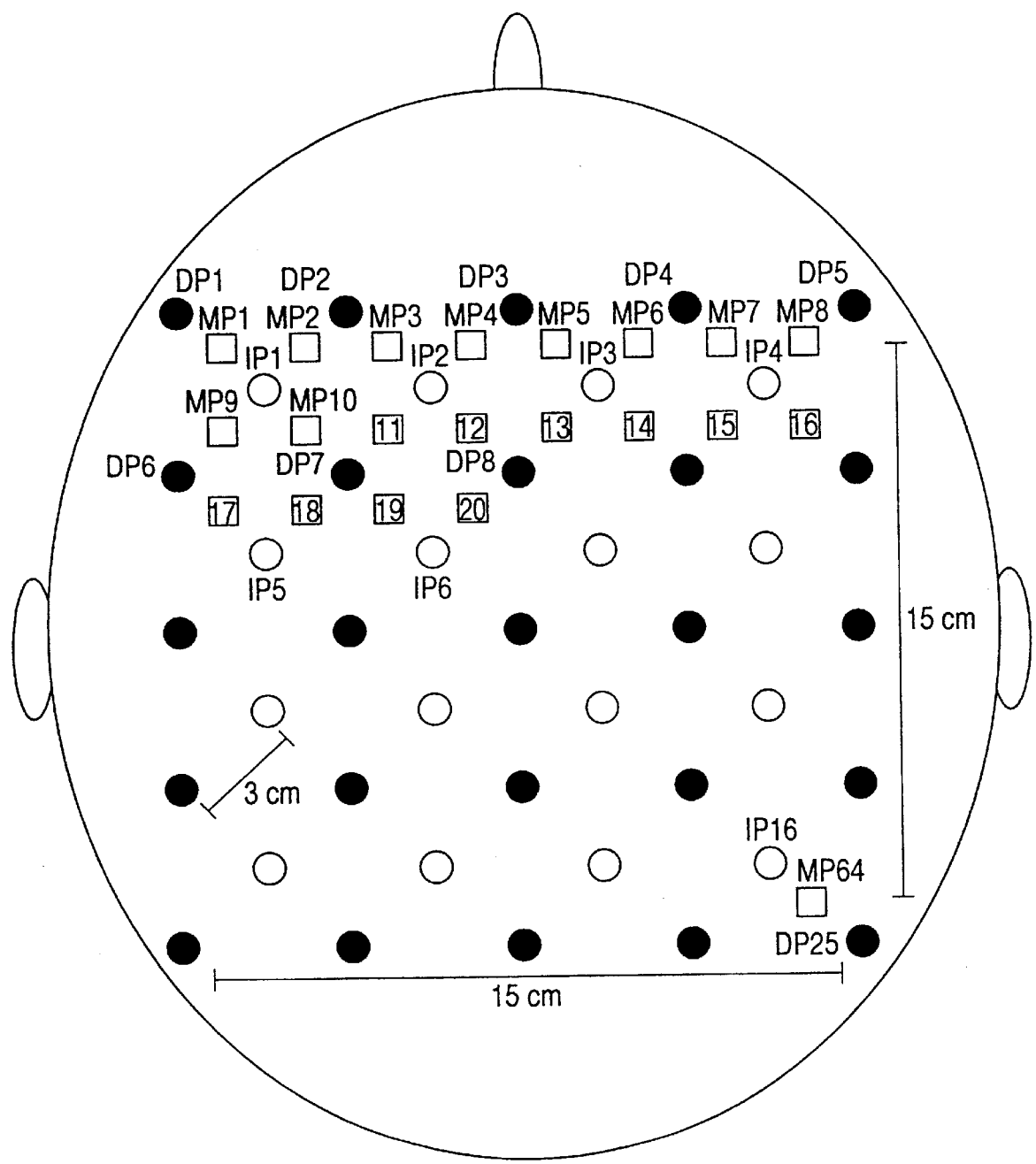
FIG. 6 is a diagram depicting the relationship of placement between light incident positions, light detection positions and measurement positions on the surface of a subject, which are employed in the embodiment shown in FIG. 1.

FIG. 6 shows an example of a geometrical layout of incident positions (IP)1 through (IP)16 and detection positions (DP)1 through DP(25) on the surface of the subject 9. In the present embodiment, the incident positions (IP) and the detection positions (DP) are alternately disposed in square lattice form. Assuming that middle points between the incident positions (IP) and detection positions (DP) adjacent to one another are defined as measurement positions (MP), the number of combinations of the incident positions (IP) and detection positions (DP) adjacent to one another exist as 64 types. Therefore, the number of the measurement positions (MP), i.e., the number of measurement channels results in 64.

It has been reported by, for example, [P. W. McCormic; "Intracerebral penetration of infra-red light", J. Neurosurg., vol. 76, pp. 315–318, (1992)] that assuming that the interval between the incident position and detection position adjacent to each other is set to about 3 cm when the subject 9 is a human head, light detected at each incident position has information about the inside cerebrum. Thus, if the sixty-four measurement channels are set in the layout configuration shown in FIG. 6, intracerebral information can be measured in an about 15 cm×15 cm wide region as a whole.

The reflected lights captured by the detection optical fibers 10-1 through 10-25 are separately detected by twenty-five optical detection devices (e.g., photo-diodes) 11-1, 11-2, . . . and 11-25 in total every detection positions (i.e., every detection optical fibers). Electric signals outputted from the respective optical detection devices are separated and measured by a lock-in amplifier module 12 composed of a plurality of lock-in amplifiers every incident positions and modulation frequencies corresponding to the wavelengths of the incident light.

Figure 7:
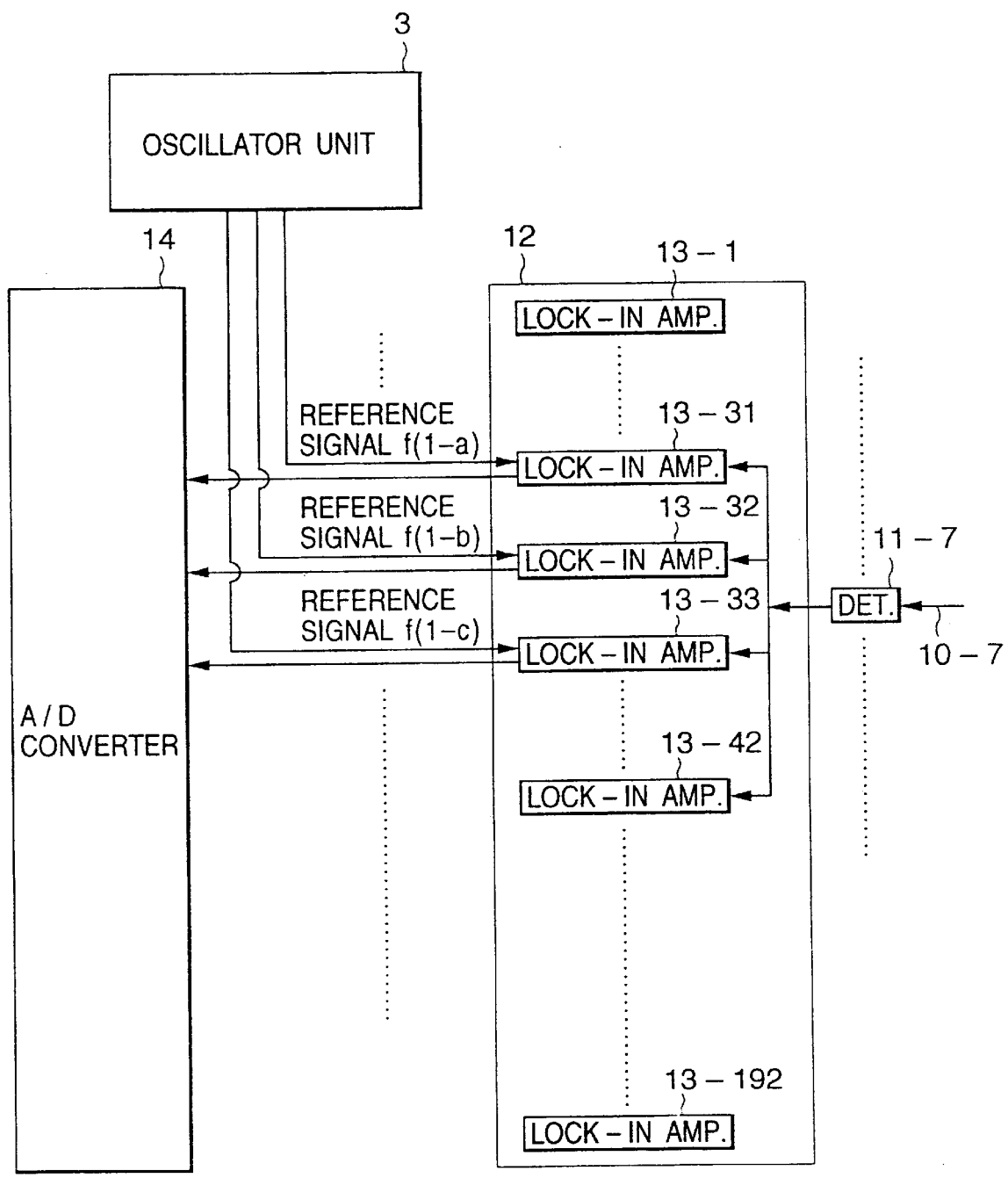
FIG. 7 is a diagram showing a specific configuration of a lock-in amplifier module employed in the embodiment shown in FIG. 1.

A specific example of a signal separation method will now be described with reference to FIG. 7 by using a signal detected at a detection position (DP)7 shown in FIG. 6, i.e., a signal detected at the optical detection device (photodiode) 11-7 as an example. At the detection position (DP)7, lights or light beams incident from four incident positions (IP)1, (IP)2, (IP)5 and (IP)6 adjacent to the detection position (DP)7, i.e., lights transmitted through measurement positions (MP)10, (MP)11, (MP)18 and (MP)19 are used for detection. The light detected by the optical detection device 11-7 principally contains twelve types of modulation signals comprising modulation frequencies f(1-a), f(1-b), f(1-c), f(2-a), f(2-b), f(2-c), f(5-a), f(5-b), f(5-c), f(6-a), f(6-b) and f(6-c) incident from the incident positions (IP)1, (IP)2, (IP)5 and (IP)6. Therefore, the signal outputted from the optical detection device 11-7 is distributed and inputted to twelve lock-in amplifiers 13-31, 13-32, . . . and 13-42 in which their corresponding modulation frequencies are defined as reference signals, where the distributed signals are separated and amplified every modulation frequencies. Since a reference signal frequency is set to f(1-a) at the lock-in amplifier 13-31, for example, only a signal component corresponding to light (i.e., light whose modulation frequency is f(1-a)) having a wavelength of 770 nm, which is incident from the incident position (IP)1, is separated and/or selected from the lightwave signals detected by the optical detection device 11-7 and amplified. Namely, a signal outputted from the lock-in amplifier 13-31 includes only living-body reaction information such as absorption and scattering, etc. with respect to the light having the wavelength of 770 nm at the measurement position (MP)10 existing between the incident position (IP)1 and the detection position (DP)7. Even in the case of other lock-in amplifiers, only lights having specific wavelengths, which have been applied from specific incident positions respectively, are selectively detected in the same manner as described above.

Thus, the individual lock-in detection of lightwave signals detected at other detection positions, i.e., signals detected by other optical detection devices with intrinsic modulation frequencies defined in association with their corresponding light incident positions and incident light wavelengths makes it possible to separate and measure the quantities of detected lights with respect to all the measurement positions and incident light wavelengths. When the three lights of wavelengths are respectively measured at the sixty-four measurement positions shown in the present embodiment, the 192 lock-in amplifiers 13-1, 13-3, . . . and 13-192 in total are included in the lock-in amplifier module 12.

Analog output signals produced from these 192 lock-in amplifiers are respectively converted into digital signals by an analog-to-digital converter 14 having 192 channels. The converted digital signals are recorded in a data memory unit 15 through a control unit 18. The recorded signals, i.e., concentrations in oxy- and deoxy-hemoglobin and the total concentration in hemoglobin corresponding to the sum of these hemoglobin concentrations are arithmetically processed and determined by a signal processing unit 16 using the quantities of detection lights with respect to the three wavelengths every measurement positions in accordance with, for example, a method described in the writings [two-wavelength Spectrophotometry and Its Application] edited by Shozo Shibata, et al. published in 1979 by Kodansha.

The concentrations in oxy- and deoxy-hemoglobin and the total concentration in hemoglobin determined every measurement positions are displayed on a display 17 as topographic images, for example. Incidentally, data used for the display of the topographic images are determined by interpolating (e.g., linear-interpolating) the respective hemoglobin concentrations at the respective measurement positions between the measurement positions. The above-described operations of the respective units in the instrument are controlled by the control unit 18.

Figure 8:
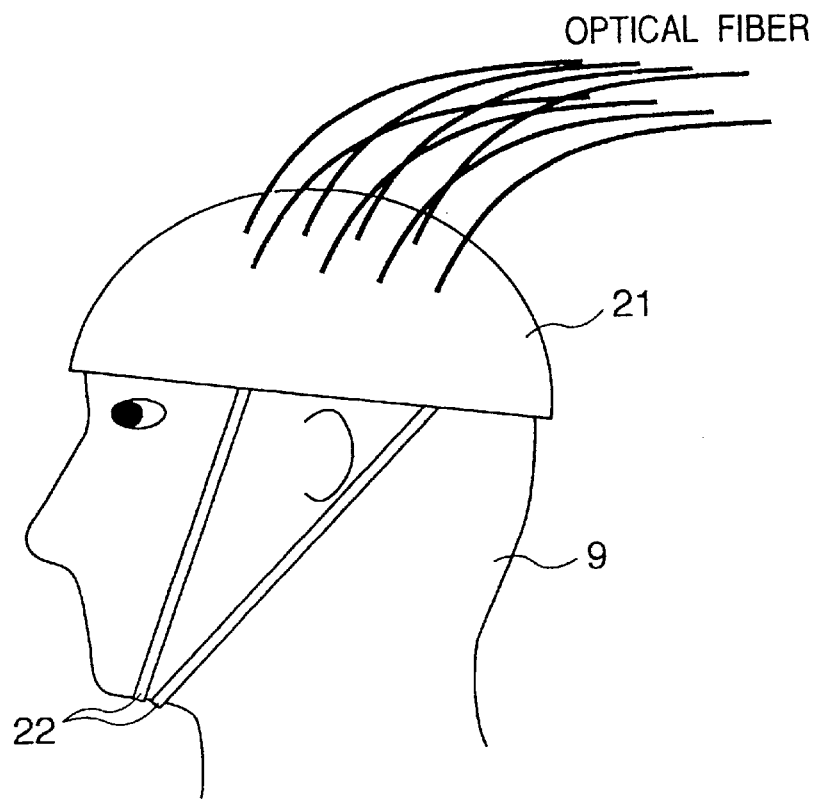
FIG. 8 is a diagram illustrating the shape of a probe employed in the embodiment shown in FIG. 1.
Figure 9:
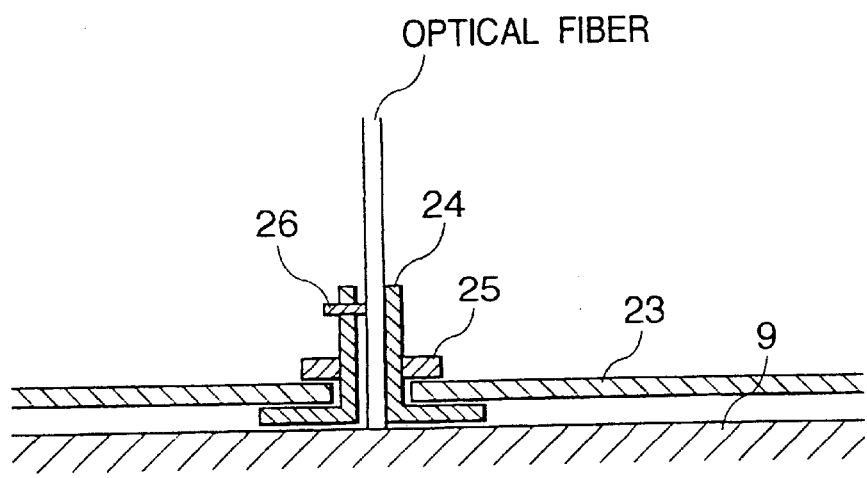
FIG. 9 is a diagram depicting a specific configuration of the probe shown in FIG. 8.

A helmet or cap-shaped probe 21 shown in FIG. 8, for example, is used for the application of light to a subject (human head) and its detection. The probe 21 is constructed by, for example, using a thermo-plastic sheet having a thickness of about 3 mm as a base material, forming a mold matched with outside dimensions in a subject measurement region in advance with the based material, and fixing and mounting it to the outer surface of the subject with elastic cord braids 22 or the like, for example. An example of a more specific structure of the probe 21 will be described with reference to FIG. 9. Holes are defined in a probe base 23 at a plurality of positions corresponding to the positions of application of light to the subject 9 and the positions for detection of light reflected from the subject 9. Further, optical fiber holders 24 are fixedly mounted in their corresponding holes. Each optical fiber holder 24 comprises a hollow-cylindrical holder body 24, a body fixing screw 25 and an optical fiber fixing screw 26. In the optical fiber holders 24, the holder bodies 24 are inserted into their corresponding holes defined in the probe base 23 and thereafter tightened and fixed to the probe base 23 with the body fixing screws 25. Besides, incident optical fibers or detection optical fibers are inserted into their corresponding central holes of the hold bodies 24 and thereafter fixed with their corresponding optical fiber fixing screws 26 in states in which ends of the optical fibers are in slight contact with the surface of the subject 9.

The present embodiment shows the case in which the number of the measurement channels is 64. It is however needless to say that the embodiment of the present invention is by no means limited to the number of these measurement channels. Incidentally, the present embodiment can be easily applied to a so-called optical computed tomography system of a type wherein data obtained by effecting tomography on an inner living body with light is image-processed by a computer.

According to the present embodiment, an optical measurement instrument for a living body can be obtained which is capable of measuring information about an inner living body as an image within a wide space region with satisfactory efficiency on a time and system basis and providing a small and simple instrument configuration.

<<Second Embodiment>>

Figure 10:
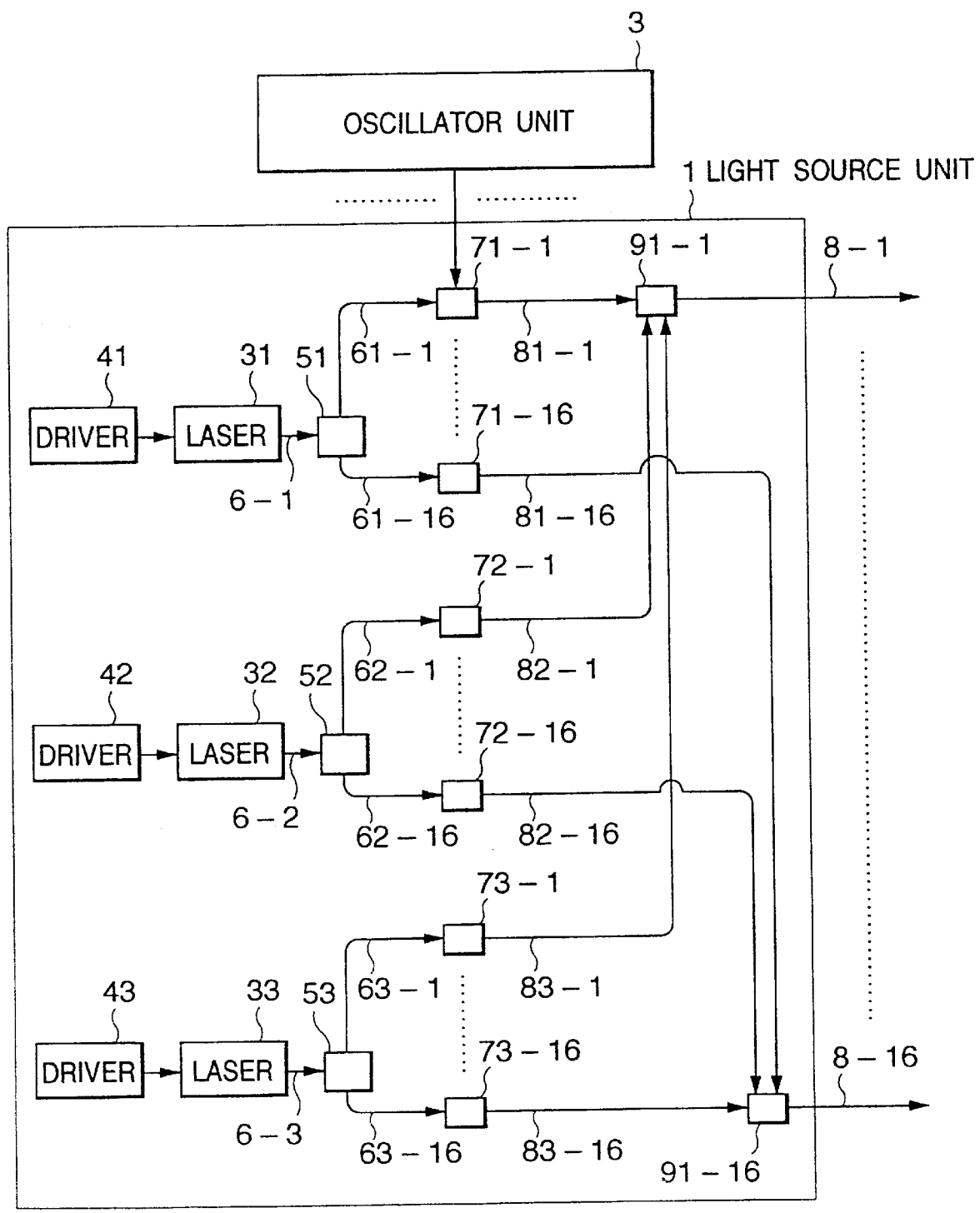
FIG. 10 is a diagram showing a configuration of a light source unit employed in an optical measurement instrument for a living body, according to a second embodiment of the present invention.

FIG. 10 schematically shows a configuration of an optical measurement instrument for a living body, according to a second embodiment of the present invention.

The present embodiment is similar in basic configuration of the measurement system to the first embodiment but different in configuration of the light source unit 1 from the first embodiment. FIG. 10 shows a configuration of a light source unit 1 employed in the second embodiment.

A light source having a wavelength of 770 nm, e.g., a semiconductor laser or laser diode 31 is driven by a laser driver circuit 41 so as to emit modulation-free continuous light therefrom. The light is introduced into an optical fiber 6-1 and thereafter distributed to sixteen optical fibers 61-1 through 61-16 through an optical fiber coupler 51.

Figure 11:
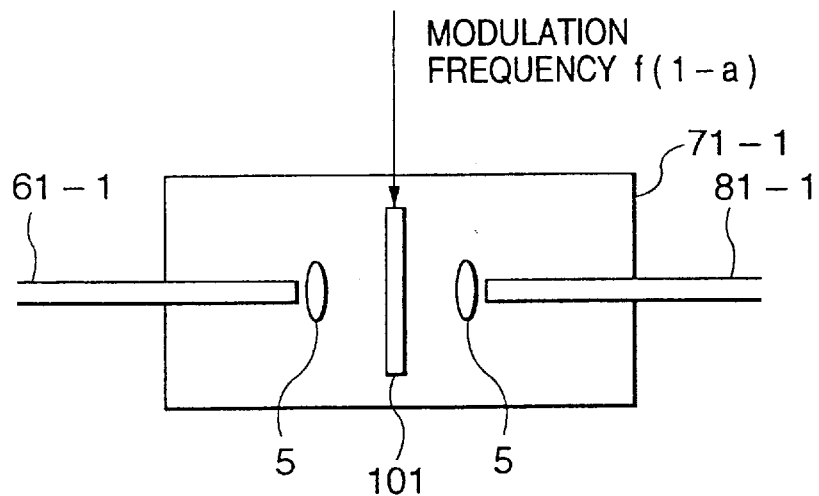
FIG. 11 is a diagram illustrating a specific configuration of a light modulator employed in the embodiment shown in FIG. 10.

The sixteen optical fibers include light modulators 71-1 through 71-16 in their paths, respectively. Configurations of these light modulators will be shown in FIG. 11 by the light modulator 71-1 as an example. For example, a liquid crystal filter 101 is incorporated into the light modulator 71-1. The liquid crystal filter 101 is supplied with a modulation voltage signal produced from an oscillator in an oscillator unit 3 so as to periodically repeat the turning on and off. In the light modulator 71-1, for example, a modulation voltage signal whose modulation frequency is f(1-a), is applied to the liquid crystal filter 101. The light incident from the optical fiber 61-1 is applied to the liquid crystal filter 101 through a lens 5. The light transmitted through the liquid crystal filter 101 is focused through a lens 5 so as to be introduced into an optical fiber 81-1. Now, the light modulators 71-1 through 71-16 are activated such that liquid crystal filters thereof are turned on and off by modulation frequencies different from one another, e.g., f(1-a), f(2-a), . . . and f(16-a). In place of the liquid crystal filter, one using a rotary mechanical light chopper may be used as the light modulator. Thus, the lights modulated with the different modulation frequencies by the light modulators 71-1 through 71-16 are introduced into and transmitted via their corresponding optical fibers 81-1 through 81-16.

Similarly, light sources (laser diodes having wavelengths of 805 nm and 830 nm, for example) 32 and 33 having other wavelengths in the light source unit 1 are respectively driven by laser driver circuits 42 and 43. Lights outputted from the light sources 32 and 33 are respectively transmitted to optical fiber couplers 52 and 53 through optical fibers 6-2 and 6-3 from which the lights are distributed to sixteen optical fibers 62-1 through 62-16 and sixteen optical fibers 63-1 through 63-16 respectively. The lights distributed to the optical fibers 62-1 through 62-16 and 63-1 through 63-16 are respectively modulated with different modulation frequencies by light modulators 72-1 through 72-16 and 73-1 through 73-16. Namely, modulation signals whose modulation frequencies are f(1-b), f(2-b), . . . and f(16-b) different from one another, are applied to their corresponding light modulators 72-1 through 72-16. Further, modulation signals whose modulation frequencies are f(1-c), f(2-c, . . . and f(16-c) different from one another, are applied to their corresponding light modulators 73-1 through 73-16. The lights, which have passed through the light modulators 72-1 through 72-16, are introduced into and transmitted through their corresponding optical fibers 82-1 through 82-16. Further, the lights transmitted through the light modulators 73-1 through 73-16 are introduced into and transmitted through their corresponding optical fibers 83-1 through 83-16.

Thus, the forty-eight types of lights in total different in modulation frequency from one another, which have been modulated individually by the total of forty-eight light modulators 71-1 through 71-16, 72-1 through 72-16 and 73-1 through 73-16 and individually introduced into and transmitted through the total of forty-eight optical fibers 81-1 through 81-16, 82-1 through 82-16 and 83-1 through 83-16, are next collected every wavelengths in the following instructions or directions and introduced into respective one optical fibers (sixteen optical fibers in total). Namely, the lights transmitted through the optical fibers 81-1, 82-1 and 83-1 are collectively introduced into a single incident optical fiber 8-1 through an optical fiber coupler 91-1. Similarly, the lights transmitted through the optical fibers 81-16, 82-16 and 83-16 are collectively introduced into a single incident optical fiber 8-16 through an optical fiber coupler 91-16.

Thus, the three types of lights (forty-eight types of lights in total) different in wavelength and modulation frequency from one another are applied to the surface of the subject 9 by the sixteen incident optical fibers 8-1 through 8-16 in a manner similar to the aforementioned first embodiment. Incidentally, a method of measuring light reflected from the subject 9 is similar to that employed in the first embodiment.

According to the present embodiment, an optical measurement instrument for a living body can be obtained which is capable of measuring information about an inner living body as an image within a wide spatial region with satisfactory efficiency on a time and system basis and providing a small and simple instrument configuration.

<<High Sensitive Measurement for Information on Deep Tissue>>

The present invention provides an optical measurement instrument for a living body, which is capable of measuring information on a small region at a depth in a subject (living body) with high sensitivity and high resolution.

An optical measurement instrument for a living body, which irradiates the living body with visible-infrared region light and detects light reflected from a depth region in the living body, spaced by about 10 to 50 mm from an incident position to thereby obtain living-body information on the deep tissue region, has heretofore been disclosed in, for example, Japanese Patent Application Laid-Open Nos. 63-277038 and 5-300887. This type of conventional instrument, however, encounters difficulties in obtaining the living-body information about the small region at the depth in the living body with sufficient accuracy of measurement.

Namely, since incident light is greatly diffused into the living body due to a strong light scattering character (scattering coefficient=about 1.0 [1/mm] or so) in the living body upon living body measurement using the light, information over a wide range in the living body is contained in the result of measurement. In particular, a spatial dependence on detection sensitivity presents a problem in that the sensitivity of shallow tissue near a light incident position and a light detection position becomes greater than that of deep tissue. Therefore, the conventionally-proposed method encounters difficulties in measuring a concentration change of a light-absorption substance in a deep tissue region with satisfactory accuracy. When a change of hemo-dynamics of a brain is measured from above the scalp, a problem arises in that due to the above reason, the change of hemo-dynamics in a relatively shallow region just below the scalp greatly reflects on a measured value.

Figure 12:
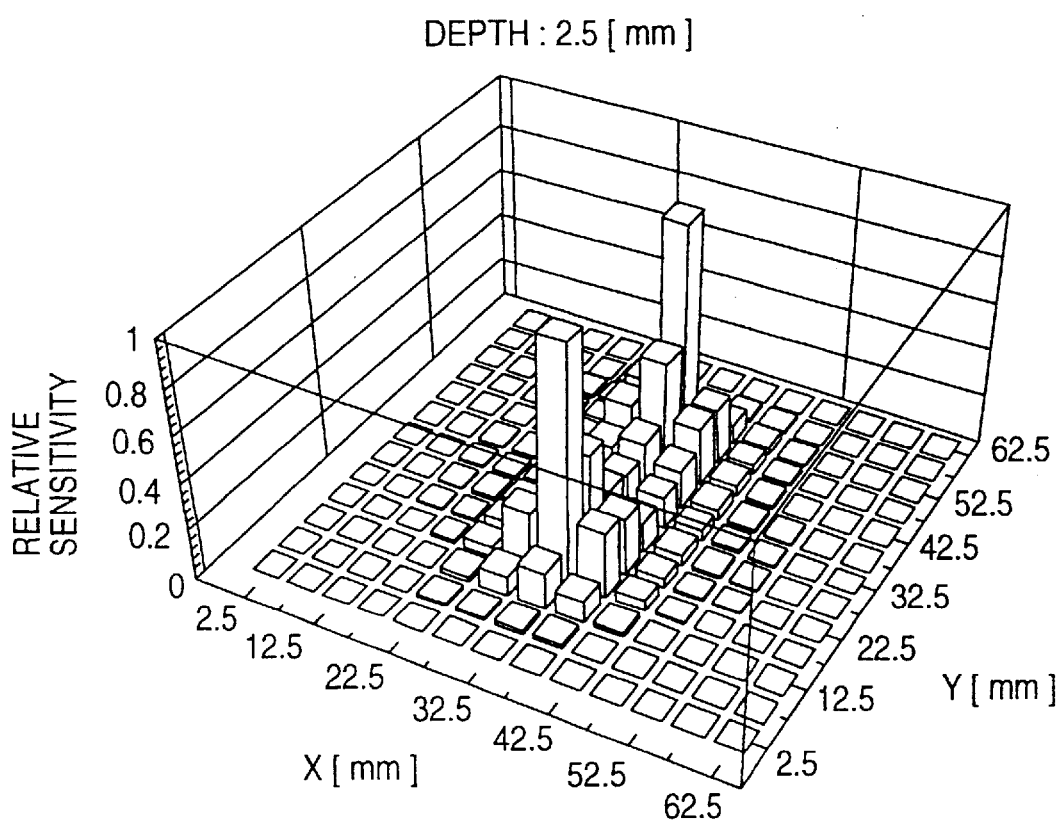
FIGS. 12, 13 and 14 are respectively diagrams showing the relationship between measurement sensitivity distributions and depths in living body at inner living body measurements by the prior art.
Figure 13:
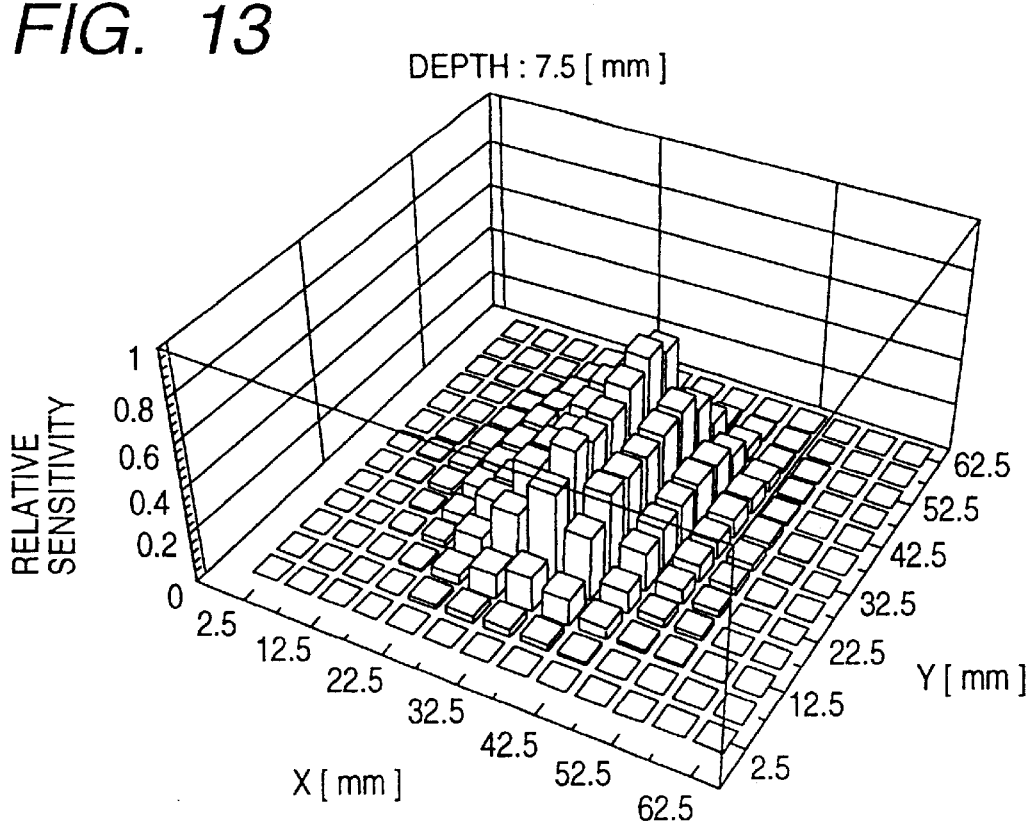
Figure 14:
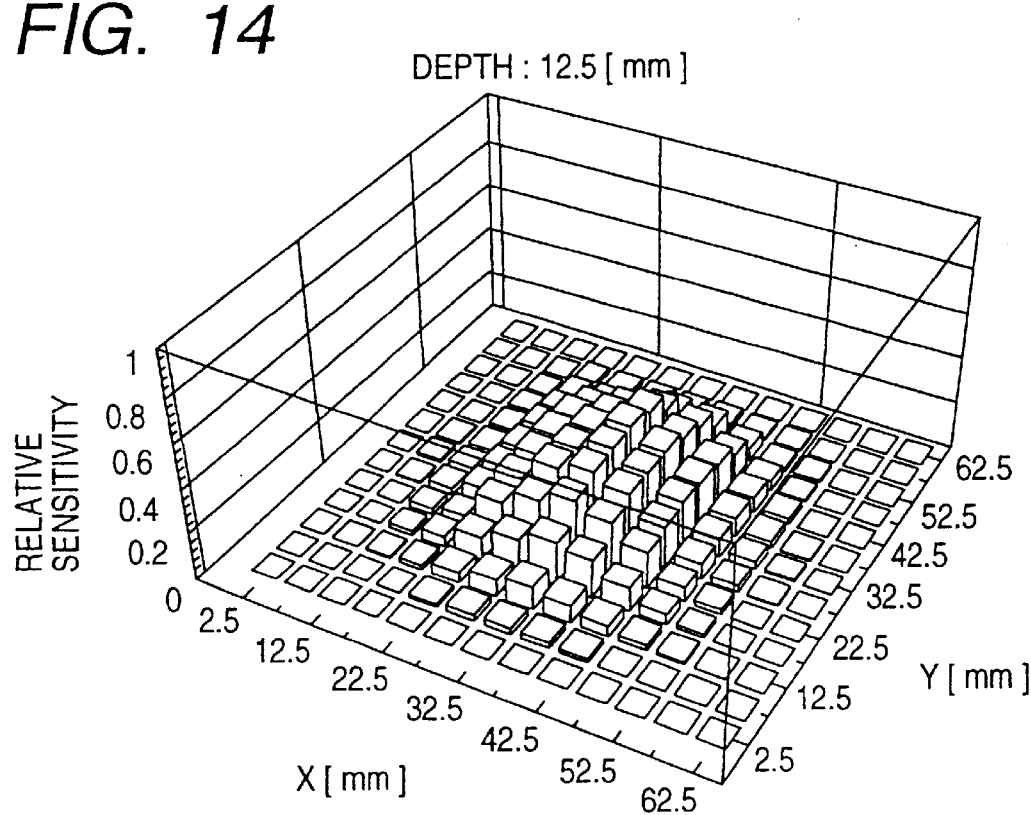

Examples of results obtained by determining relative sensitivity distributions about concentration changes of a light-absorption substance in a living body, using the above-described prior art are shown in FIGS. 12 through 14. In the examples, the surface of the living body is regarded as a plane and a plane parallel to the surface of the living body is defined as an X-Y plane. Further, light is applied to the inner living body from a position represented by x=32.5 mm and y=17.5 mm on the surface of the living body. The applied light is focused at a position represented by x=32.5 mm and y=47.5 mm, which is spaced by 30 mm from a light incident position. In such a case, a relative sensitivity distribution obtained at a 2.5 mm-depth position, a relative sensitivity distribution obtained at a 7.5 mm-depth position and a relative sensitivity distribution obtained at a 12.5 mm-depth position are shown in FIGS. 12, 13 and 14 respectively. It is understood from these drawings that although the relative sensitivity distribution in the surface tissue region (FIG. 12) is highly steep, whereas the relative sensitivity distribution in the deep tissue region (FIG. 14) is low dulled. Thus, the influence of light absorption and scattering in the surface tissue region becomes very large. Accordingly, the prior art encounters difficulties in measuring the concentration change of the light-absorption substance in the deep tissue region with high accuracy.

Thus, the present invention is constructed in such a manner that when an inner living body is irradiated with lights from a plurality of light incident positions on the surface of a subject and the lights transmitted through the subject are focused and detected at a plurality of light detection positions on the surface of the subject, the relationship of placement between the plurality of light incident positions and the plurality of light detection positions is set or established so that optical paths of the lights (transmitted lights) irradiated or incident from the plurality of light incident positions and transmitted through the subject overlap each other in a desired measurement region in the subject, and light detection signals obtained at the plurality of light detection positions are arithmetically processed, thereby improving detection sensitivity with respect to optical information within the desired measurement region (relatively reducing detection sensitivity with respect to optical information on regions other than the desired measurement region).

The aforementioned characteristic configurations of the present invention will be described below in more details.

An optical measurement instrument for a living body, according to the present invention, which is used for measuring information on a deep subject (living body), basically comprises light incident means having a plurality of incident portions or units for irradiating an inner subject with a plurality of incident lights different in wavelength from one another from a plurality of incident positions on the surface of the subject, collecting light means having a plurality of light gathering or collecting portions or units for collecting lights (transmitted lights) irradiated or incident from the plurality of light incident positions and transmitted through the subject at a plurality of detection positions on the surface of the subject, said units being provided in such a layout relationship that optical paths of the lights (transmitted lights) incident from the plurality of incident units and transmitted through the subject overlap each other in a predetermined measurement region in the subject, light detection means having a plurality of optical detection portions or units for detecting intensities every plural incident positions and plural wavelengths, of the transmitted lights collected by the plurality of light collecting units, and signal processing means for performing signal processing for improving measurement sensitivity with respect to optical information on the predetermined measurement region in the subject or reducing measurement sensitivity with respect to optical information on regions other than the predetermined measurement region to thereby obtain the optical information on the predetermined measurement region from light intensity detection signals produced from the plurality of optical detection units.

The light intensities of the transmitted-light components every incident positions and wavelengths may be obtained by giving intensity modulation to the plurality of incident lights with modulation frequencies different every incident positions and wavelengths and separating and detecting only the light components intensity-modulated with predetermined modulation frequencies from the transmitted lights collected by the light collecting units or by arithmetically processing the detection signals of the transmitted lights collected by the light collecting units. Further, the light intensities of the transmitted-light components every incident positions and wavelengths may be obtained by spectroscopically measuring the transmitted lights collected by the light collecting units with spectroscopes every wavelengths and separating and detecting (lock-in detecting) only light components intensity-modulated with predetermined modulation frequencies from the spectroscopically-measured respective wavelength components. Here, the above optical information to be measured corresponds to an absorption coefficient in the subject (living body).

In the present invention, a photoelectric conversion unit for photoelectrically converting transmitted light (or transmitted light of a predetermined wavelength having a predetermined intensity modulation frequency) having a predetermined intensity modulation frequency into a transmitted light intensity signal having the predetermined intensity modulation frequency and a phase sensitive detection unit supplied with the transmitted light intensity signal produced from the photoelectric conversion unit are used. Reference signals corresponding to intensity modulation frequencies applied to incident lights of wavelengths from their corresponding incident positions are inputted to the phase sensitive detection unit, so that a signal corresponding to the intensity of a transmitted light component with a predetermined intensity modulation frequency can be outputted from the phase sensitive detection unit. Alternatively, the photoelectric conversion unit and an A/D (analog-to-digital) converter supplied with the transmitted light intensity signal from the photoelectric conversion unit are used. The transmitted light intensity signal produced from the photoelectric conversion unit is inputted to the A/D converter to determine a transmitted light intensity signal in a frequency space by Fourier transformation. Further, a signal corresponding to an intensity modulation frequency given for each predetermined incident position or predetermined wavelength is inputted to the A/D converter to determine a predetermined reference frequency by Fourier transformation. A signal component of a frequency equal to the predetermined reference frequency is determined by computation from the transmitted light intensity signal in the frequency space. This may be used as an intensity signal having a transmitted light component with a predetermined intensity modulation frequency.

The plurality of incident units and the plurality of light collecting units can be disposed in such a manner that vertical lines or perpendiculars (corresponding to straight lines normal to the surface of the subject) substantially passing through the center of the predetermined measurement region are placed on at least one circle having a predetermined diameter at equal intervals with a point intersecting the surface of the subject as the center and the respective one incident units and the respective one light collecting units are respectively set as pairs and placed in a point symmetrical position relationship with the center of the circle as a point symmetrical center. In this case, arithmetic or signal processing is performed for detecting transmitted light intensities corresponding to incident lights every wavelengths from respective light incident positions every light collecting positions and every wavelengths, selecting transmitted light intensities incident every wavelengths from the light incident positions positionally symmetric with respect to their corresponding light collection positions from the transmitted light intensities incident every wavelengths from the respective light incident positions, selecting the transmitted light intensities detected on the same circle from the selected transmitted light intensities, and effecting multiplication or integrating processing on intensities of transmitted lights having predetermined wavelengths, which have been detected on the same circle. Further, a transmitted light intensity arithmetic process is performed by using intensities of transmitted light collected by the light collecting units placed on the circle small in diameter as information from a shallow portion in the subject and utilizing intensities of transmitted light collected by the light collecting units placed on the circle large in diameter as information from a deep portion in the subject.

Further, the plurality of incident units and the plurality of light collecting units can be disposed in square lattice form. In this case, the incident units and light collecting units are respectively placed on nodes of respective rows of the square lattices so that the rows along which the incident units are placed and the rows along which the light collecting units are placed, are provided in an alternating sequence. Moreover, the plurality of incident units and the plurality of light collecting units can be disposed in regular hexagonal lattice form. In this case, the incident units and the light collecting units are alternately disposed on respective nodes of the regular hexagonal lattice.

As light to be applied to the subject (living body), light having a wavelength near 805nm is used. An oxyhemoglobin concentration change in the living body, a deoxyhemoglobin concentration change in the living body, and a total hemoglobin concentration change computed as the sum of the oxyhemoglobin concentration change and the deoxyhemoglobin concentration change are determined from the intensity of the transmitted light. A time variation in the total hemoglobin concentration change can be displayed. The total hemoglobin concentration change may be determined directly from the transmitted light intensity. As the lights to enter into the subject (living body), incident lights having a plurality of wavelengths (at least two wavelengths) ranging from 700 nm to 1100 nm can be used.

Time variations in the total hemoglobin concentration change computed as the sum of the aforementioned oxyhemoglobin concentration change and deoxyhemoglobin concentration change, and the oxyhemoglobin concentration change or the deoxyhemoglobin concentration change can be respectively represented in the form of lines (graphs) by changing the color, type or thickness or the like of each line. For example, the oxyhemoglobin concentration change may be displayed with the red or pink, the deoxyhemoglobin concentration change may be displayed with the blue, dark blue or green, and the total hemoglobin concentration change may be displayed with the black or brown. Further, images corresponding to the total hemoglobin concentration change computed as the sum of the oxyhemoglobin concentration change and the deoxyhemoglobin concentration change, and the oxyhemoglobin concentration change or the deoxyhemoglobin concentration change may be represented in the form of colors or intensities corresponding to their concentration changes. When each concentration change is positive, the images may be represented with a dark red color or a high intensity as the absolute value of the value of the concentration change increases. On the other hand, when the concentration change is negative, the images may be represented with a dark blue color or a low intensity as the absolute value of the value of the concentration change decreases.

When the plurality of incident units and the plurality of light collecting units are placed on the same circle, the intensities of transmitted lights having predetermined wavelengths, which have been detected on the circle, can be arithmetically processed with the total hemoglobin concentration change computed as the sum of the oxyhemoglobin concentration change and the deoxyhemoglobin concentration change, and the oxyhemoglobin concentration change or the deoxyhemoglobin concentration change in a predetermined range region of a predetermined depth in the subject on perpendiculars normal to the surface of the subject or a predetermined range region of a predetermined rotor with each perpendicular as the axis of rotation being regarded as reflected. In this case, the diameter of the circle can be set so as to fall within a range from 25 mm to 35 mm and the depth thereof can be set so as to fall within a range from 12 mm to 25 mm. Further, the covering of the surfaces of the incident units or light collecting units, which make contact with the surface of the subject, with members flexible and high permeable into the incident light allows the incident units or light collecting units to lessen irritation to the subject.

Thus, the plurality of incident units and the plurality of light collecting units are placed on the circle having the predetermined diameter so that the optical paths in the subject, of the lights incident from the plurality of incident units overlap each other, only the transmitted lights corresponding to the lights incident from the incident units located in the positions opposed to the respective light collecting units are selectively detected, and the intensities of the transmitted lights detected by their corresponding light collecting units are subjected to multiplication. As a result, the measurement sensitivity in the region (region to be measured) located in the predetermined deep position inside the subject as seen from the central position of the circle on the surface of the subject can be improved.

According to the present invention, as has been already described above, since a plurality of measurement channels formed between a plurality of light incident positions and a plurality of light detection positions can be measured simultaneously and without crosstalk, the plurality of pairs of light incident positions and detection positions are disposed on the circumference surrounding specific measured portions at deep positions in a living body and the middle positions (measurement positions) of the respective pairs of light incident and detection positions are caused to coincide with the specific measured portions, so that only information about the specific measured portions can be selectively and concentratedly detected. Thus, the living body information on the specific portion at the deep position in the subject can be measured with high sensitivity.

<<Third Embodiment>>

An optical measurement instrument for a living body, according to a third embodiment of the present invention, which is suitable for use in the measurement of information on deep tissue, will hereinafter be described.

In the present embodiment, two types of lights (lights of two wavelengths) different in wavelength from each other are used as incident lights with the objective of measuring oxy- and deoxy-hemoglobin concentration changes in a subject (living body). Further, the number of light incident positions and the number of light detection positions are set to two respectively. It is however easy to further increase the number of these incident lights (number of wavelengths), the number of the light incident positions and the number of the light detection positions. It is needless to say that with the increase in the number of the incident lights (number of wavelengths), light-absorption substance concentration changes in other living bodies such as cytochrome, myoglobin, etc. can be measured as well as the oxy- and deoxy-hemoglobin concentration changes.

Figure 15:
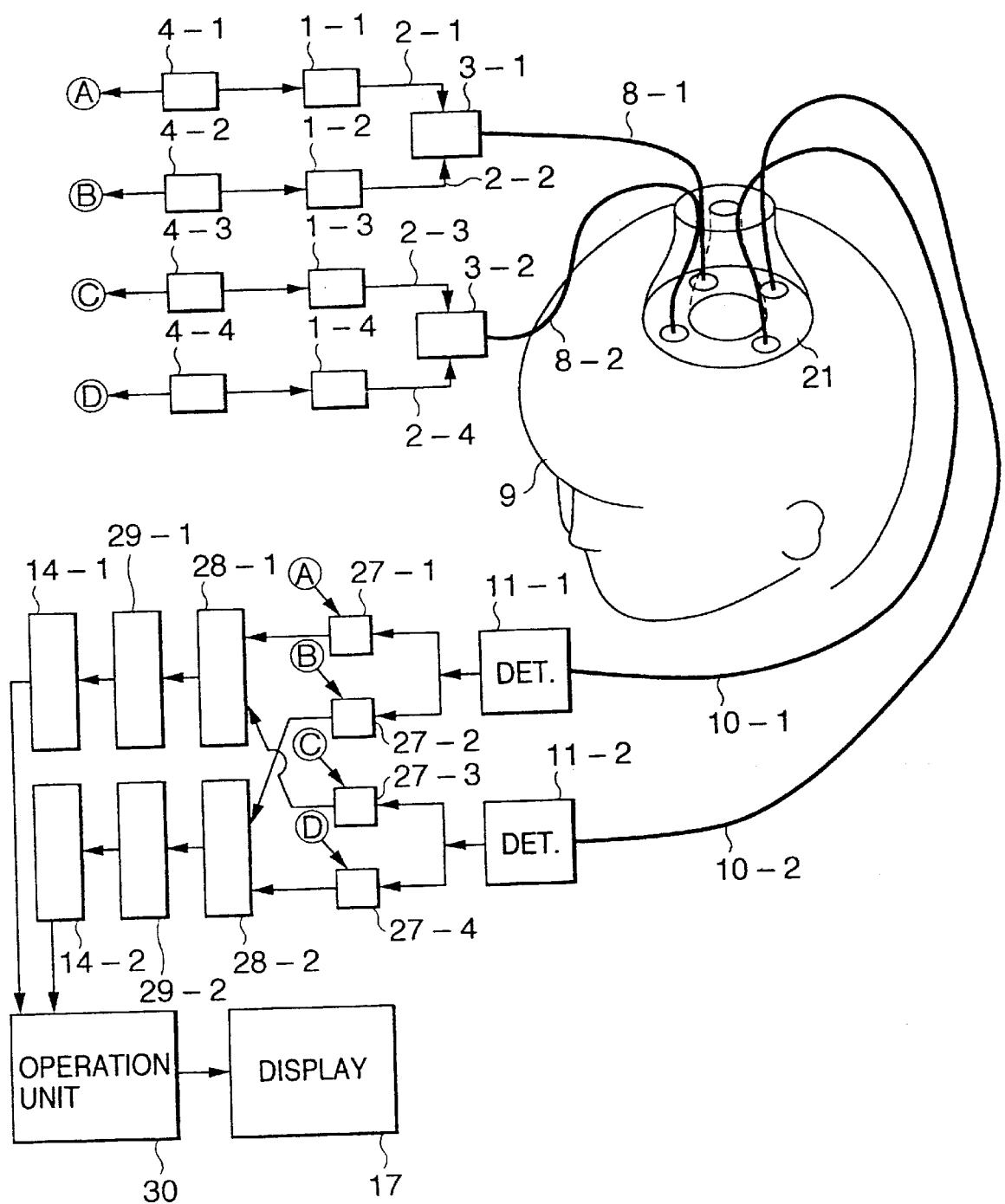
FIG. 15 is a diagram schematically showing a configuration of an optical measurement instrument for a living body, according to a third embodiment of the present invention.

FIG. 15 shows a schematic configuration of the optical measurement instrument for the living body, according to the present embodiment.

Output lights emitted from a plurality of light sources 1-1, 1-2, 1-3 and 1-4 (four light sources in the present embodiment) are introduced into their corresponding incident optical fibers 2-1, 2-2, 2-3 and 2-4. Here, the wavelengths of the output lights emitted from the light sources 1-1 and 1-3 are represented as λ1 and the wavelengths of the output lights emitted from the light sources 1-2 and 1-4 are represented as λ2. Incidentally, the wavelengths λ1 and λ2 are selected from within wavelengths ranging from 400 nm to 2400 nm. Particularly when hemo-dynamics in the living body are measured, the wavelengths may preferably be selected from within wavelengths ranging from 700 nm to 1100 nm so that the difference therebetween falls within 50 nm. Further, the output lights emitted from the light sources 1-1, 1-2, 1-3 and 1-4 are respectively intensity-modulated with mutually-different modulation frequencies f1, f2, f3 and f4 falling between 100 Hz and 10 MHz by their corresponding light-source driver circuits 4-1, 4-2, 4-3 and 4-4. Modulation frequency signals A, B, C and D outputted from the respective light-source driver circuits 4-1, 4-2, 4-3 and 4-4 are inputted to their corresponding phase sensitive detectors 27-1, 27-2, 27-3 and 27-4 as reference frequency signals.

The optical fibers 2-1 and 2-2 are electrically connected to an optical coupler 3-1. Further, the optical fibers 2-3 and 2-4 are electrically connected to an optical coupler 3-2. The lights emitted from the light sources 1-1 and 1-2 are mixed together in the optical coupler 3-1, which in turn is introduced into an incident optical fiber 8-1. The lights emitted from the light sources 1-3 and 1-4 are mixed together in the optical coupler 3-2, which in turn is introduced into an incident optical fiber 8-2. The incident optical fibers 8-1 and 8-2 and detection optical fibers 10-1, 10-2 are fixed by an optical fiber holder 21 and brought into contact with the surface of a subject (human head) 9.

The subject 9 is irradiated with the lights from the incident optical fibers 8-1 and 8-2, and the detection optical fibers 10-1 and 10-2 collect lights (transmitted lights) that have passed through the subject 9. Here, the incident optical fibers 8-1 and 8-2 and the detection optical fibers 10-1 and 10-2 are placed on the circumference of one circle set on the optical fiber holder 21 at equal intervals. The detection optical fibers 10-1 and 10-2 are respectively disposed at positions where they are opposed to the incident optical fibers 8-1 and 8-2 with the center of the circle interposed therebetween. The optical fiber holder 21 may preferably be formed of a black material or covered therewith to obtain high lightproofness or impenetration and be shaped in the form of such a hollow structure as shown in the drawing. The incident optical fibers 8-1 and 8-2 and the detection optical fibers 10-1 and 10-2 may preferably be constructed so that their surface portions other than the surfaces brought into contact with the subject 9 are covered with black materials. It is further desirable to apply coatings composed of a material such as a vinyl resin or the like flexible and having good permeability to the incident light onto the surfaces of the incident optical fibers 8-1 and 8-2 and detection optical fibers 10-1 and 10-2, which make contact with the subject 9 with the objective of lessening a stimulus against the subject 9 due to their contact with the subject 9.

The transmitted lights collected by the detection optical fibers 10-1 and 10-2 are respectively introduced into the optical detectors 11-1 and 11-2 where they are photoelectrically converted and detected. As the optical detectors 11-1 and 11-2, a photomultiplier tube or an avalanche photodiode is used. An output signal delivered from the optical detector 11-1 is divided into two, which in turn are inputted to phase sensitive detectors 27-1 and 27-2 respectively. An output signal delivered from the optical detector 11-2 is also divided into two, which in turn are respectively inputted to phase sensitive detectors 27-3 and 27-4.

The signals inputted to the phase sensitive detectors 27-1, 27-2, 27-3 and 27-4 are respectively mixed with transmitted light intensity signals of lights of all wavelengths, which fall into the subject (living body). However, since the phase sensitive detectors 27-1, 27-2, 27-3 and 27-4 are supplied with the reference frequency signals A, B, C and D outputted from the light-source driver circuits 4-1, 4-2, 4-3 and 4-4, only a transmitted light intensity component corresponding to the incident light having the wavelength λ1 and the modulation frequency f1, which is outputted from the light source 1-1, is separated and detected from the phase sensitive detector 27-1, only a transmitted light intensity component corresponding to the incident light having the wavelength λ2 and the modulation frequency f2, which is outputted from the light source 1-2, is separated and detected from the phase sensitive detector 27-2, only a transmitted light intensity component corresponding to the incident light having the wavelength λ1 and the modulation frequency f3, which is outputted from the light source 1-3, is separated and detected from the phase sensitive detector 27-3, and only a transmitted light intensity component corresponding to the incident light having the wavelength λ2 and the modulation frequency f4, which is outputted from the light source 1-4, is separated and detected from the phase sensitive detector 27-4.

The transmitted light intensity signal components having the wavelength λ1, which have been detected by the phase sensitive detectors 27-1 and 27-3, are inputted to a multiplier 28-1 where both signal components are subjected to multiplication. The transmitted light intensity signal components having the wavelength λ2, which have been detected by the phase sensitive detectors 27-2 and 27-4, are inputted to a multiplier 28-2 where both signal components are subjected to multiplication. Signals outputted from the multipliers 28-1 and 28-2 are inputted to logarithm amplifiers 29-1 and 29-2 respectively. Further, signals outputted from the logarithm amplifiers 29-1 and 29-2 are respectively inputted to A/D (analog-to-digital) converters 14-1 and 14-2 where they are converted into digital signals, which in turn are taken in an operation unit 30.

Based on the taken-in time-sequence signals having the transmitted light intensities of two wavelengths, the operation unit 30 computes an oxyhemoglobin concentration change, a deoxyhemoglobin concentration change, and the sum of the oxyhemoglobin concentration change and the deoxyhemoglobin concentration change, which indicates the volume of blood. The result of computation by the operation unit 30 is displayed on a display device 17 as a time-sequence change graph. When the multiposition measurement (measurement on a plurality of measurement regions in the subject 9) is made by a similar device, the result of measurement can be displayed on the display device 17 as an image.

When the respective hemoglobin concentration changes are represented as time-sequence change graphs, the display device 17 changes display colors every hemoglobin concentration change graphs if color-displayable, and thereby can display the hemoglobin concentration changes thereon, whereas if the display device 17 is color-undisplayable, then the display device 17 can display them thereon by changing the type or thickness or the like of display line every hemoglobin concentration change graphs. For example, when the display device 17 is color-displayable, the oxyhemoglobin concentration change is displayed with the red or pink, the deoxyhemoglobin concentration change is displayed with the blue, dark blue or green, and the total hemoglobin concentration change is displayed with the black, gray or brown. When the result of multiposition measurement is displayed as an image, it may be displayed with an contour-line image. Alternatively, it may be displayed by changing a display color or intensity in association with a change in concentration change value. Further, the result of multiposition measurement may be displayed with the dark red or gray as the absolute value of a positive concentration change value increases, whereas as the absolute value of a negative concentration change value increases, it may be displayed with the dark blue or light white.

As the instrument configuration of the present invention, various modified configurational examples about a data acquisition unit ranging from the optical detectors 11-1, 11-2 to the operation unit 30 shown in FIG. 15 are considered. FIGS. 16 through 20 illustrate these modified configurational examples about the data acquisition unit.

Figure 16:
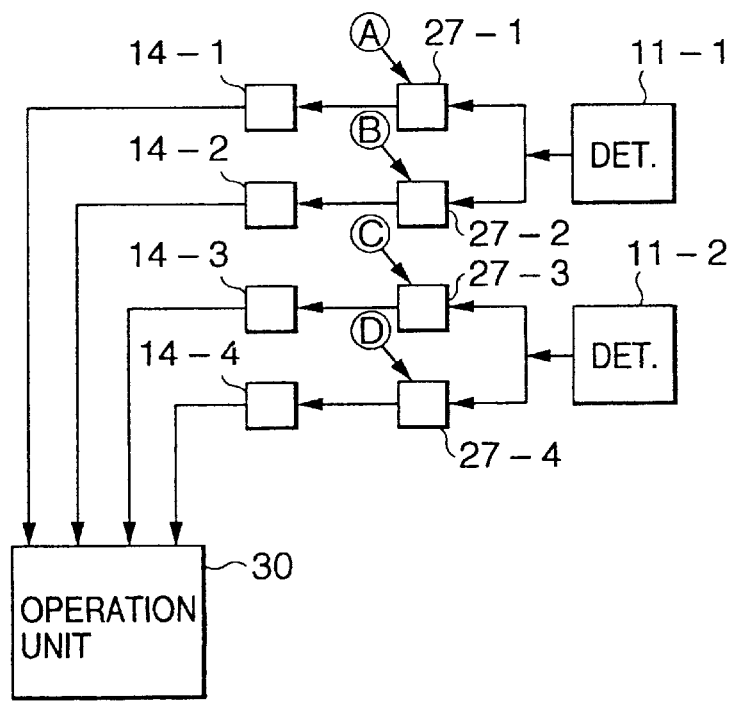
FIG. 16 is a diagram showing another example of a configuration of a data acquisition unit employed in the embodiment shown in FIG. 15.

FIG. 16 shows a first modified configurational example about the data acquisition unit. In the present example, a configuration from light sources 1-1, 1-2, 1-3 and 1-4 to detection optical fibers 10-1 and 10-2 (light incident units and light collecting units) is identical to that shown in FIG. 15 and these portions will be omitted from the drawing for simplification. Incidentally, symbols A, B, C and D enclosed with circles indicate reference frequency signals in the same manner as in FIG. 15. These points are similar even to FIGS. 17 through 20 to be explained later.

The data acquisition unit shown in the present example comprises optical detectors 11-1 and 11-2, phase sensitive detectors 27-1, 27-2, 27-3 and 27-4, A/D converters 14-1, 14-2, 14-3 and 14-4, and an operation unit 30.

A configuration up to the phase sensitive detectors 27-1, 27-2, 27-3 and 27-4 is identical to that shown in FIG. 15. In the present example, however, signals (transmitted light intensity signals) outputted from the phase sensitive detectors 27-1, 27-2, 27-3 and 27-4 are converted into digital signals by the A/D converters 14-1, 14-2, 14-3 and 14-4 respectively, after which they are inputted to the operation unit 30. The operation unit 30 first performs multiplication between the transmitted light intensity signals identical in wavelength, of the input transmitted light intensity signals of all wavelengths. Thereafter, the operation unit 30 performs a natural logarithm operation on the result of multiplication or all of the firstly-inputted transmitted light intensity signals. Further, the operation unit 30 performs addition between the transmitted light intensity signals identical in wavelength with respect to the result of natural logarithm operation. The number of combinations of the transmitted light intensity signals identical in wavelength is two in total, which comprises a combination of the signals outputted from the A/D converters 14-1 and 14-3 and a combination of the signals outputted from the A/D converters 14-2 and 14-4.

Figure 17:
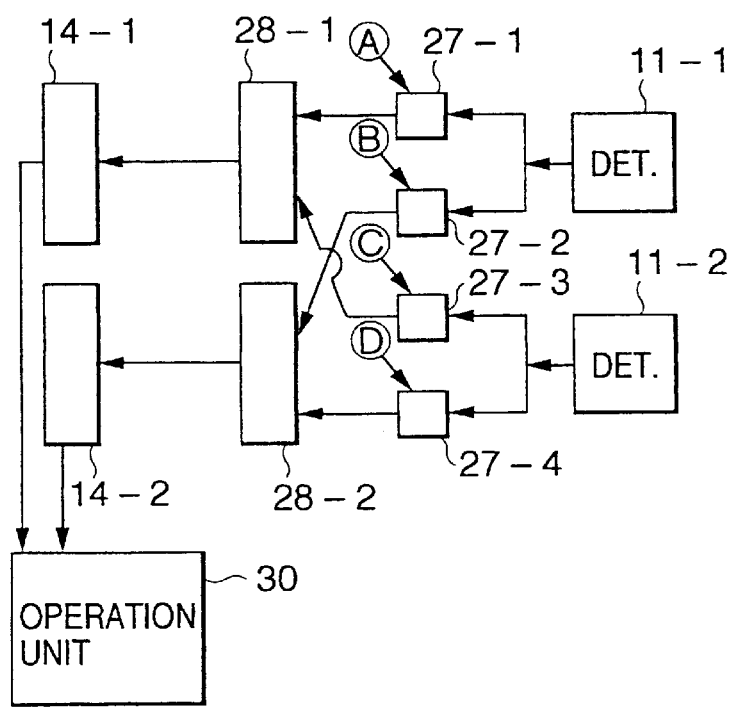
FIG. 17 is a diagram illustrating a further example of the configuration of the data acquisition unit employed in the embodiment shown in FIG. 15.

FIG. 17 shows a second modified configurational example about the data acquisition unit.

The data acquisition unit shown in the present example comprises optical detectors 11-1 and 11-2, phase sensitive detectors 27-1, 27-2, 27-3 and 27 -4, multipliers 28-1 and 28-2, A/D converters 14-1 and 14-2, and an operation unit 30. A configuration up to the multipliers 28-1 and 28-2 is identical to that shown in FIG. 15. In the present example, however, signals outputted from the multipliers 28-1 and 28-2 are respectively converted into digital signals by the A/D converters 14-1 and 14-2, which in turn are inputted to the operation unit 30. The operation unit 30 performs a natural logarithm operation on each of signals outputted from the A/D converters 14-1 and 14-2.

Figure 18:
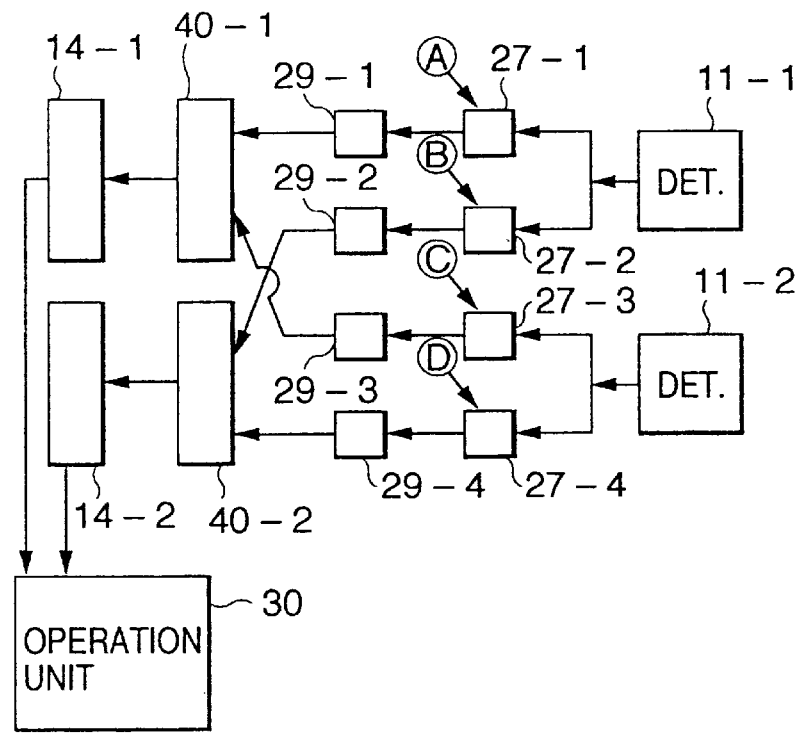
FIG. 18 is a diagram depicting a still further example of the configuration of the data acquisition unit employed in the embodiment shown in FIG. 15.

FIG. 18 shows a third modified configurational example about the data acquisition unit.

The data acquisition unit illustrated in the present example comprises optical detectors 11-1 and 11-2, phase sensitive detectors 27-1, 27-2, 27-3 and 27-4, logarithm amplifiers 29-1, 29-2, 29-3 and 29-4, adders 40-1 and 40-2, A/D converters 14-1 and 14-2, and an operation unit 30. A configuration up to the phase sensitive detectors 27-1, 27-2, 27-3 and 27-4 is identical to that shown in FIG. 15. In the present example, however, signals outputted from the phase sensitive detectors 27-1, 27-2, 27-3 and 27-4 are respectively inputted to the logarithm amplifiers 29-1, 29-2, 29-3 and 29-4 where they are converted into natural logarithm. Transmitted light intensity signals (intensity signals of transmitted lights whose each wavelength is $\lambda 1$) outputted from the logarithm amplifiers 29-1 and 29-3 are inputted to the adder 40-1 where they are added together. Transmitted light intensity signals (intensity signals of transmitted lights whose each wavelength is $\lambda 2$) outputted from the logarithm amplifiers 29-2 and 29-4 are inputted to the adder 40-2 where they are added together. Signals outputted from the adders 40-1 and 40-2 are respectively inputted to the A/D converters 14-1 and 14-2 where they are converted into digital signals, which in turn are inputted to the operation unit 30.

Figure 19:
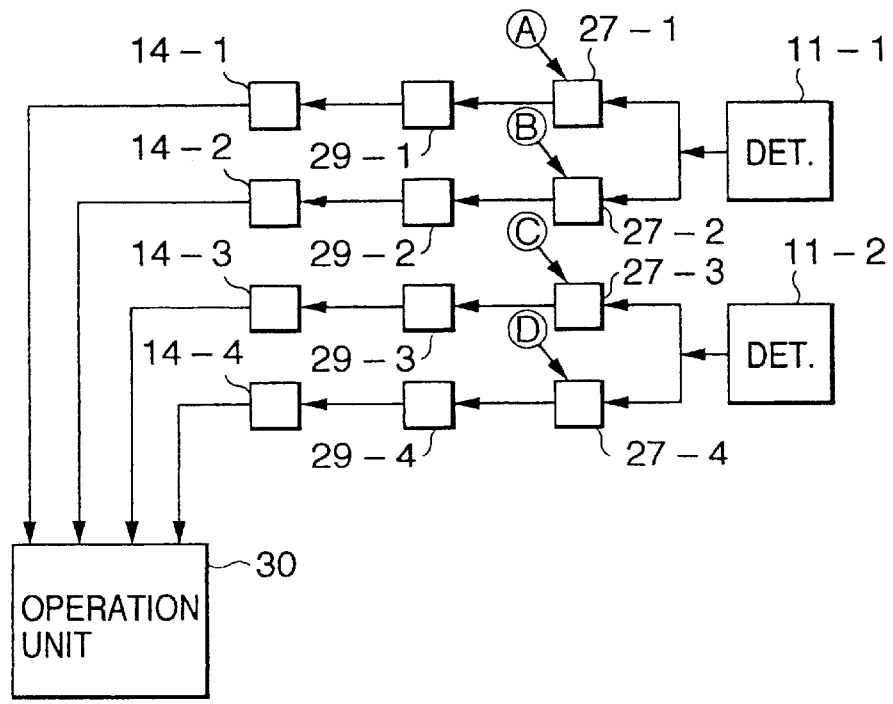
FIG. 19 is a diagram showing a still further example of the configuration of the data acquisition unit employed in the embodiment shown in FIG. 15.

FIG. 19 illustrates a fourth modified configurational example about the data acquisition unit.

The data acquisition unit shown in the present example comprises optical detectors 11-1 and 11-2, phase sensitive detectors 27-1, 27-2, 27-3 and 27-4, logarithm amplifiers 29-1, 29-2, 29-3 and 29-4, A/D converters 14-1, 14-2, 14-3 and 14-4, and an operation unit 30. A configuration up to the phase sensitive detectors 27-1, 27-2, 27-3 and 27-4 is identical to that shown in FIG. 15. In the present example, however, signals outputted from the phase sensitive detectors 27-1, 27-2, 27-3 and 27-4 are respectively inputted to the logarithm amplifiers 29-1, 29-2, 29-3 and 29-4 where they are first converted into natural logarithm. Signals outputted from the logarithm amplifiers 29-1, 29-2, 29-3 and 29-4 are respectively converted into digital signals by the A/D converters 14-1, 14-2, 14-3 and 14-4, which in turn are inputted to the operation unit 30. The operation unit 30 performs addition between the transmitted light intensity signals identical in wavelength, of the input transmitted light intensity signals of all wavelengths. In the present example, the number of combinations of the transmitted light intensity signals identical in wavelength is two in total, which comprises a combination of the signals outputted from the A/D converters 14-1 and 14-3 and a combination of the signals outputted from the A/D converters 14-2 and 14-4.

Figure 20:
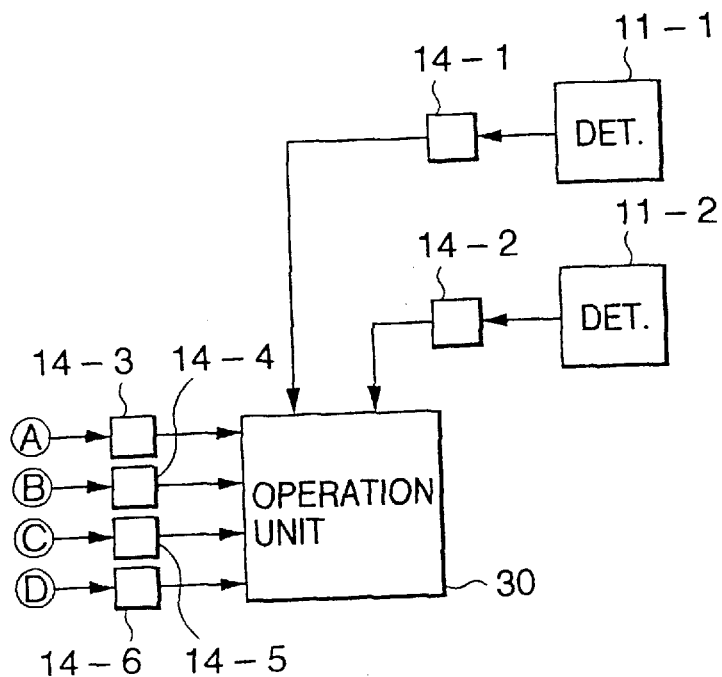
FIG. 20 is a diagram illustrating a still further example of the configuration of the data acquisition unit employed in the embodiment shown in FIG. 15.

FIG. 20 shows a fifth modified configurational example about the data acquisition.

The data acquisition unit shown in the present example comprises optical detectors 11-1 and 11-2, A/D converters 14-1, 14-2, 14-3, 14-4, 14-5 and 14-6, and an operation unit 30. A configuration up to the optical detectors 11-1 and 11-2 is identical to that shown in FIG. 15. In the present example, however, signals outputted from the optical detectors 11-1 and 11-2 are respectively inputted to the A/D converters 14-1 and 14-2 where they are first A/D-converted into digital signals. The signals outputted from the A/D converters 14-1 and 14-2 are inputted directly to the operation unit 30. Further, reference frequency signals (modulation frequency signals of respective incident lights) A, B, C and D are respectively inputted to the A/D converters 14-3, 14-4, 14-5 and 14-6 where they are converted into digital signals. Thereafter, the converted digital signals are inputted to the operation unit 30. The operation unit 30 performs Fourier transformation on the signals inputted thereto from the A/D converters 14-1, 14-2, 14-3, 14-4, 14-5 and 14-6. The frequencies highest in intensity, which have been obtained by performing Fourier transformation on the signals inputted to the operation unit 30 from the A/D converters 14-1, 14-2, 14-3, 14-4, 14-5 and 14-6, are defined as f1, f2, f3 and f4 respectively. Signal intensities corresponding to the frequencies f1 and f2, which are extracted from the signal obtained by Fourier-transforming the signal outputted from the A/D converter 14-1, are respectively defined as I(f1) and I(f2). Further, signal intensities equivalent to the frequencies f3 and f4, which are extracted from the signal obtained by Fourier-transforming the signal outputted from the A/D converter 14-2, are respectively defined as I(f3) and I(f4). Since the signal intensities I(f1) and I(f3) indicate transmitted light intensity signals corresponding to incident lights (corresponding to the lights whose wavelengths are $\lambda 1$, which are emitted from the light sources 1-1 and 1-3 in FIG. 15), both are subjected to mutual multiplication and the result of multiplication is subjected to an natural logarithm operation. Further, the signal intensities I(f2) and I(f4) are also transmitted light intensity signals corresponding to incident lights (corresponding to the lights each having the wavelength of $\lambda 2$, which are emitted from the light sources 1-2 and 1-4 in FIG. 15), both are subjected to mutual multiplication and the natural logarithm operation is performed on the result of multiplication.

Thus, a description has been made of the case in which the two incident optical fibers and the two detection optical fibers have been placed on the circumference of the single circle. However, an optical-fiber layout example in which the incident optical fibers and the detection optical fibers are further disposed in large numbers, will be described below.

Figure 21:
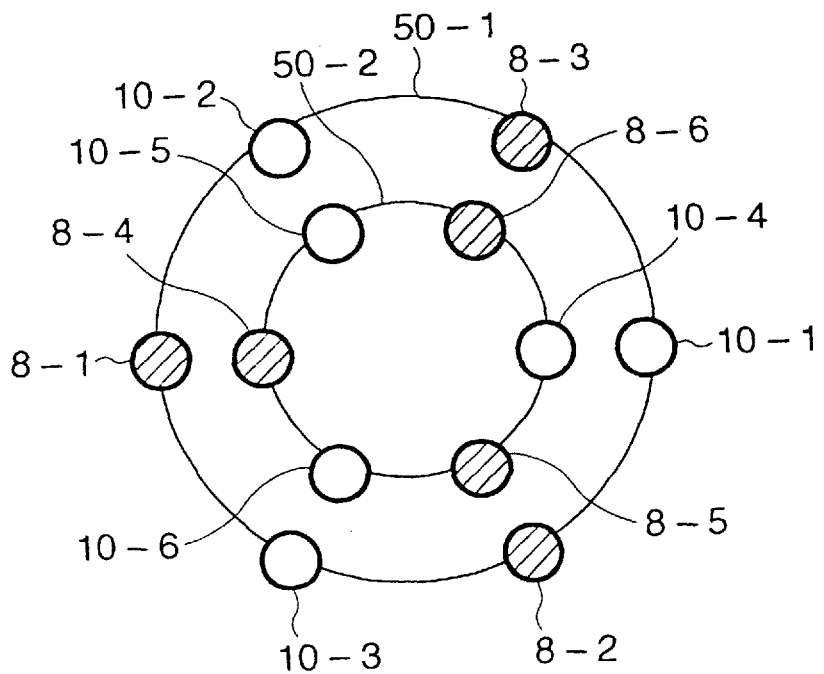
FIG. 21 is a diagram showing another example of the relationship of placement between incident optical fibers and detection optical fibers employed in the embodiment shown in FIG. 15.

FIG. 21 shows a first layout example in which a large number of incident optical fibers and detection optical fibers are laid out. The present layout example shows a case in which the incident optical fibers and the detection optical fibers are respectively disposed on the circumferences of double concentric circles three by three. It is however needless to say that the layout of the incident optical fibers and the detection optical fibers on their corresponding circumferences in larger numbers permits an improvement in the measurement sensitivity to a deep tissue in a subject (living body) and the multiple provision of the concentric circles with the incident optical fibers and the detection optical fibers disposed thereon makes it possible to improve measurement sensitivity at various depth positions in the subject (living body).

Referring to FIG. 21, incident optical fibers 8-1, 8-2 and 8-3 are disposed on the circumference of a circle 50-1 outside double concentric circles at equal intervals every 120 degrees. Detection optical fibers 10-1, 10-2 and 10-3 are respectively placed in positions where they are respectively opposed to the incident optical fibers 8-1, 8-2 and 8-3 on the same circumference. Further, incident optical fibers 8-4, 8-5 and 8-6 are disposed on the circumference of a circle 50-2 inside the double concentric circles at equal intervals every 120 degrees. Detection optical fibers 10-4, 10-5 and 10-6 are respectively placed in positions where they are respectively opposed to the incident optical fibers 8-4, 8-5 and 8-6 on the same circumference. All the (six) optical fibers are fixed to and held by an optical fiber holder 21 similar to that shown in FIG. 15 in a state in which the above layout relationship is held. Owing to the utilization of such an optical fiber layout configuration, a hemoglobin concentration change in deep tissue can be determined by assigning transmitted light intensities detected on the circumference of the outer circle 50-1 for information on the deep tissue and arithmetically processing or computing them, and a hemoglobin concentration change in shallow tissue can be determined by assigning transmitted light intensities detected on the circumference of the inner circle 50-2 for information on the shallow tissue and computing them.

Further, the subtraction of a hemoglobin concentration change obtained by multiplying the hemoglobin concentration change determined by computation from the transmitted light intensities detected on the circumference of the inner circle 50-2 by a predetermined weighting coefficient estimated from a sensitivity distribution from the hemoglobin concentration change determined by computation from the transmitted light intensities detected on the circumference of the outer circle 50-1 makes it also possible to further improve the relative sensitivity of the deep tissue to the shallow tissue.

Figure 22:
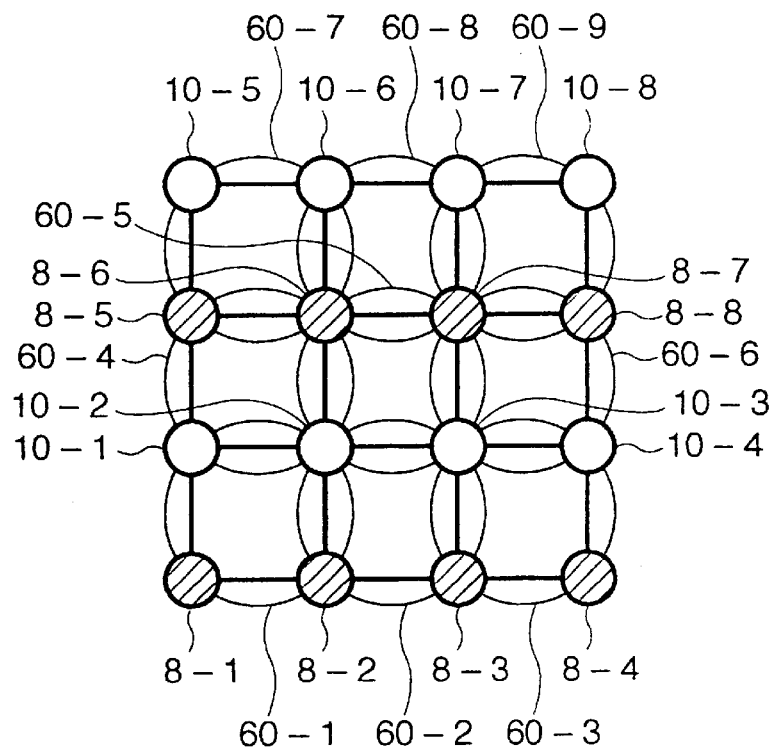
FIG. 22 is a diagram illustrating a further example of the relationship of placement between the incident optical fibers and the detection optical fibers employed in the embodiment shown in FIG. 15.

FIG. 22 shows a second layout configurational example in which a large number of incident optical fibers and detection optical fibers are disposed. Here, the layout of more efficient optical fibers at the time that various positions to be measured in a subject (living body) are measured based on the present invention, will be described. In the present example, respective incident-detection optical fiber pairs or sets each composed of two pairs of incident and detection optical fibers disposed on the circumferences of respective one circles are respectively defined as basic fiber units. The basic fiber units are placed side by side in plural units so as to match the expansion of a desired measurement region.

When a measurement region is expanded with a incident-detection optical fiber pair composed of two pair of incident and detection optical fibers disposed on the circumference of one circle being regarded as the basic fiber unit, the incident optical fibers and detection optical fibers are disposed on respective nodes of each square lattice and the incident optical fibers and the detection optical fibers are alternately disposed in the diagonal directions of the square lattice, as shown in FIG. 22. In the present example, the number of the measurement positions is 9 and nine circles 60-1 through 60-9 are provided around the respective measurement positions. Further, incident optical fibers 8-1 through 8-8 and detection optical fibers 10-1 through 10-8 are placed on the circumferences of the above circles and on the nodes of the square lattices. Owing to such an optical fiber layout, the incident optical fibers and the detection optical fibers disposed on points where the respective adjacent circles intersect, function over the number of the measurement positions identical to the number (four at nodes inside the lattice) of the circles intersecting each other at the nodes at which they are disposed. Therefore, the measurement positions can be measured with the less-reduced number of optical fibers. Although the number of the measurement positions is nine in the present example, it is easy to further increase the number of the measurement positions (i.e., the number of the circles and the number of the nodes) with a view toward carrying out a measurement on a wider measurement region. An image of hemo-dynamics at a deep tissue can be obtained from the result of measurement obtained by the widening of the measurement region.

Figure 23:
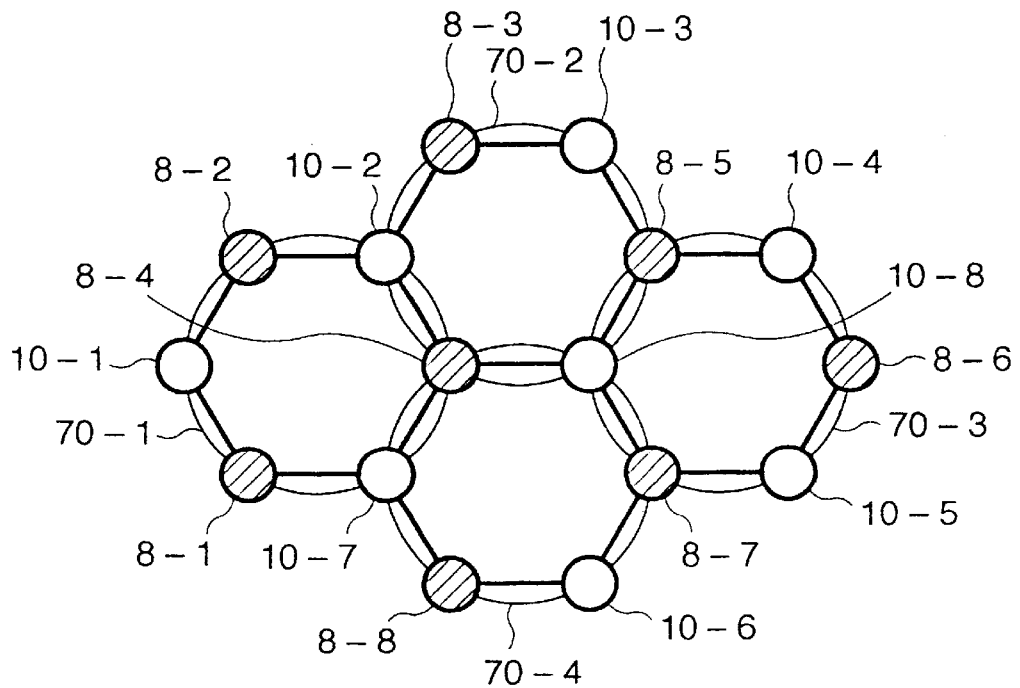
FIG. 23 is a diagram depicting a still further example of the relationship of placement between the incident optical fibers and the detection optical fibers employed in the embodiment shown in FIG. 15.

FIG. 23 shows a third layout configurational example in which a large number of incident optical fibers and detection optical fibers are disposed. In the present example, respective incident-detection optical fiber pairs or sets each composed of three pairs of incident and detection optical fibers disposed on the circumferences of respective one circles are respectively defined as basic fiber units. The basic fiber units are placed side by side in plural units so as to match the expansion of a desired measurement region.

When a measurement region is expanded with a incident-detection optical fiber pair composed of three pairs of incident and detection optical fibers disposed on the circumference of one circle being regarded as the basic fiber unit, the incident optical fibers and detection optical fibers are alternately disposed on respective nodes of each regular hexagonal lattice, and the incident optical fibers and the detection optical fibers are alternately disposed in the diagonal directions of the regular hexagonal lattice as shown in FIG. 23. In the present example, the number of the measurement positions is 4 and four circles 70-1 through 70-4 are provided around the respective measurement positions. Further, incident optical fibers 8-1 through 8-8 and detection optical fibers 10-1 through 10-8 are placed on the circumferences of the above circles and on the nodes of the regular hexagonal lattices. Owing to such an optical fiber layout, the incident optical fibers and the detection optical fibers disposed on points where the respective adjacent circles intersect, function with respect to the measurement positions whose number is identical to the number (three at nodes inside each lattice) of the circles intersecting each other at the nodes at which they are disposed. Therefore, the measurement positions can be measured with the less-reduced number of optical fibers. Although the number of the measurement positions is four in the present example, a further increase in the number of the measurement positions (i.e., the number of the circles and the number of the nodes) is easily achieved with a view toward carrying out a measurement on a wider measurement region. An image of hemodynamics at a deep tissue can be obtained from the result of measurement obtained by the widening of the measurement region.

<<Fourth Embodiment>>

Figure 24:
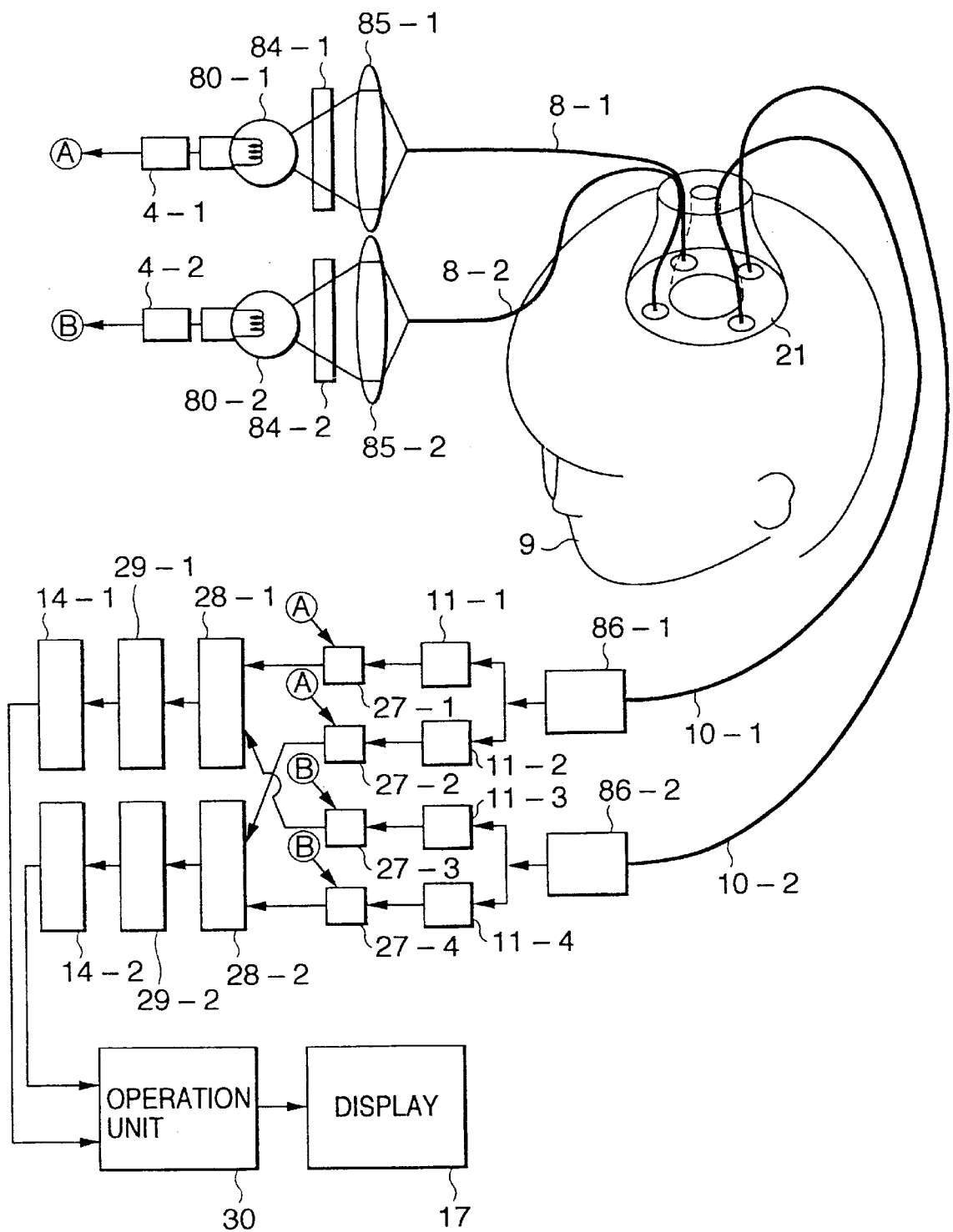
FIG. 24 is a diagram schematically illustrating a configuration of an optical measurement instrument for a living body, according to a fourth embodiment of the present invention, which is suitable for use in the measurement of information on the depth of a living body.

FIG. 24 shows an optical measurement instrument for a living body, according to a fourth embodiment of the present invention, which is suitable for use in the measurement of information on deep tissue.

In the present embodiment, a system for selecting suitable wavelength-range light from white light, irradiating a subject with it and spectroscopically measuring light transmitted through the subject with a spectroscope, thereby detecting transmitted lights of two wavelengths different from each other, which are necessary for measurement, is adopted with the objective of measuring oxy- and deoxyhemoglobin concentration changes in the subject (living body). Further, the number of light incident positions and the number of light detection positions with respect to the subject are respectively set to two. However, the number of these incident lights (the number of wavelengths), the number of the light incident positions and the number of the light detection positions can be further increased with ease. The increase in the number of the incident lights (the number of the wavelengths) also permits measurements on light-absorption substance concentration changes in other living bodies such as cytochrome, myoglobin, etc. as well as measurements on an oxyhemoglobin concentration change and a deoxyhemoglobin concentration change.

Referring to FIG. 24, white lights (corresponding to lights having continuous wavelength spectrums) outputted from white light sources 80-1 and 80-2 are respectively converted into wavelength-range lights necessary for measurement by passing through glass filters 84-1 and 84-2. Thereafter, the respective wavelength-range lights are respectively introduced into and transmitted to incident optical fibers 8-1 and 8-2 through lenses 85-1 and 85-2, followed by application to a subject (living body) 9. Here, the wavelength of each light incident onto the subject (living body) 9 is set so as to fall within a range of 400 nm to 2400 nm. Particularly when hemo-dynamics in the living body are measured, the glass filters 84-1 and 84-2 may preferably be selected so that the wavelength of each incident light falls within a range of 700 nm to 1100 nm. Further, the lights outputted from the light sources 80-1 and 80-2 are respectively intensity-modulated with mutually-different modulation frequencies f1 and f2 existing between 100 Hz and 10 MHz by light-source driver circuits 4-1 and 4-2. On the other hand, modulation frequency signals A and B outputted from the light-source driver circuits 4-1 and 4-2 are respectively inputted to phase sensitive detectors 27-1 and 27-2, and 27-3 and 27-4 as reference frequency signals. The incident optical fibers 8-1 and 8-2 are fixed to an optical fiber holder 21 together with detection optical fibers 10-1 and 10-2 and brought into contact with the surface of the subject 9.

The respective lights are applied to the subject 9 through the incident optical fibers 8-1 and 8-2. The detection optical fibers 10-1 and 10-2 collect the lights (transmitted lights) that have passed through the subject 9. Here, the incident optical fibers 8-1 and 8-2 and the detection optical fibers 10-1 and 10-2 are alternately placed on the circumference of one circle set on the optical fiber holder 21 at equal intervals. The detection optical fibers 10-1 and 10-2 are set so as to be respectively disposed at positions where they are opposed to the incident optical fibers 8-1 and 8-2 with the center of the circle interposed therebetween.

The lights transmitted through the subject (living body), which have been collected by the detection optical fibers 10-1 and 10-2, are respectively introduced into spectroscopes 86-1 and 86-2 where they are spectroscopically measured (wavelength-separated). The spectroscopes 86-1 and 86-2 select only component lights having $\lambda 1$ and $\lambda 2$ necessary for measurement from the spectroscopically-measured various component lights of wavelengths, respectively. The transmitted light components having the wavelengths $\lambda 1$ and $\lambda 2$ from the spectroscope 86-1 are respectively detected (photoelectrically-converted and amplified) by optical detectors 11-1 and 11-2, whereas the transmitted light components having the wavelengths $\lambda 1$ and $\lambda 2$ from the spectroscope 86-2 are respectively detected (photoelectrically-converted and amplified) by optical detectors 11-3 and 11-4. As the optical detectors 11-1 through 11-4, a photomultiplier tube or an avalanche photodiode is used. Output signals (transmitted light intensity signals) delivered from the optical detectors 11-1 through 11-4 are respectively inputted to phase sensitive detectors 27-1 through 27-4 respectively.

The signals inputted to the phase sensitive detectors 27-1 through 27-4 are respectively mixed with transmitted light intensity signals identical in wavelength but having different modulation frequencies. However, since the phase sensitive detectors 27-1 and 27-2, and 27-3 and 27-4 are supplied with reference frequency signals A and B having frequencies f1 and f2, which are outputted from the light-source driver circuits 4-1 and 4-2, only a transmitted light intensity component corresponding to the incident light having the wavelength $\lambda 1$, which is outputted from the incident optical fiber 8-1, is selectively separated and outputted from the phase sensitive detector 27-1, only a transmitted light intensity component corresponding to the incident light having the wavelength $\lambda 2$, which is outputted from the incident optical fiber 8-1, is selectively separated and outputted from the phase sensitive detector 27-2, only a transmitted light intensity component corresponding to the incident light having the wavelength $\lambda 1$, which is outputted from the incident optical fiber 8-2, is selectively separated and outputted from the phase sensitive detector 27-3, and only a transmitted light intensity component corresponding to the incident light having the wavelength λ2, which is outputted from the incident optical fiber 8-2, is selectively separated and outputted from the phase sensitive detector 27-4.

Both signals (intra-living body transmitted light intensity signals based on the incident lights each having the wavelength λ1, which have been delivered from the incident optical fibers 8-1 and 8-2) outputted from the phase sensitive detectors 27-1 and 27-3, are inputted to a multiplier 28-1 where both signals are subjected to mutual multiplication. Both signals (intra-living body transmitted light intensity signals based on the incident lights each having the wavelength λ2, which have been delivered from the incident optical fibers 8-1 and 8-2) outputted from the phase sensitive detectors 27-2 and 27-4, are inputted to a multiplier 28-2 where both signals are subjected to mutual multiplication. Signals outputted from the multipliers 28-1 and 28-2 are respectively inputted to logarithm amplifiers 29-1 and 29-2 where they are amplified in natural logarithm. Further, signals outputted from the logarithm amplifiers 29-1 and 29-2 are respectively inputted to A/D converters 14-1 and 14-2 where they are converted into digital signals, which in turn are taken in an operation unit 30.

Based on the taken-in time-sequence signals having the transmitted light intensities of two wavelengths, the operation unit 30 computes an oxyhemoglobin concentration change, a deoxyhemoglobin concentration change, and the sum (total hemoglobin concentration change) of the oxyhemoglobin concentration change and the deoxyhemoglobin concentration change, which indicates the volume of blood. The result of computation by the operation unit 30 is displayed on a display device 17 as a time-sequence change graph.

Figure 25:
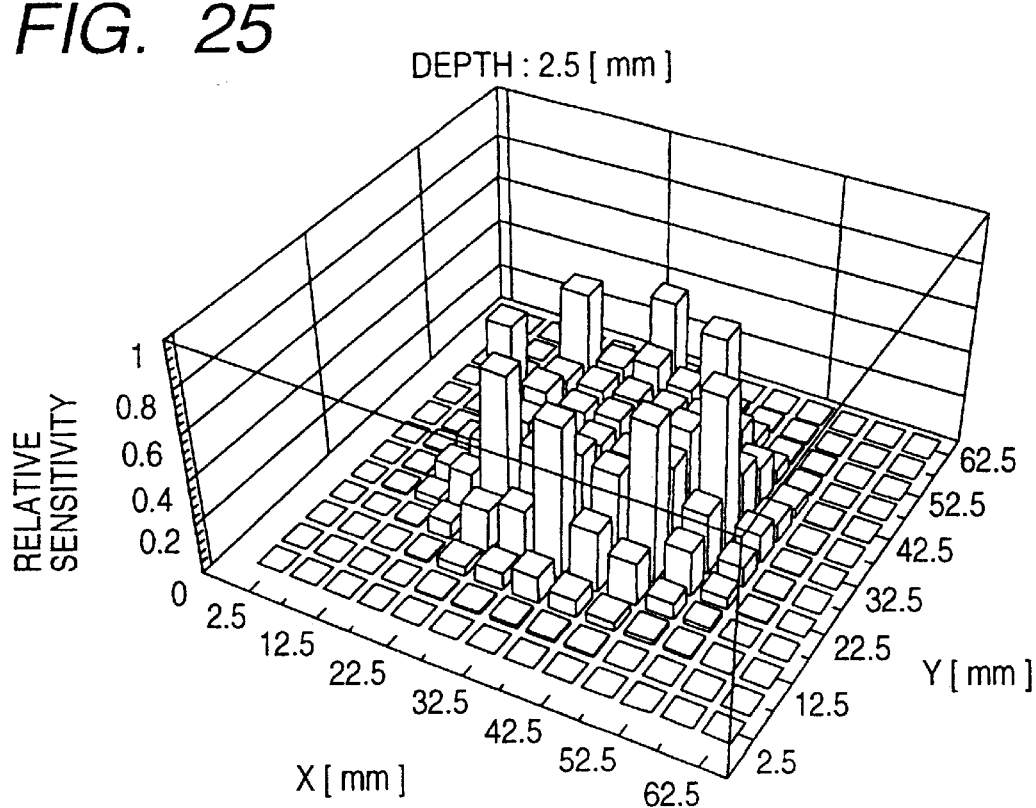
FIGS. 25, 26 and 27 are respectively diagrams showing the relationship between measurement sensitivity distributions and depths in living body at inner living body measurements under the instrument configuration shown in FIG. 24.
Figure 26:
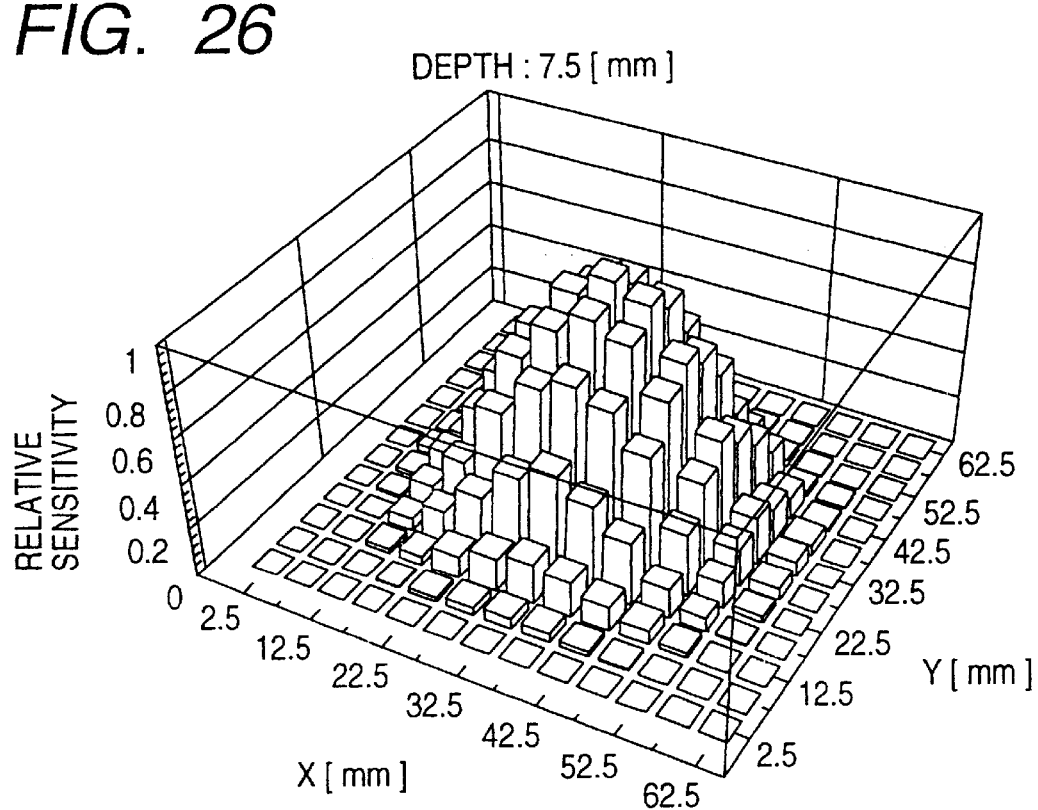
Figure 27:
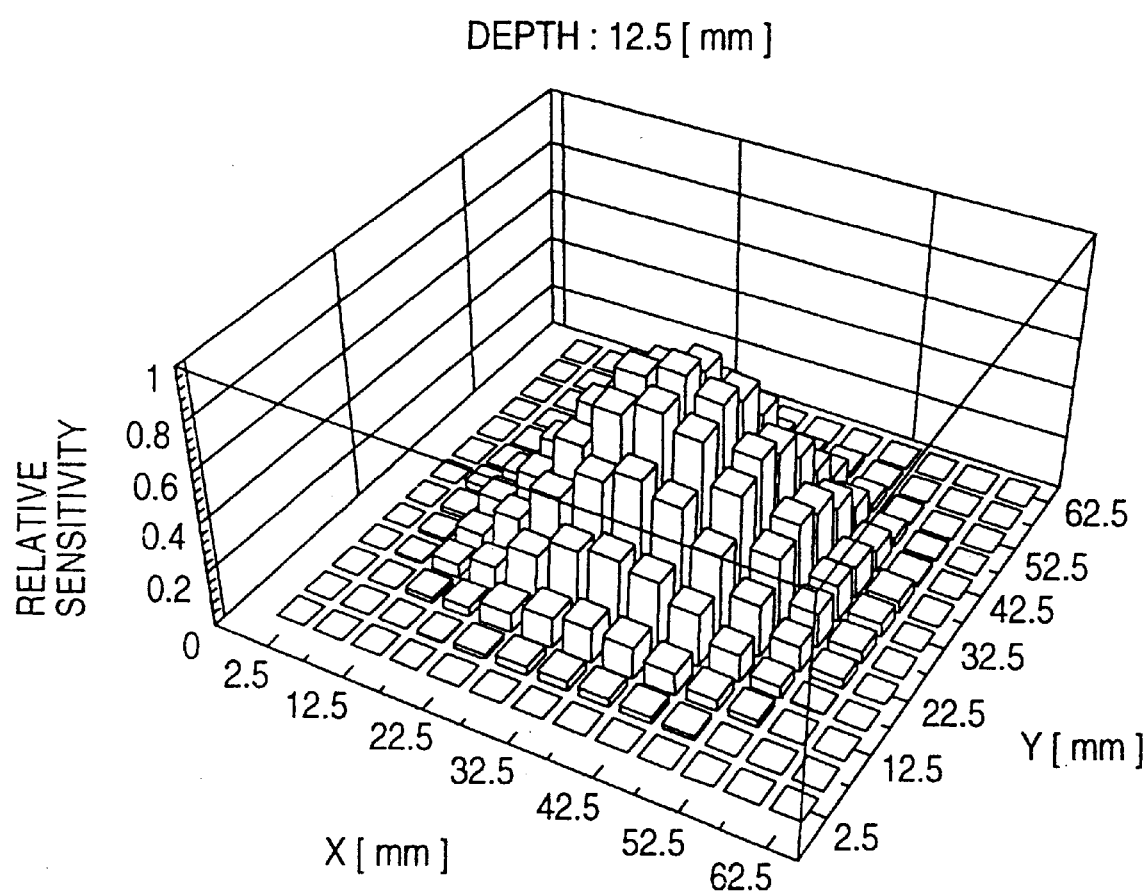

The aforementioned third embodiment (see FIG. 15) and the above-described fourth embodiment (see FIG. 24) respectively show the case in which the incident-detection optical fiber pairs are attached to the optical fiber holder 21 as two pairs. However, the measurement sensitivity to the deep portion in the subject (living body) can be improved on a leap basis by further increasing the incident-detection optical fiber pairs attached to the optical fiber holder 21 to plural pairs. Results of measurements obtained when the incident-detection optical fiber pairs are provided in the optical fiber holder 21 in four pairs under the instrument configuration shown in FIG. 24, will be shown in FIGS. 25, 26 and 27. Results of measurements obtained when the surface of the subject (living body) is assumed to be a plane, the plane parallel to the plane thereof is defined as an X-Y plane, a circle whose center is located in a position given by x=32.5 mm and y=32.5 mm and whose diameter is 30 mm, is set on the surface of the living body, the incident optical fibers and the detection optical fibers are alternately disposed on the circumference of the circle by four, and the incident-detection optical fiber pairs composed of the incident optical fibers and the detection optical fibers placed in positions point-to-point symmetrical with each other with the center of the circle as a point symmetrical center are set as four pairs, are represented as a relative sensitivity distribution (see FIG. 25) at a depth position of 2.5 mm in the living body, a relative sensitivity distribution (see FIG. 26) at a depth position of 7.5 mm in the living body, and a relative sensitivity distribution (see FIG. 27) at a depth position of 12.5 mm in the living body. According to the present invention, as is apparent from the comparison between the measurement results (see FIGS. 12 through 14) obtained by the previously-described conventional example and the measurement results (see FIGS. 25 through 27) obtained by the present invention, the measurement sensitivity at the deep portions in the living body can be greatly improved.

The present embodiment has shown the configurational example in which intra-subject transmitted lights of lights having a plurality of wavelengths incident from a plurality of light incident positions on a predetermined circle are detected at a plurality of light collection positions set to positions point-symmetrical with respect to the plurality of light incident positions on the circle with the center of the circle interposed therebetween, and all the intensities of the transmitted lights detected at the plurality of light collection positions are subjected to multiplication every same wavelengths. However, even if such an instrument configuration that all the intensities are added together every same wavelengths, is taken likewise, a physical meaning is degraded but relative sensitivity to a deep portion in a living body can be improved. Further, measurement sensitivity to an intended measurement region may be improved by using an instrument configuration for performing the four operations of the intensities of the lights transmitted through the subject (living body), which have been detected at the plurality of light collection positions.

According to the present invention, a light-absorption substance concentration in a predetermined depth region in a subject (living body) can be measured with satisfactory accuracy. As a measurement example required to provide sufficient measurement sensitivity to the deep portion in the subject (living body), may be mentioned a measurement on a change in hemo-dynamics incident to functional brain activity, for example. According to the present invention, however, the change in hemo-dynamics incident to the functional brain activity can be measured from the head skin.

Input and Control Devices by Living Body

Further, according to the present invention, as has already been described above, since the optical measurement instrument for the living body can be implemented which is capable of measuring the living-body information about the wide spatial region in the subject (living body) with high efficiency and accuracy and at high spatial resolution, high-utility input and control devices by living body can be realized which is capable of controlling various pieces of external equipment promptly and with high accuracy by using measurement signals produced from the optical measurement instrument as signals to be directly input to the various pieces of external equipment.

Various input devices such as a keyboard, a mouse, a handle, etc. are used to control or operate a computer and a game machine or the like. Such input devices to be controlled by the human hands and legs lessen realism in the game machine or make the operation of a physically handicapped person or the like difficult. Therefore, a device for directly inputting brain waves from a brain has been proposed by Japanese Patent Application Laid-Open No. 7-124331, for example. This device is intended to control the computer, particularly the game machine by inputting the brain waves or electroencephalogram to the computer as they are as in the case of the measurement of an electrocardiogram.

This type of input device has been expected in that it allows persons whose motion functions are recognized as handicapped to facilitate the control of the pieces of external equipment and is able to contribute to the entry of the physically handicapped into society.

Meanwhile, a human brain is divided into regions in simple cell construction as represented by the Brodmann brain map. Further, the respective regions share different functions. If the brain is viewed from the transverse side thereof, for example, a region that participates in spontaneous motion (hands, fingers, legs, etc.), is placed in the top of the brain, a region concerned in sensation, vision, etc. is placed in the occiput, and a region concerned in the language is placed in a predetermined portion corresponding to the left half of the brain.

Thus, the extraction of information from the specific regions in the brain with high accuracy needs to use a measurement instrument high in spatial resolution. However, since the position of occurrence of a signal (brain waves) becomes indefinite due to the ununiformity of the dielectric constant in the living body, it is difficult to measure the electroencephalogram employed in the prior art at high spatial resolution. Further, since a myo-electric potential produced when the subject moves, is greatly reflected on brain measurement signals and exerts a bad influence on the result of measurement, there are also restricted conditions that the motion of the subject must be restrained upon measurement. Thus, the method of using the electroencephalogram as the signals inputted directly from the brain as they are has a problem in terms of the accuracy and practical utility.

According to the present invention, as has already been described above, since the optical measurement instrument for the living body can be implemented which is capable of measuring the living-body information about the wide spatial region in the subject (living body) with high efficiency and accuracy and at high spatial resolution, high-utility input and control devices by living body can be realized which is capable of controlling various pieces of external equipment promptly and with high accuracy by using measurement signals produced from the optical measurement instrument as signals to be directly input to the various external equipment.

The input device by living body using an optical measurement method for the living body, according to the present invention, comprises light incident means for applying lights to an inner brain from the outside of the skin of a human head, collecting light means for collecting lights transmitted through the inside brain by the application of the lights to the inside brain by the light incident means, light measuring means for measuring the intensities of the transmitted lights collected by the collecting light means, and computation or operation means for determining by computation or operation an oxyhemoglobin concentration change value and a deoxyhemoglobin concentration change value or a total hemoglobin concentration change value in a predetermined region in the brain from the transmitted light intensities measured by the light measuring means, determining desired characteristic parameter values from the hemoglobin concentration change values determined by operation, and determining the type of output signal based on the characteristic parameter values determined by operation.

Further, the input device by living body can include storing means for pre-setting and storing the rate of change in hemoglobin concentrations at arbitrary time intervals, the intensities of hemoglobin concentration at time-varying arbitrary frequencies, which are to be computed and determined by the operation means, as reference data about the characteristic parameter values. In this case, the operation means determines and outputs the type of output signal from the characteristic parameter values determined by the above operation and the reference data stored in the storing means.

The control device by living body using the optical measurement method for the living body, according to the present invention includes the above-described input device and a piece of external equipment for using the output signal determined by the input device as an input signal and performing a predetermined functional operation according to the type of the input signal.

Incidentally, the lights collected by the collecting light means are classified into lights reflected from the inside living body (brain) and lights transmitted therethrough. However, the above lights will be referred to as lights (transmitted lights) passing through the living body inclusive of both in the present invention.

In the present invention, brain functional activity localized within the living body (brain) is measured using lights and a signal obtained by the measurement is used as a signal to be inputted to a piece of external equipment such as a computer or the like. Namely, incident optical fibers and detection optical fibers are placed in positions on the surface of the head corresponding to a desired measurement region (such as a right fingers motor area, a left fingers motor area, a language area or the like) in the brain to irradiate the inside brain with the lights, thereby collecting and measuring the lights transmitted through the inside brain. Further, signals corresponding to the measured lights are inputted to an operation unit. The operation unit determines the type of output signal for shifting the cursor to the left with respect to the signal obtained from the right fingers motor area, shifting the cursor to the right with respect to the signal obtained from the left fingers motor area, or performing a click operation with respect to the signal obtained from the language area, for example, and inputs the output signal to a piece of external equipment such as a computer, a word processor, a game machine or the like. The external equipment performs operation according to the type of input signal referred to above.

In another example of the operation by the operation unit, an oxyhemoglobin concentration change value and a deoxyhemoglobin concentration change value, or a total hemoglobin concentration change value are computed based on measured intracerebral transmitted light intensities. Further, characteristic parameter values are determined from these concentration change values by computation. The characteristic parameter values determined by computation are compared with the characteristic parameter values (reference data) stored in a memory device or unit in advance to thereby decide the type of output signal. The output signal is inputted to a piece of external equipment.

In a further example of the operation by the operation unit, an operator is urged to imagine the contents of operations such as [Cursor to the Right], [Cursor to the Left], [CLick], etc. without associating signals inputted to a piece of external equipment with specific measurement regions. Standard deviations and mean values every characteristic parameters at every measurement regions at that time are stored in a memory unit as learning data. Next, actual measured values are compared with these learning data. If they are found to coincide with each other within the allowable range, then a signal for providing instructions for executing the contents of operation corresponding to the learning data is outputted. Since the type of output signal is determined by this method, using the characteristic parameters, a neutral network can be also utilized as well as the Maharanovis distance. The term Maharanovis distance indicates an index for making a decision as to whether the actually-measured value belongs to the normal distribution having dispersion when the measured values or the like are represented by the normal distribution.

Since these methods can directly control the computer, word processor, game machine, etc. without using a keyboard, a mouse, etc., they can be also used as for the physically handicapped.

Owing to the placement of light incident means and collecting light means in many points on the surface of a subject (head of living body), the present invention can be also applied to a driver's doze warning device, an environmental control device, a learning-level determining device, an indicator for indicating intention of a patient, childhood, animals, etc., an information transmission device, or a lie detector or the like.

Embodiments of the present invention will hereinafter be described in detail with reference to the accompanying drawings.

<<Fifth Embodiment>>

Figure 28:
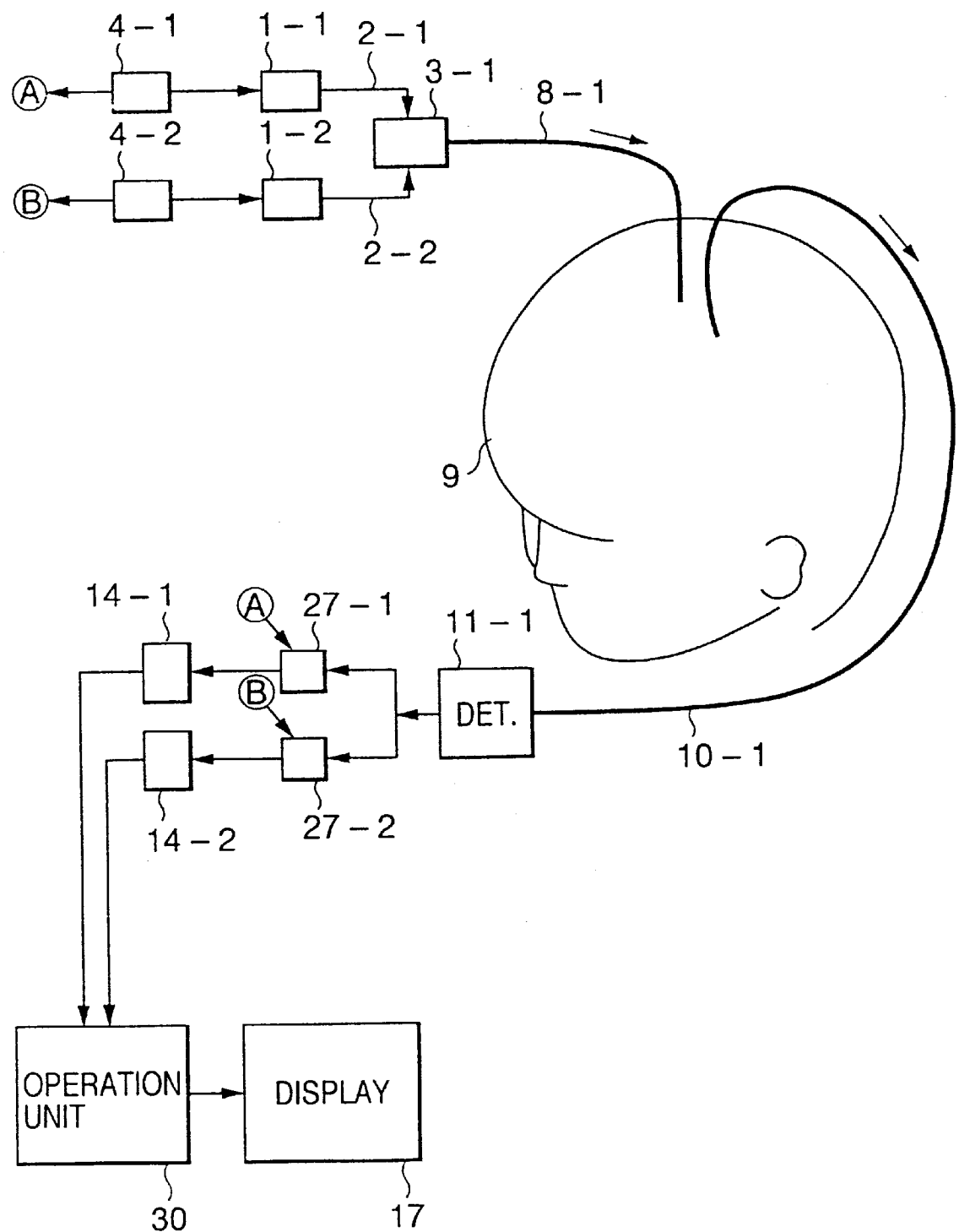
FIG. 28 is a diagram schematically depicting a configuration of a measurement system of brain activity, which is employed in an optical measurement instrument for a living body, according to a fifth embodiment of the present invention.

FIG. 28 shows a schematic configuration of a measurement system of brain activity, which is employed in an input device by living body, according to a fifth embodiment of the present invention.

In the present embodiment, localized brain activities are measured using lights and the resultant signals are used as signals to be inputted to a computer or a piece of external equipment.

In the present embodiment, oxy- and deoxyhemoglobin concentration changes are respectively independently measured using lights of two wavelengths different from each other as incident lights with the objective of measuring the oxy- and deoxy-hemoglobin concentration changes in a brain. Namely, an oxyhemoglobin concentration and a deoxyhemoglobin concentration are fractionally measured using the difference (corresponding to the difference between light-absorption wavelengths) between the colors of oxyhemoglobin and deoxyhemoglobin. If the number of wavelengths of incident lights is further increased, then measurement accuracy is further improved and the concentration of substances other than the oxyhemoglobin and the deoxyhemoglobin can be also measured. A description will now be made of the case in which the number of light incident positions and the number of light detection positions are respectively set to one. However, a measurement region can be easily widened by increasing the numbers of the light incident positions and the light detection positions.

Referring to FIG. 28, lights of specific wavelengths $\lambda 1$ and $\lambda 2$ are outputted from light sources 1-1 and 1-2 and introduced into optical fibers 2-1 and 2-2, respectively. The wavelengths $\lambda 1$ and $\lambda 2$ of the lights outputted from the light sources 1-1 and 1-2 are respectively selected from a 400 nm-to-2400 nm wavelength range. It is desirable for improvements in measurement accuracy that particularly when hemo-dynamics in the living body are measured, the wavelengths are selected from a 700 nm-to-1100 nm wavelength range so that the difference between the wavelengths falls within 50 nm. Namely, the permeability of light in the living body is high in this wavelength range. Inconvenience occurs because a wavelength longer than the above wavelengths increases the absorption of light by water and a wavelength shorter than the above wavelengths also enhances the absorption of light by the hemoglobin itself. The output lights emitted from the light sources 1-1 and 1-2 are intensity-modulated with modulation frequencies f1 and f2 different from each other by their corresponding driver circuits 4-1 and 4-2. Further, modulation frequency signals A and B outputted from the driver circuits 4-1 and 4-2 are inputted to their corresponding phase sensitive detectors 27-1 and 27-2 as reference frequency signals. This is because a signal component corresponding to an oxyhemoglobin concentration value and a signal component corresponding to a deoxyhemoglobin concentration value are separated and extracted from detection signals mixed with both the signal components.

The optical fibers 2-1 and 2-2 are electrically connected to an optical coupler 3-1 where the lights of the wavelengths $\lambda 1$ and $\lambda 2$ from the light sources 1-1 and 1-2 are mixed together. Thereafter, the mixed light is introduced into an incident optical fiber 8-1 so as to be transmitted to the surface of a subject (living body) 9.

The light is launched into the subject (living body) 9 through the incident optical fiber 8-1. The light passing through the living body is collected and detected by a detection optical fiber 10-1. Thus, changes in oxy- and deoxy-hemoglobin concentrations in the blood can be measured as their corresponding color changes (changes in light-absorption wavelengths). Oxygen saturation (corresponding to the proportion of oxyhemoglobins in all the hemoglobins) is high in the artery, whereas the oxygen saturation is reduced in the vein as compared with the artery.

The distance between the incident optical fiber 8-1 and the detection optical fiber 10-1 is set so as to fall within a 10 mm-to-50 mm range according to, for example, a depth in the living body within a desired measurement region, but is set to 30 mm in the present embodiment.

The light passing through the living body, which has been collected by the detection optical fibers 10-1, is introduced into an optical detector 11-1 where it is photoelectrically converted and amplified. As the optical detector 11-1, a photomultiplier tube or an avalanche photodiode is used. An output signal delivered from the optical detector 11-1 is divided into two, which in turn are inputted to the phase sensitive detectors 27-1 and 27-2 respectively.

Intensity signals of lights passing through the living body, corresponding to the lights of the two wavelengths $\lambda 1$ and $\lambda 2$, which are launched into the living body 9 from the incident optical fiber 8-1, are respectively mixed into the signals inputted to the phase sensitive detectors 27-1 and 27-2. However, since the phase sensitive detectors 27-1 and 27-2 are supplied with the reference frequency signals outputted from the driver circuits 4-1 and 4-2, the intensity signal of the light passing through the living body, corresponding to the incident light of the wavelength $\lambda 1$ (modulation frequency f1) emitted from the light source 1-1, is separated and/or selected by the phase sensitive detector 27-1 and outputted therefrom, and the intensity signal of the light passing through the living body, corresponding to the incident light of the wavelength $\lambda 2$ (modulation frequency f2) emitted from the light source 1-2, is separated and/or selected by the phase sensitive detector 27-2 and outputted therefrom.

The transmitted light intensity signals separated and/or selected by and outputted from the phase sensitive detectors 27-1 and 27-2 respectively are next inputted to their corresponding A/D converters 14-1 and 14-2 where they are converted into digital signals, which in turn are taken or introduced into an operation unit 30.

Based on the taken-in time-sequence signals having the transmitted light intensities of two wavelengths, the operation unit 30 computes an oxyhemoglobin concentration, a deoxyhemoglobin concentration, and the sum of the oxyhemoglobin concentration and the deoxyhemoglobin concentration change, which indicates the volume of blood. The result of computation by the operation unit 30 is displayed on a display device 17 as a time-sequence change graph. The total amount (volume) of hemoglobins in the blood is held constant. Thus, the simple addition of the volume of the oxyhemoglobin and the volume of the deoxyhemoglobin results in the whole volume of blood.

A method of computing an oxyhemoglobin concentration change, a deoxyhemoglobin concentration change and a total hemoglobin concentration change incident to the functional brain activity under the instrument configuration of the present embodiment has been proposed in, for example, the specification and the accompanying drawings in the Patent Application (Japanese Patent Application No. 7-30972) of the present applicant (arithmetic or operation processing method). In the present method, only the amount of change in the hemoglobin concentration is computed. However, the absolute amount of each hemoglobin concentration can be also measured if an arithmetical operation for eliminating the influence of light scattering in the living body is performed.

Figure 29:
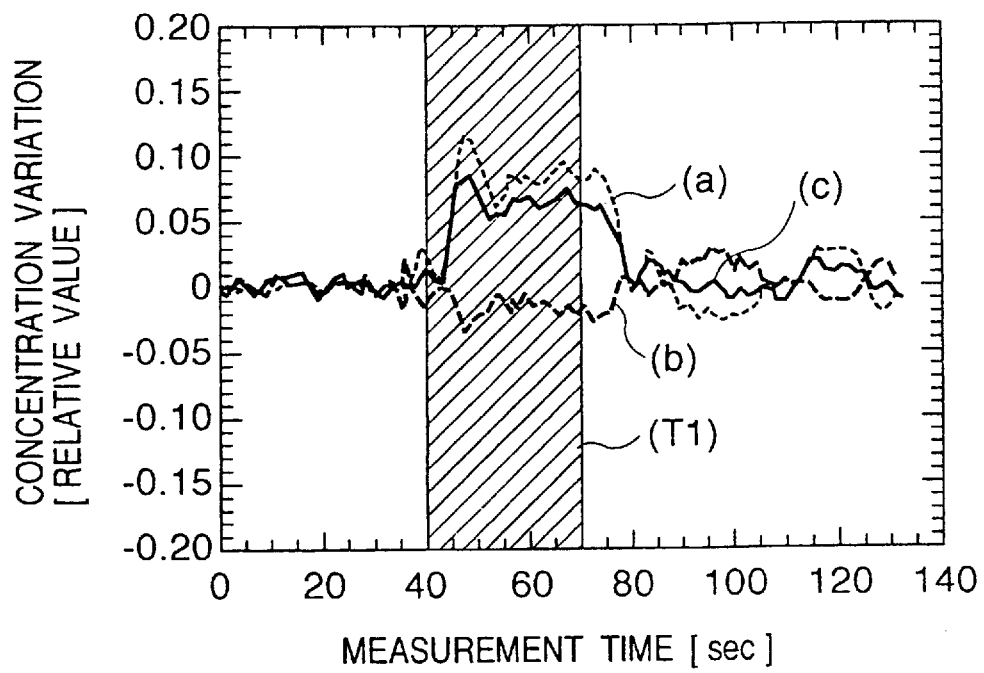
FIG. 29 is a line map showing one example of a right fingers movement concentration change in hemoglobin in the brain, which has been measured by the instrument configuration shown in FIG. 28.

FIG. 29 is a graph showing one example of a right fingers movement concentration change or variation in hemoglobin, which has been measured by the measurement system of brain activity according to the present embodiment. The graph shows time-sequence variations such as an oxyhemoglobin concentration variation (a), a deoxyhemoglobin concentration variation (b) and a total hemoglobin concentration variation (c) at the time that an intracerebral region (right fingers motor area) related to the movements of the right fingers is defined as a measurement region and the right fingers movements are performed. Incidentally, a diagonally-shaded time region ($T_1$) indicates a right fingers movement period.

Figure 30:
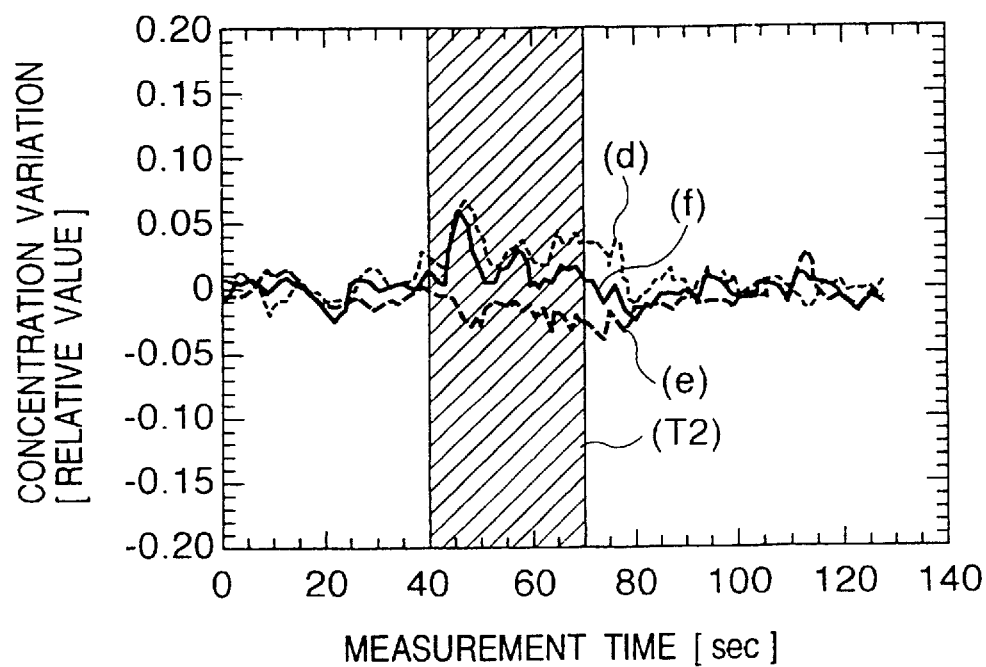
FIG. 30 is a line map illustrating one example of a left fingers movement concentration change in hemoglobin in the brain, which has been measured by the instrument configuration shown in FIG. 28.

FIG. 30 is a graph showing one example of a left fingers movement concentration change or variation in hemoglobin, which has been measured by the measurement system of brain activity according to the present embodiment. The graph shows time-sequence variations such as an oxyhemoglobin concentration variation (d), a deoxyhemoglobin concentration variation (e) and a total hemoglobin concentration variation (f) at the time that an intracerebral region (left fingers motor area) related to the movements of the left fingers is defined as a measurement region and the left fingers movements are performed. Incidentally, a diagonally-shaded time region ($T_2$) indicates a left fingers movement period.

As is apparent from the comparison between FIG. 29 and FIG. 30, the oxyhemoglobin concentration variation (a) and the total hemoglobin concentration variation (c) in the right fingers motor area during the right fingers movement period ($T_1$) respectively indicate variations corresponding to about three times the oxyhemoglobin concentration variation (d) and the total hemoglobin concentration variation (f) in the left fingers motor area during the left fingers movement period ($T_2$). Incidentally, the motor area on the intracerebral left side is a region related to the movement of the right side of the body and the motor area on the intracerebral right side is a region related to the movement of the left side of the body. The intracerebral region and a body portion concerned in the intracerebral region have a cross relation or affinity with each other. It is understood from FIGS. 29 and 30 that the oxyhemoglobin concentration variations (b) and (e) do not vary noticeably so far.

Figure 31:
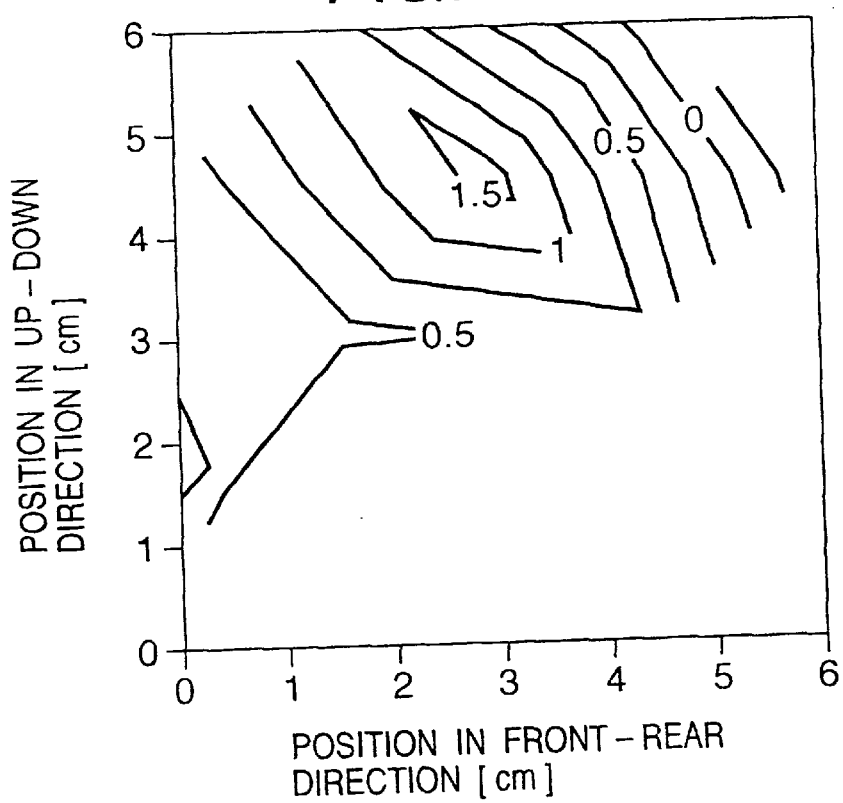
FIG. 31 is a contour map depicting one example of a right fingers movement concentration change in total hemoglobin in the brain, which has been measured by the instrument configuration shown in FIG. 28.

FIG. 31 is a contour map showing one example of a total hemoglobin concentration variation at the movements of the right fingers, which has been measured by the measurement system of brain activity according to the present embodiment. In the present example, the total hemoglobin concentration variation at the time that functional brain activities are measured at many points in the brain so that the right fingers motor area is contained, and the right fingers movements are performed, is represented as a contour map. In FIG. 31, an up-down direction in the drawing corresponds to an up-down direction of the brain, the left side in the drawing corresponds to the front side of the brain, and the right side in the drawing corresponds to the rear side of the brain. It is understood from the drawing that the functional brain activities at local portions in the brain, which indicate such noticeable variations, have been measured.

Figure 32:
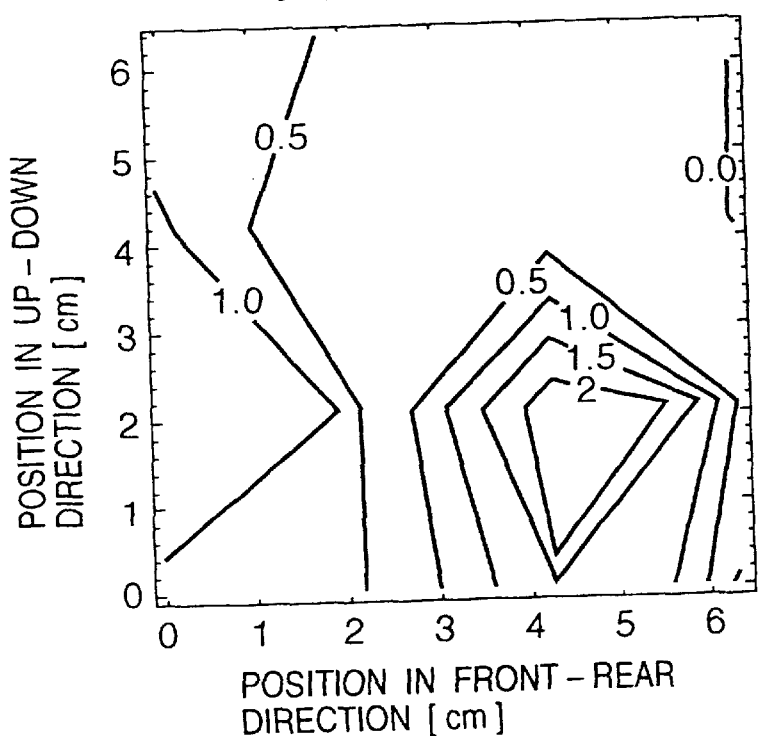
FIG. 32 is a contour map illustrating one example of a language recollection concentration change in total hemoglobin in the brain, which has been measured by the instrument configuration shown in FIG. 28.

FIG. 32 is a contour map illustrating one example of a total hemoglobin concentration variation at language recollection, which has been measured by the measurement system of brain activity according to the present embodiment. In the present example, the oxyhemoglobin concentration variation at the time that functional brain activities are measured at many points in the brain so that an intracerebral region (language area) related to language activity is contained, and the language is recollected, is represented by a contour map. The language area exists in an intracerebral position near the temple on the head left side. Even in the language area, the functional brain activities at local portions in the brain, which indicate noticeable variations, have been measured by the measurement system of brain activity according to the present embodiment. According to the measurement system of brain activity showing the present embodiment, such language recollection activity in the brain can be also measured.

Accordingly, the present invention can implement a high accuracy and utility direct input method by brain by using measurement signals satisfactory in accuracy measured by the above-described measurement system of brain activity as signals to be input to a piece of external equipment.

A summary of the fundamental configuration of the measurement system of brain activity employed in the input device by living body according to the present invention has been described above. Therefore, specific configurational examples of the input and control devices by living body according to the present invention will be described below.

Figure 33:
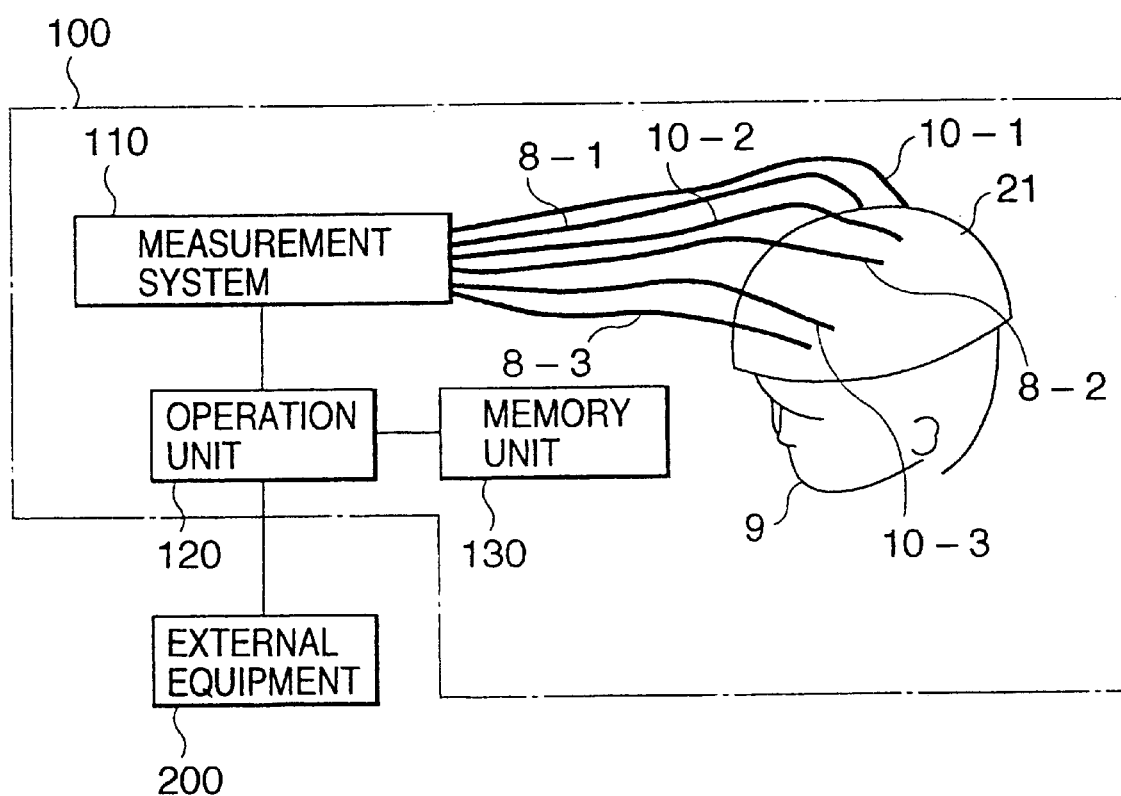
FIG. 33 is a diagram schematically showing a configuration of a control device by living body, according to a fifth embodiment of the present invention.

FIG. 33 is a diagram schematically showing a configuration of a control device by living body, according to a fifth embodiment of the present invention.

Referring to FIG. 33, the control device by living body according to the present embodiment comprises an input device 100 by living body and a piece of external equipment 200.

In the input device 100, a subject (human head) 9 is irradiated with lights through incident optical fibers 8-1, 8-2 and 8-3 by using the measurement system 110 of brain activity having the configuration shown in FIG. 28. Lights transmitted through the subject 9 are collected by detection optical fibers 10-1, 10-2 and 10-3. Thereafter, the measurement system 110 measures the intensities of the transmitted lights. These incident and detection optical fibers are respectively fixed to an optical fiber fixing helmet 21 so that a pair of the incident optical fiber 8-1 and the detection optical fiber 10-1 corresponds to a first measurement region, a pair of the incident optical fiber 8-2 and the detection optical fiber 10-2 corresponds to a second measurement region and a pair of the incident optical fiber 8-3 and the detection optical fiber 10-3 corresponds to a third measurement region. With an increase in the number of the incident-detection optical fiber pairs, the number of the measurement regions can be further increased with ease. It is also easy to dispose a plurality of optical fiber pairs within the respective measurement regions for the objective of improving measurement accuracy (spatial resolution).

The intensities of the lights passing through the respective measurement regions, which have been measured by the measurement system 110, are inputted to an operation unit 120. The operation unit 120 performs an arithmetical operation using the transmitted light intensities inputted thereto, the light-absorption coefficients of oxy- and deoxy-hemoglobins, which have been stored in a memory unit 130 in advance, and other operational data in accordance with a computation or operation method to be described later to thereby specify a desired signal. Thereafter, the operation unit 120 inputs the desired signal to the external equipment 200. In order to determine to what meaning each signal corresponds, results (light-absorption coefficients of hemoglobins and various computing data) learned up to now are stored in the memory unit 130.

The external equipment 200 is activated according to the type of signal inputted from the operation unit 120. As the external equipment 200, may be mentioned a computer, a word processor, a game machine or a communication device or the like.

A method of performing an arithmetic operation by the operation unit 120 will next be described.

Figure 34:
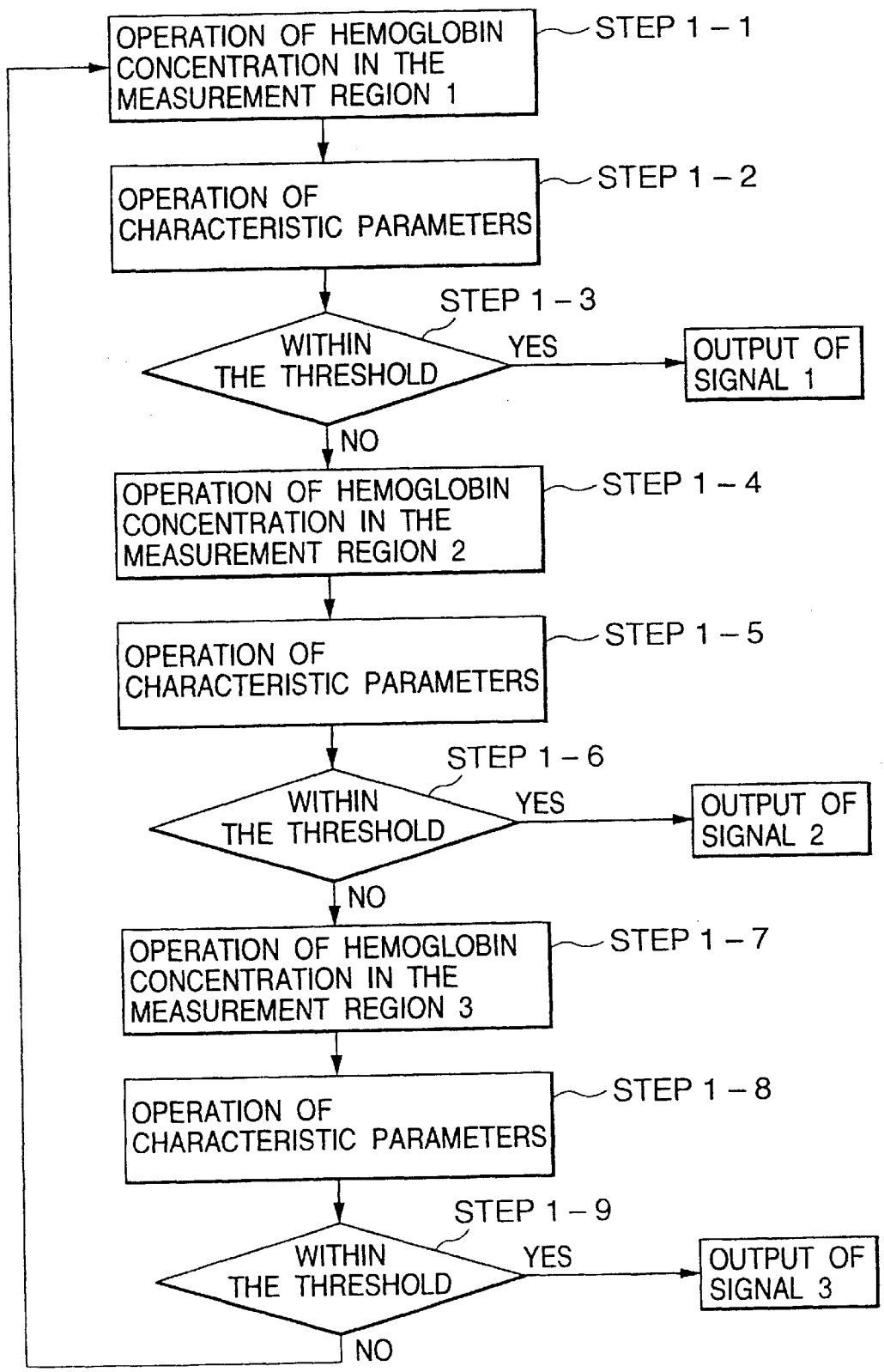
FIG. 34 is a flowchart for describing a first operation procedural example in an operation unit employed in the embodiment shown in FIG. 33.

FIG. 34 is a flowchart for describing a first operation procedural example of the operation unit 120.

For example, the pair of the incident optical fiber 8-1 and the detection optical fiber 10-1, the pair of the incident optical fiber 8-2 and the detection optical fiber 10-2, and the pair of the incident optical fiber 8-3 and the detection optical fiber 10-3 are disposed so as to correspond to a left fingers movement area (measurement region 1), a right fingers movement area (measurement region 2) and a language area (measurement region 3) respectively. The intensities of lights passing through a living body in the respective measurement regions are measured and the results of measurements are inputted to the operation unit 120.

(Step 1-1)
An oxy-, deoxy- or total-hemoglobin concentration value is computed from the intensities of the transmitted lights of respective wavelengths from the measurement region 1.

(Step 1-2)
Each of characteristic parameter values is determined by an operation or computation from the respective or arbitrary hemoglobin concentration values computed in step 1-1, i.e., the oxy, deoxy and total hemoglobin concentration values or one arbitrary concentration value of these concentration values. As the characteristic parameters, for example, integrated values of respective or arbitrary hemoglobin concentrations at arbitrary time intervals, the rates of changes in the respective or arbitrary hemoglobin concentrations at arbitrary times, or the intensities of arbitrary frequencies corresponding to time changes in respective or arbitrary hemoglobin concentrations are used. These can be determined in various ways.

(Step 1-3)
The characteristic parameter value determined by operation or computation in step 1-2 is compared with the learning values stored in the memory unit 130. It is determined whether the characteristic parameter value falls within a predetermined arbitrary threshold range. If it is found to fall within the threshold range (if the answer is found to be yes), then the operation unit 120 outputs a signal 1. If it is found to fall outside the threshold range (if the answer is found to be no), then the operation unit 120 proceeds to step 1-4.

(Step 1-4)
An oxy-, deoxy- or total-hemoglobin concentration value is computed from the intensities of the transmitted lights of respective wavelengths from the measurement region 2.

(Step 1-5)
Each of characteristic parameter values is determined by operation from the respective or arbitrary hemoglobin concentration values computed in step 1-4. As the characteristic parameters, for example, integrated values of the respective or arbitrary hemoglobin concentration values at arbitrary time intervals, the rates of changes in the respective or arbitrary hemoglobin concentrations at arbitrary times, or the intensities of arbitrary frequencies corresponding to time changes in respective or arbitrary hemoglobin concentrations are used. These can be determined in various ways.

(Step 1-6)
It is determined whether the characteristic parameter value determined by operation in step 1-5 falls within a predetermined arbitrary threshold range. If it is found to fall within the threshold range (if the answer is found to be yes), then the operation unit 120 outputs a signal 2 therefrom. If it is found to fall outside the threshold range (if the answer is found to be no), then the operation unit 120 proceeds to step 1-7.

(Step 1-7)
An oxy-, deoxy- or total-hemoglobin concentration value is determined by operation from the intensities of the transmitted lights of respective wavelengths from the measurement region 3.

(Step 1-8)
Each of characteristic parameter values is determined by operation from the respective or arbitrary hemoglobin concentration values computed in step 1-7. As the characteristic parameters, for example, integrated values or mean values of respective or arbitrary hemoglobin concentrations at arbitrary time intervals, the rates of changes in the respective or arbitrary hemoglobin concentrations at arbitrary times, or the intensities of arbitrary frequencies corresponding to time changes in respective or arbitrary hemoglobin concentrations are used. These can be determined in various ways.

(Step 1-9)
It is determined whether the characteristic parameter value determined by operation in step 1-8 falls within a predetermined arbitrary threshold range. If it is found to fall within the threshold range (if the answer is found to be yes), then the operation unit 120 outputs a signal 3 therefrom. If it is found to fall outside the threshold range (if the answer is found to be no), then the operation unit 120 returns to step 1

The external equipment 200 is always placed in an input waiting state assuming that the external equipment 200 is a computer. Further, the function of the external equipment 200 responsive to the input signal may be set in advance so as to correspond to each input signal as in the case where the cursor is shifted to the left with respect to the input of the signal 1, the cursor is shifted to the right with respect to the input of the signal 2 and a click operation is made to the input of the signal 3.

An expansion example of the operation method is as follows: If the operation unit 120 is set so as to output a "0" signal when the characteristic parameter value falls within the threshold range and a "1" signal when it falls outside the threshold range in step 1-3, step 1-6 and step 1-9, then eight combinations (000 through 111) can be created as signals to be outputted from the operation unit 120. In this case, the signals from the signals 1 to 8 are outputted from the operation unit 120. In this condition, the function of the external equipment 200 responsive to the individual output signals may be determined in advance.

The first operation procedural example has described the case in which the measurement regions are set to the right fingers motor area, left fingers motor area and language area in advance and a one-to-one correspondence is made between each of the measured signals form the respective measurement regions and the response function of the external equipment.

Figure 35:
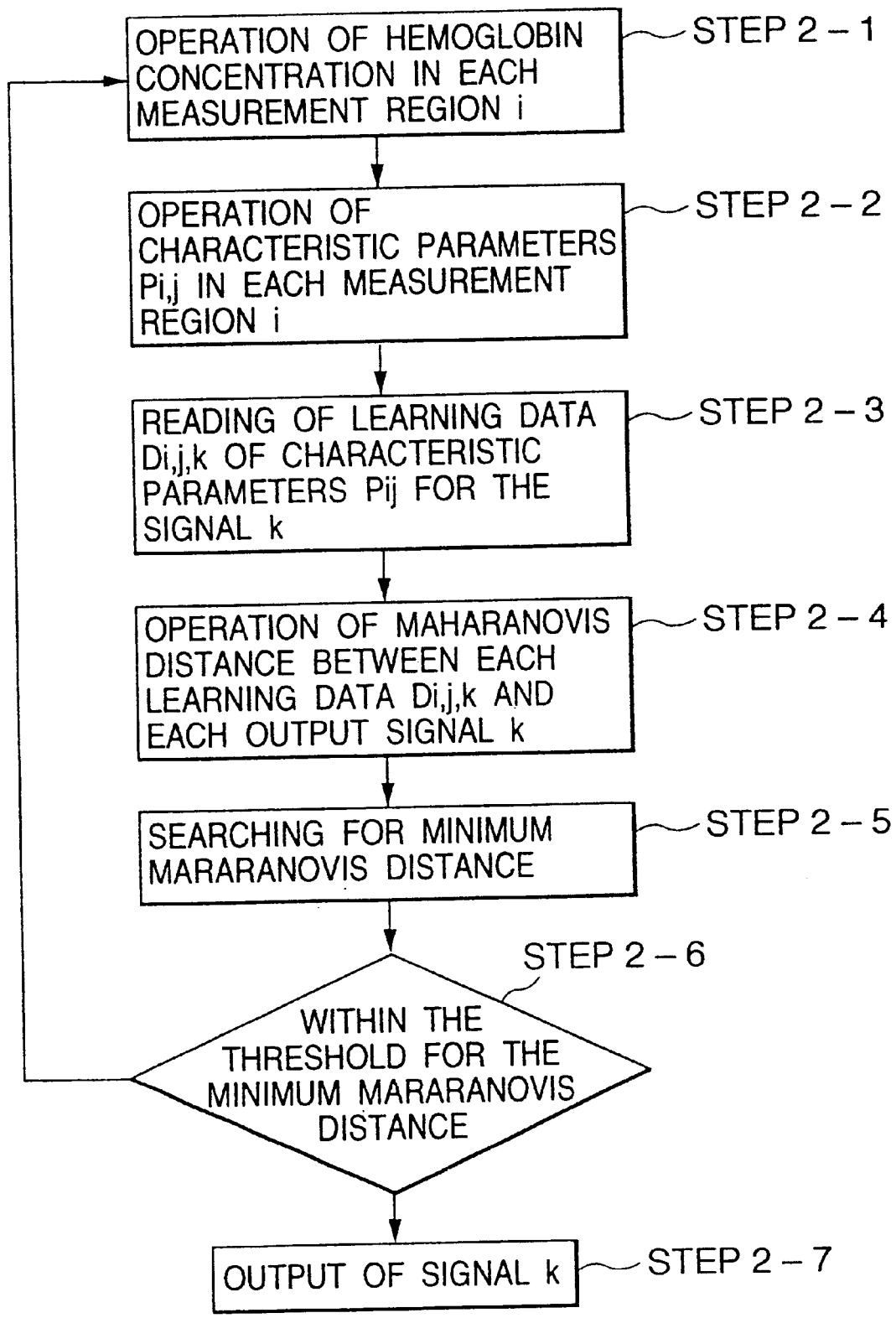
FIG. 35 is a flowchart for describing a second operation procedural example in the operation unit employed in the embodiment shown in FIG. 33.

FIG. 35 is a flowchart for describing a second operation procedural example of the operation unit 120.

The second operation procedural example shows the case in which no one-to-one correspondence is made between the value of change in oxyhemoglobin concentration, deoxyhemoglobin concentration or total hemoglobin concentration, which has been measured in each measurement region and each of signals to be inputted to the external equipment 200. In the previous first operation procedural example, the signal from the predetermined measurement region (specific intracerebral region related to the specific functional operation) is selectively taken out and the taken-out signal is caused to correspond to the specific functional operation in a one-to-one relationship. However, there may be a case in which when an operator intends to shift the cursor to the left, the operator must imagine [moving the left hand] correspondingly, so that the function of actual external equipment differs from an operator's intention. The second operation procedural example to be described later takes into consideration the above-described problem that arises in the aforementioned first operation procedural example.

The measurement regions are first set to a plurality of arbitrary points (i points) respectively. Incident optical fibers and detection optical fibers are placed in the respective measurement regions. The intensities of lights passing through the living body in the respective measurement regions are measured and the results of measurements are inputted to the operation unit 120. That is, the present example is not intended to take aim at predetermined specific measurement regions (specific intracerebral regions related to specific functional operations) and selectively measure signals from these specific measurement regions. Measurement optical fiber pairs are placed in a plurality of arbitrary positions on the surface of a subject (human head) without specifically specifying the measurement regions. Further, the operation unit 120 measures repeatedly many times and learns hemoglobin concentration changes at these plural positions, incident to functional brain activities at the time that an operator imagines the operation for inputting each signal to the external equipment (e.g., the computer). Thereafter, the results of learning are stored in the memory unit 130 in advance. Further, the operation unit 120 determines hemoglobin concentrations and characteristic parameters by its operation from the actually-measured signals. The operation unit 120 searches whether the characteristic parameters similar to the data stored in the memory unit 130 exist in the data, and determines a signal to be inputted to the external equipment.

The second operation procedural example will hereinafter be described in detail along with the flowchart shown in FIG. 35.

(Step 2-1)

An oxy-, deoxy- or total-hemoglobin concentration is determined by operation from the intensities of transmitted lights of respective wavelengths from the respective measurement regions i.

(Step 2-2)

Values Pi, j (matrix values) of respective characteristic parameters j in each measurement region i are determined by operation from each or arbitrary hemoglobin concentration determined by operation in step 2-1. As the characteristic parameters j, for example, integrated values of respective or arbitrary hemoglobin concentrations at arbitrary time intervals, the rates of changes in the respective or arbitrary hemoglobin concentrations at arbitrary times, or the intensities of arbitrary frequencies corresponding to time changes in respective or arbitrary hemoglobin concentrations are used. These can be determined in various ways.

(Step 2-3)

Here, the types of signals outputted from the operation unit 120 are defined as k types. General learning data or learning data on individual operators has been stored in the memory unit 130 in advance.

A learning data structure is standard deviations and mean values every characteristic parameters j at every measurement regions i having the same structures every output signals k. Namely, a probability distribution of the characteristic parameters is predicated on the Gaussian distribution. The Gaussian function can be described by the standard deviations and mean values.

When, for example, the external equipment 200 is regarded as a computer and signals k outputted from the operation unit 120 are inputted to the computer, the cursor is set so as to move to the right. Further, the operator puts on the measurement system 110 and imagines [shifting the cursor to the right] plural times in advance. At this time, standard deviations and mean values are calculated every characteristic parameters j at every measurement regions i to be measured. The resultant standard deviations and mean values every characteristic parameters j at every measurement regions i are stored in the memory unit 130 as learning data about the signals k. In step 2-3, the stored learning data Di, j, k are read into the operation unit 120.

FIG. 36 shows a data structure of the learning data Di, j, k. In FIG. 36, S indicate standard deviations and A indicate mean values, and dotted lines ( . . . ) means the omission. Further, the measurement regions i are defined as n in number and the number of types of the characteristic parameters j is defined as m.

(Step 2-4)

Maharanovis distances MDk are determined by operation every signals k, using all the stored learning data Di, j, k and the values Pi, j of the respective characteristic parameters j at every measurement regions i, which have been computed in step 2-2. Each of the Maharanovis distances is given by the known simple equation.

(Step 2-5)

The minimum Maharanovis distance MDk(min) is searched from the Maharanovis distances MDk determined by operation in step 2-4 every signals k. If the minimum value is selected from the values of the 1 to k signals, it is then defined as the minimum Maharanovis distance MDk (min).

(Step 2-6)

The operation unit 120 determines whether the minimum Maharanovis distance MDk(min) falls within an arbitrary threshold range. If it is determined that the minimum Maharanovis distance MDk(min) falls within the threshold range, then the operation unit 120 proceeds to step 2-7. If it is determined that the minimum Maharanovis distance MDk (min) falls outside the threshold range, then the operation unit 120 returns to step 2-1 referred to above.

(Step 2-7)

The operation unit 120 outputs the signals k obtained in the above-described manner and sends the same to the external equipment (computer) 200.

The second operation procedural example is an application of the Maharanovis estimation method. However, a method of applying a neutral network is also known as a third operation method to perform similar estimation. In this case, the respective characteristic parameters j at every measurement regions i are inputted to respective terminals on the input side of the neutral network and the respective signals k (k=1 to 1) are assigned to respective terminals on the output side thereof. The neutral network is learned in advance every operators or by plural operations of general operators so that arbitrary signals k are outputted according to the values of the respective characteristic parameters j at every measurement regions i. The use of the learned neutral network can provide a function similar to that obtained by the Maharanovis estimation method shown in FIG. 35 and permits the output of a signal corresponding to the imagination of a user.

In FIG. 33, the neutral network is electrically connected to a stage subsequent to the operation unit 120. The characteristic parameters are inputted to the respective terminals on the input side of the neutral network. The respective terminals on the output side of the neutral network are electrically connected to the external equipment 200.

In addition to the first, second and third operation methods, the operation unit may of course determine the type of output signal, directly using signals measured by detectors for the measurement of brain activity.

<<Sixth Embodiment>>

Figure 37:
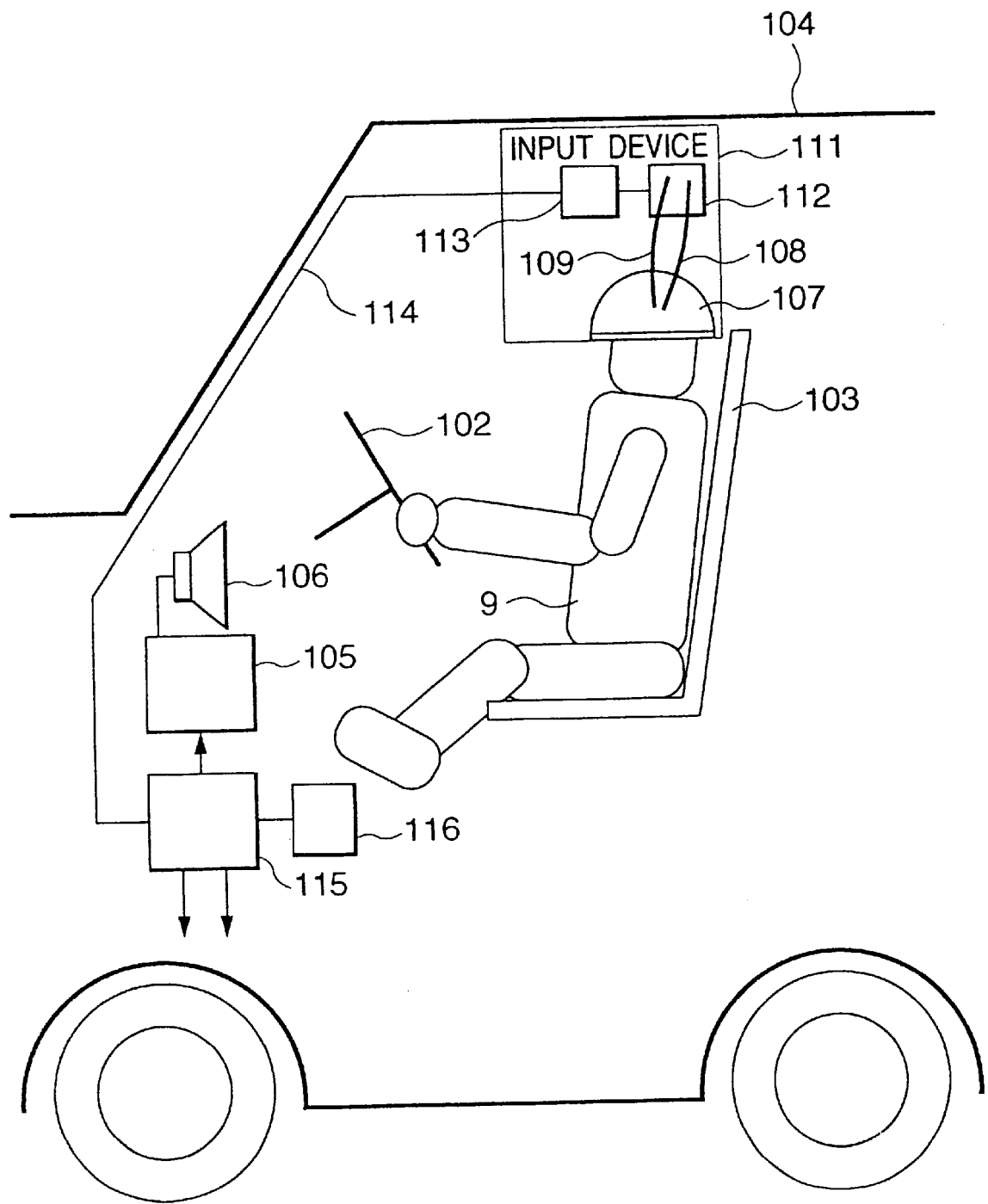
FIG. 37 is a diagram schematically illustrating a configuration of a control device by living body, according to a sixth embodiment of the present invention.

FIG. 37 schematically shows a configuration of a control device by living body, according to a sixth embodiment of the present invention.

The present embodiment shows a case in which a doze alarm is given to a vehicle driver by using a signal outputted from a measurement system of brain activity according to the present invention.

In FIG. 37, reference numerals 9, 102, 103, 104, 105, 106, 107, 108, 109, 111, 112, 113, 114, 115 and 116 indicate a driver (subject), a handle, a seat, a motor vehicle, a driver circuit, a speaker, an optical fiber fixer or optical fiber fixing helmet, a light incident optical fiber, a light collecting or detection optical fiber, an input device, an optical measurement unit for a living body (measurement system of brain activity), an input signal determination unit, a signal line, a microcomputer, and a memory unit, respectively. In the present embodiment, a subject measurement signal outputted from the optical measurement unit 112 is used to give a doze alarm to the driver 9. Namely, the input device 111 (including the optical measurement unit 112, the input signal determination unit 113, the light incident optical fiber 108, the detection optical fiber 109 and the optical fiber fixer or optical fiber fixing helmet 107) constitutes an input device by living body, according to the present invention. The microcomputer 115 is used as a piece of external equipment.

FIG. 37 shows a state in which the driver 9 takes the seat 103 and is driving the vehicle 104 while controlling the handle 102. The driver 9 is putting on the optical fiber fixer (helmet) 107. The light incident optical fibers 108 and the detection optical fibers 109 of one pair or more are fixed to the optical fiber fixer (helmet) 107. Light is always applied to the head of the driver 9 through the light incident optical fiber 108. The light passing through the living body is collected by the detection optical fiber 109 fixed to a light collecting position spaced by an arbitrary distance (e.g., about 30 mm) away from the position where the light is applied thereto. Light sources for providing the lights to be applied through the light incident optical fibers 108 are provided within the optical measurement unit 112. Similarly, optical detectors for detecting the light collected by the detection optical fibers 109 are also provided within the optical measurement unit 112.

As illustrated in the embodiment of FIG. 33, the respective incident light intensities are modulated with the modulation frequencies different from each other every different light incident positions and every different incident light wavelengths. If the phases of the light intensity signals passing through the living body detected by the optical detectors are phase-detected and the intensity components of the lights passing through the living body at every respective modulation frequencies are separated and measured, then the influence of stray lights from those other than a desired measurement position can be eliminated and the intensity components of the lights passing through the living body every wavelengths at every measurement positions can be separated and measured. A measurement position defined by each pair of incident light optical fiber 108 and detection optical fiber 109 may be set to a plurality of arbitrary positions every drivers 9. However, when characteristic portions such as a high light-transmissive frontal head, a portion in which hemo-dynamics change pronouncedly due to sleepiness, etc. have been recognized in advance, it is preferable to selectively set the measurement positions to these characteristic portions.

The input signal determination unit 113 extracts a signal indicative of sleepiness, based on a measurement signal indicative of head hemo-dynamics, which has been measured by the optical measurement unit 112. The input signal determination unit 112 comprises a memory unit which stores therein constant data necessary for the operation of hemo-dynamics, such as optical parameters like hemoglobins or the like, and learning data about the driver 9, and an operation unit for performing an operation on the hemo-dynamics and making a decision about an input signal. As described in the previous third operation procedural example, the neutral network may be used to determine the input signal.

When the sleepiness of the driver 9 is now detected by the input signal determination unit 113, a detection signal indicative of the sleepiness thereof is inputted to the microcomputer 115 through the signal line 114. The microcomputer 115 sends a signal for giving a warning-forward command to a doze alarm system composed of the driver circuit 105 and the speaker 106. When the warning command signal is inputted to the doze alarm system, the driver circuit 105 sends a warning tone signal to the speaker 106 where a warning tone is produced. As a warning means of the doze alarm system, various means such as a light-stimulating one or one for vibrating the seat 103, etc. are considered as well as one for stimulating the driver with the above tone. The microcomputer 115 may select voice or tone signal data stored in the memory unit 116 according to the level of an alarm and output a voice alarm indicative of the contents of an alarm such as [Danger !, Danger !, . . . ] It is also possible to provide the input device 111 within the optical fiber fixer 107 and send a signal to the doze alarm system through an electromagnetic wave without the use of the signal line 114. Further, when the microcomputer 115 has determined a rise in the alarm level, the microcomputer 115 may directly output signals for applying the brake and stopping the engine, for example, as indicated by arrows extending in a downward direction.

The alarm generating system using such living-body measurement signals can be applied to the operations of all the moving means such as an airplane, a train, etc. as well as to the vehicle driving shown in FIG. 37. The alarm generating system can be applied as a system for determining sensitive states such as a doze, fatigues, the feeling of irritation, redout, blackout, etc. interfering with the vehicle driving while these moving means are being driven, and automatically generating an alarm. Incidentally, the redout and blackout indicate symptoms in which an intracerebral blood stream is focused on a local place by large acceleration during the control of the airplane or the like, so that the sense of vision results in trouble and the driver loses consciousness.

Thus, the input device by living body, according to the present invention can be also applied as, for example, an environmental control device by being used as a device for inputting each signal to the microcomputer. Namely, the input device can be also utilized as a device capable of determining a subjective state sensitive to cold, hot and relaxed surroundings and controlling environmental conditions such as environmental temperatures, environment music, brightness, a state of an image, etc.

Further, the input device can be also applied as a learning level determining device. Namely, it can be utilized as a device for determining a learning level of learning, motion (including rehabilitation) or the like and displaying the degree of its skillness. Moreover, it can be used as a training device for repeatedly training a person on the basis of the displayed degree of skillness.

It is also possible to apply the input device as a diagnostic and warning device for medical care. Namely, it can be applied to a diagnostic device for determining the focus of epilepsy of an epileptic patient, a functional brain activity detection device for a patient having a cerebral disease, a warning device for an epileptic fit, etc.

The input device by living body can be also applied as a device for displaying the senses and thoughts of those such as a patient, an infant and animals or the like each having a muscle disease or a vegetative state, which are unable to transfer their intentions to the outside or originally do not come to an understanding. Described more specifically, the input device captures an infant thought and converts it into a digital electric signal, followed by input to the microcomputer. Further, meaningful words are registered in a memory in advance and determined and selected therefrom. Thereafter, the selected word is outputted by voice. Moreover, the input device captures information on the inside brain the infant and detects a momentary change in intracerebral activity. Thereafter, the input device inputs its change to a voice synthesis circuit as a phoneme and allows the infant to transfer the thought or will of the infant as a voice. Moreover, the attachment of the input device by living body according to the present invention to animals, pets or the like can also provide recognizing what do these animals desire.

Further, the input device can be also applied to a device for determining feelings of joy and anger and transferring information about the feelings through a videophone or the like. Expression can be added onto a computer graphics picture of a transmitter's face, which is displayed on the receiver side, judging from the feelings information on the transmitter side, which is transferred by the device.

The input device can be applied even to a device for determining concentration and displaying it thereon. Further, it can be also applied to a lie detector.

According to the present invention, as has been described above, since the localized brain function information is measured by the brain function measurement system and the resultant measured signals are used as the signals to be inputted to the external equipment, the external equipment can be controlled without using the keyboard, mouse, handle, etc. Further, the measurement system can be applied even to the vehicle warning device, the environmental control device, the learning level determining device, the diagnostic and warning device for medical care, the intention display device, the information transfer device, the concentration determination device and the lie detector or the like. Accordingly, the communications that were previously impossible between persons having no information transferring means, can be also achieved.

While the present invention has been described with reference to the illustrative embodiments, this description is not intended to be construed in a limiting sense. Various modifications of the illustrative embodiments, as well as other embodiments of the invention, will be apparent to those skilled in the art on reference to this description. It is therefore comtemplated that the appended claims will cover any such modifications or embodiments as fall within the true scope of the invention.

What is claimed is:

1. An optical measurement instrument for a living body, comprising:

light incident means for simultaneously applying lights of at least one wavelength in a visible-infrared region to a plurality of incident positions on the surface of a subject;

light detection means for simultaneously detecting lights obtained by allowing said applied lights to pass through the subject at a plurality of detection positions on the surface of the subject; and imaging means for imaging information on the inside of the subject using detected signals outputted from said light detection means, said light incident means including light modulation means for intensity-modulating the applied lights with modulation frequencies which are different for each of said incident positions, said light detection means including selection and detection means for selecting and detecting transmitted light components corresponding to respective ones of said modulation frequencies at said respective detection positions from said applied lights relative to said plurality of detection positions.

2. An optical measurement instrument for a living body, comprising:

light incident means for simultaneously applying lights of a plurality of wavelengths in a visible-infrared region to a plurality of incident positions on the surface of a subject;

light detection means for simultaneously detecting lights obtained by causing said incident lights to pass through the subject at a plurality of detection positions on the surface of the subject; and imaging means for imaging information on the inside of the subject using detected signals outputted from said light detection means, said light incident means including light modulation means for intensity-modulating the lights applied to said plurality of incident positions with modulation frequencies which are different for each of said incident positions, said light detection means including selection and detection means for selecting and detecting transmitted light components corresponding to respective ones of said modulation frequencies at said respective detection positions from said applied lights relative to said plurality of detection positions.

3. An optical measurement instrument for a living body, comprising:

light incident means for simultaneously applying lights of a plurality of wavelengths in a visible infrared region to a plurality of incident positions on the surface of a subject;

light detection means for simultaneously detecting lights obtained by transmitting said applied lights through the subject at a plurality of detection positions on the surface of the subject; and imaging means for imaging information on the inside of the subject using detected signals outputted from said light detection means, said light incident means including light modulation means for intensity-modulating the lights applied to said plurality of incident positions with modulation frequencies which are different for each of said incident positions and for each of said wavelengths, said light detection means including selection and detection means for selecting and detecting transmitted light components corresponding to respective ones of said modulation frequencies at said respective detection positions from said applied lights relative to said plurality of detection position.

4. An optical measurement instrument for a living body according to any of claims 1 to 3, wherein said light incident means transmits and applies the lights to said plurality of incident positions through light incident optical fibers respectively provided so as to correspond to said incident positions, and said light detection means transmits and detects the transmitted lights to be applied to said plurality of detection positions through light detection optical fibers respectively provided so as to correspond to said detection positions.

5. An optical measurement instrument for a living body according to any of claims 1 to 3, wherein said light incident means includes a plurality of light sources for outputting lights to said plurality of incident positions, and said light modulation means intensity-modulates the lights outputted from said plurality of light sources with modulation frequencies different from each other to thereby intensity-modulate the lights incident onto said plurality of incident positions with modulation frequencies different from each other.

6. An optical measurement instrument for a living body according to claim 5, wherein said plurality of light sources are a plurality of laser diodes.

7. An optical measurement instrument for a living body according to claim 6, wherein said light modulation means by-modulation drives said plurality of laser diodes with modulation frequencies different from each other to thereby intensity-modulate lights incident onto said plurality of incident positions with modulation frequencies different from each other.

8. An optical measurement instrument for a living body according to any of claims 1 to 3, wherein said light incident means includes a single light source for outputting light to said plurality of incident positions and a plurality of light transmission paths for distributing and transmitting the light outputted from said single light source as distributed lights to said plurality of incident positions, and said light modulation means intensity-modulates the distributed lights to said plurality of light transmission paths with modulation frequencies different from each other to thereby intensity-modulate the light incident onto said plurality of incident positions with modulation frequencies different from each other.

9. An optical measurement instrument for a living body according to claim 8, wherein said light modulation means intensity-modulates the distributed lights to said plurality of light transmission paths, using liquid-crystal filters or light choppers.

10. An optical measurement instrument for a living body according to any of claims 1 to 3, wherein said plurality of incident positions and said plurality of detection positions are placed and set so that when a square lattice is virtually set onto the surface of the subject, the lights are applied onto nodes of the square lattice and the transmitted lights are respectively detected at the nodes thereof.

11. An optical measurement instrument for a living body according to claim 10, wherein said plurality of incident positions and said plurality of detection positions are respectively alternately placed on four nodes of respective unit lattices of said square lattice.

12. An optical measurement instrument for a living body according to any of claims 1 to 3, further comprising a measurement probe wherein light incident optical fibers for transmitting the applied lights to said plurality of incident positions on the surface of the subject and light detection optical fibers for transmitting the transmitted lights to said plurality of detection positions are fixedly placed under a predetermined position relationship.

* * * * *